(12) United States Patent
Muftuoglu et al.

(10) Patent No.: US 11,883,419 B2
(45) Date of Patent: Jan. 30, 2024

(54) DNA POLYMERASE GAMMA INHIBITOR AND USES THEREOF

(71) Applicants: ACIBADEM MEHMET ALI AYDINLAR UNIVERSITESI, Atasehir/Istanbul (TR); SABANCI UNIVERSITESI, Tuzla/Istanbul (TR); KOC UNIVERSITESI, Sariyer/Istanbu (TR)

(72) Inventors: Meltem Muftuoglu, Atasehir/Istanbul (TR); Batu Erman, Tuzla/Istanbul (TR); Burak Erman, Sariyer/Istanbul (TR)

(73) Assignees: ACIBADEM MEHMET ALI AYDINLAR UNIVERSITESI, Atasehir/Istanbul (TR); SABANCI UNIVERSITESI, Tuzla/Istanbul (TR); KOC UNIVERSITESI, Sariyer/Istanbul (TR)

(*) Notice: Subject to any disclaimer, the term of this patent is extended or adjusted under 35 U.S.C. 154(b) by 612 days.

(21) Appl. No.: 17/255,572

(22) PCT Filed: Jun. 25, 2018

(86) PCT No.: PCT/TR2018/050320
§ 371 (c)(1),
(2) Date: Dec. 23, 2020

(87) PCT Pub. No.: WO2020/005171
PCT Pub. Date: Jan. 2, 2020

(65) Prior Publication Data
US 2021/0275548 A1    Sep. 9, 2021

(51) Int. Cl.
*A61K 31/655* (2006.01)
*A61P 35/00* (2006.01)

(52) U.S. Cl.
CPC ............ *A61K 31/655* (2013.01); *A61P 35/00* (2018.01)

(58) Field of Classification Search
None
See application file for complete search history.

(56) References Cited

PUBLICATIONS

Will, "On the Volumetric Determination of Boric Acid", Journal of the American Chemical Society, 1888, vol. 10, No. 2, pp. 43-44.*
Liao L-L et al: "Triphenylmethane dyes as inhibitors of reverse transcriptase RNA polymeras e and protein synthesis: structure activity relationships", Journal of Medicinal Chemistry, vol. 18, No. 1, 1975, pp. 117-120; http://dx.doi.org/10.1021/jm00235a029 ; retrieved Dec. 22, 2020.
Frid et al: "Congo red and protein aggregation in neurodegenerative diseases", Brain Research Reviews, vol. 53, No. 1, Dec. 6, 2006 pp. 135-160; http://dx.doi.org/10.1016/j.brainresrev.2006.08.001 ; retrieved Dec. 22, 2020.
Ryohei Sasaki et al: "DNA polymerase [gamma] inhibition by vitamin K3 induces mitochondria-mediated cytotoxicity in human cancer cells", Cancer Science, vol. 99, No. 5, May 1, 2008, pp. 1040-1048; https://onlinelibrary.wiley.com/doi/epdf/10.1111/j.1349-7006.2008.00771.x ; retrieved Dec. 22, 2020.
A Mansouri: "Tacrine inhibits topoisomerases and DNA synthesis to cause mitochondrial DNA depletion and apoptosis in mouse liver", Hepatology, vol. 38, No. 3, Sep. 1, 2003, pp. 715-725; http://dx.doi.org/10.1053/jhep.2003.50353 ; retrieved Dec. 22, 2020.
Chung K-T et al: "Mutagenicity of azo dyes: Structure-activity relationships", Mutation Research/Reviews in Genetic Toxicology, vol. 277, No. 3, Sep. 1, 1992, pp. 201-220; http://dx.doi.org/10.1016/0165-1110(92)90044-A ; retrieved Dec. 22, 2020.
International Search Report and Written Opinion for corresponding PCT application No. PCT/TR2018/050320, dated Sep. 11, 2019.
International Preliminary Report on Patentability for corresponding PCT application No. PCT/TR2018/050320, completed Oct. 12, 2020.

* cited by examiner

*Primary Examiner* — Joseph R Kosack
(74) *Attorney, Agent, or Firm* — Notaro, Michalos & Zaccaria P.C.

(57) ABSTRACT

Pol γ protein inhibitor compounds are useful for selectively inhibiting the growth of MLH1 mutant/deficient tumor or cancer cells due to a synthetic lethal relationship between MLH1 and Pol γ. The compounds were shown to directly interact with Pol γ and inhibit its biological function and cause cancer cell death and an inhibition of tumor or cancer cell growth in multiple assays.

3 Claims, 10 Drawing Sheets

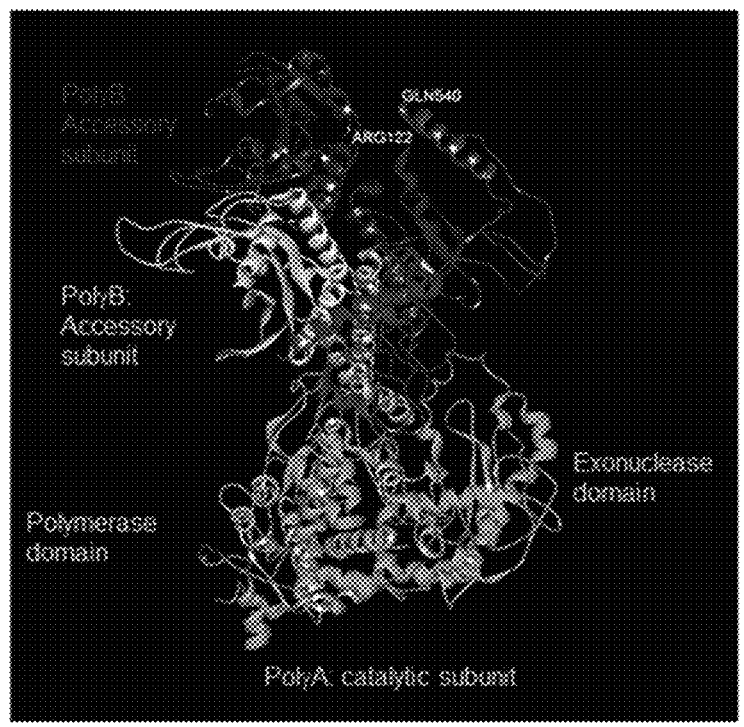
Figure 1-a
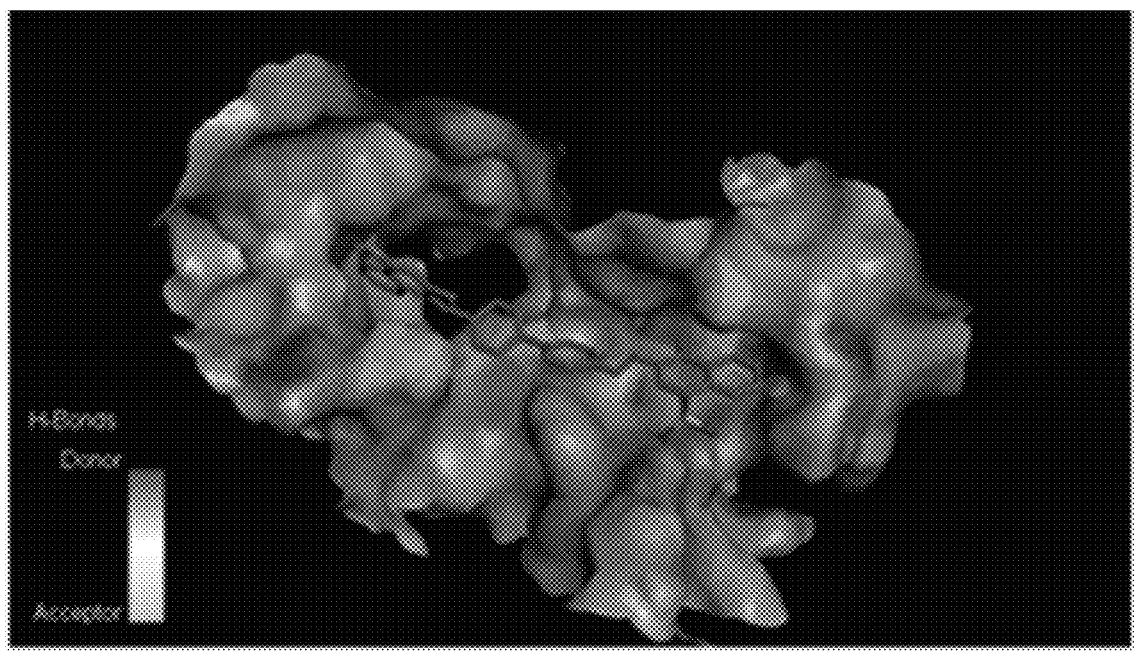
Figure 1-b

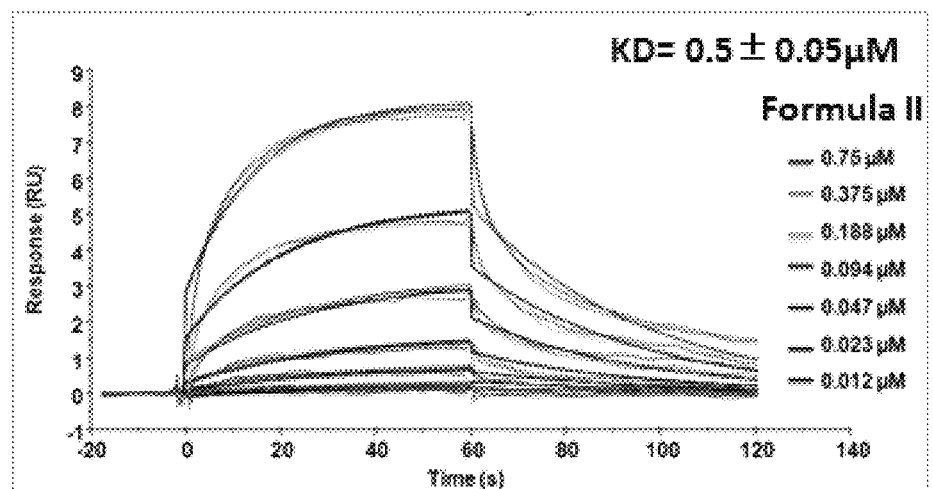
Figure 2
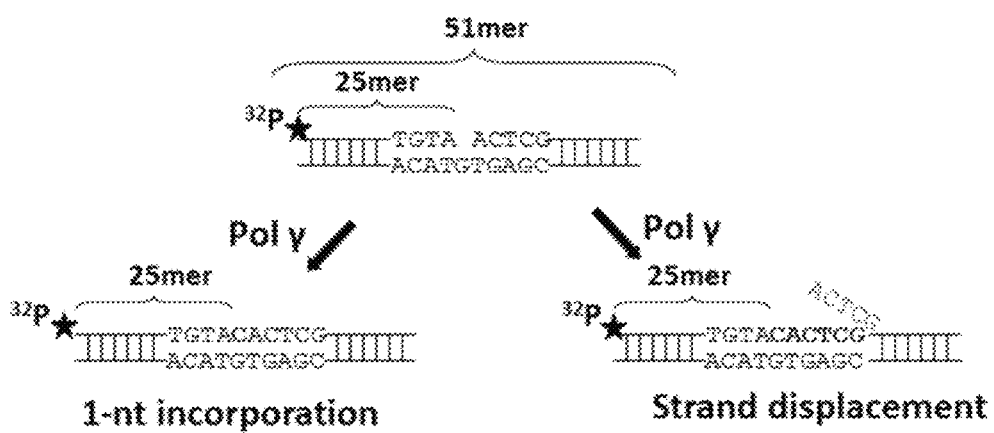
Figure 3-a

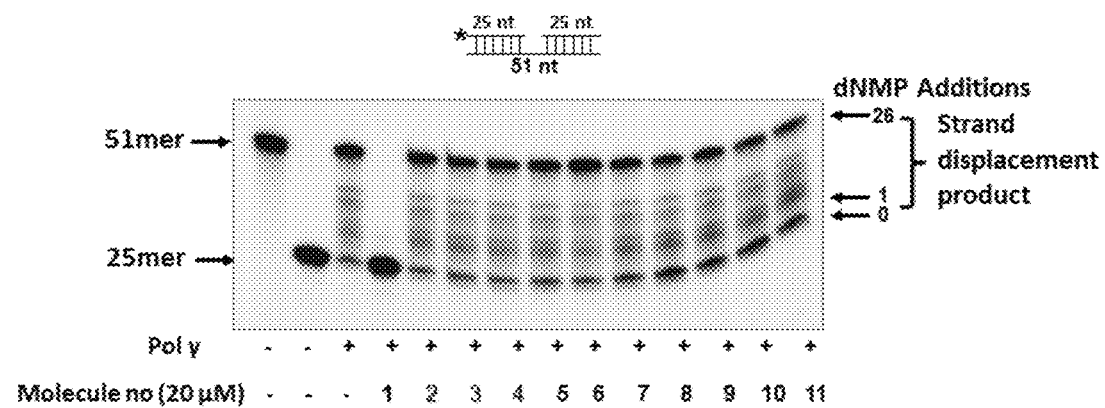
Figure 3-b
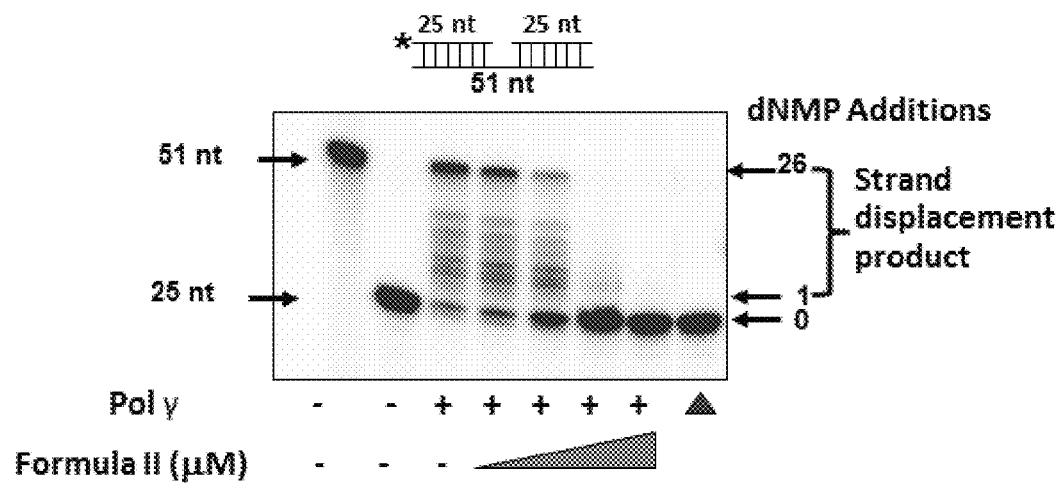
Figure 3-c

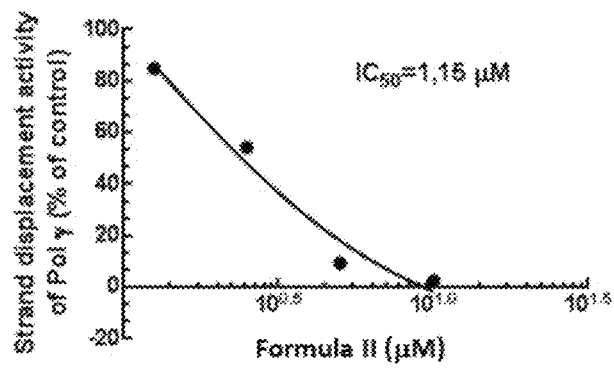
Figure 3-d
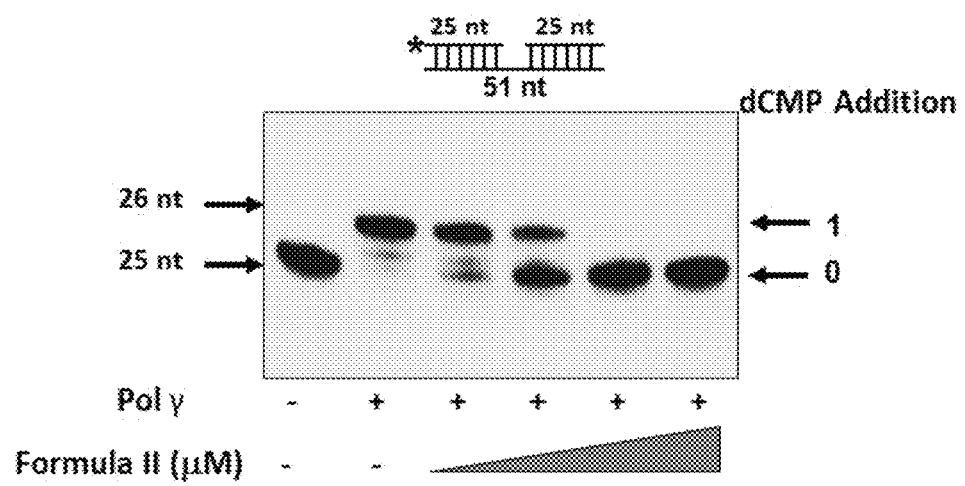
Figure 3-e

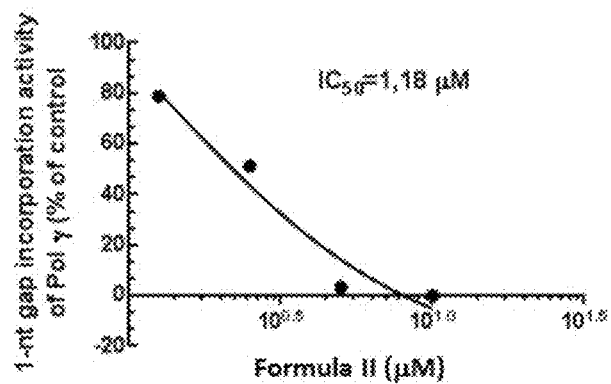
Figure 3-f
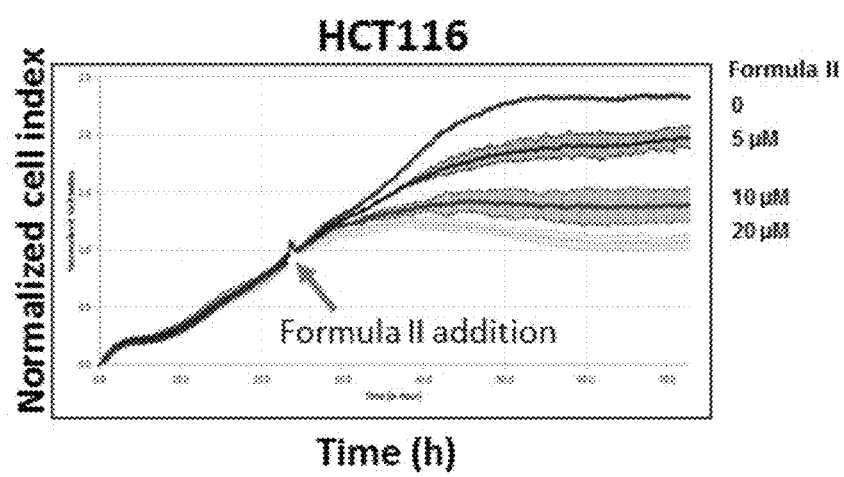
Figure 4-a

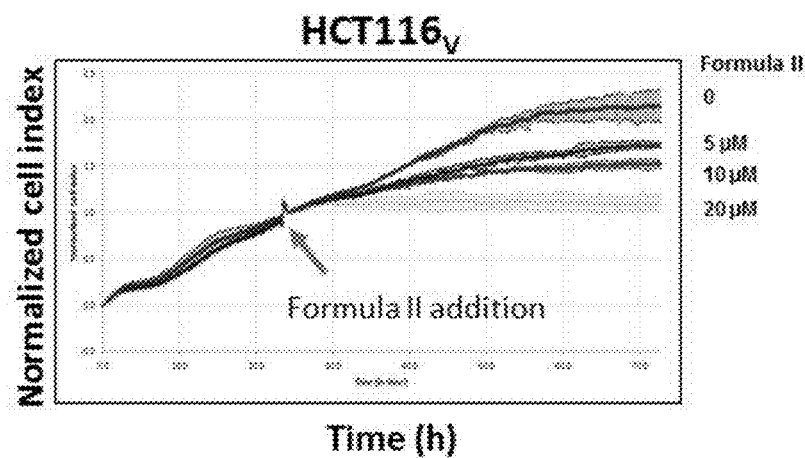
Figure 4-b
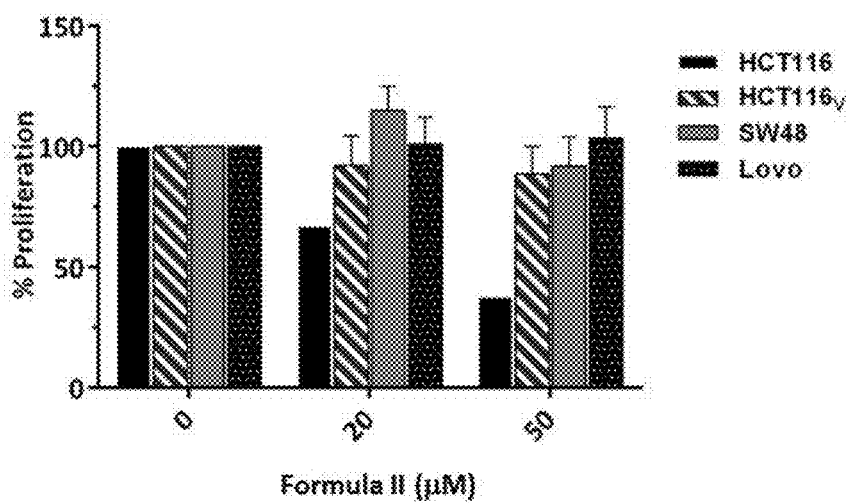
Figure 4-c

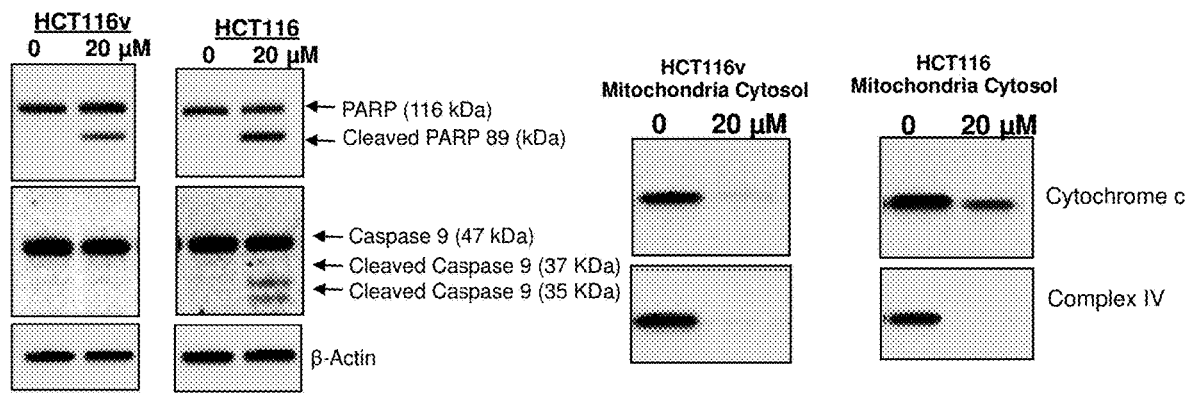
Figure 5-a
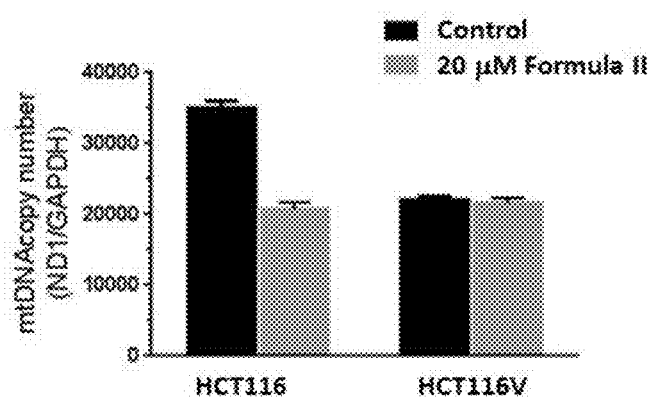
Figure 5-b

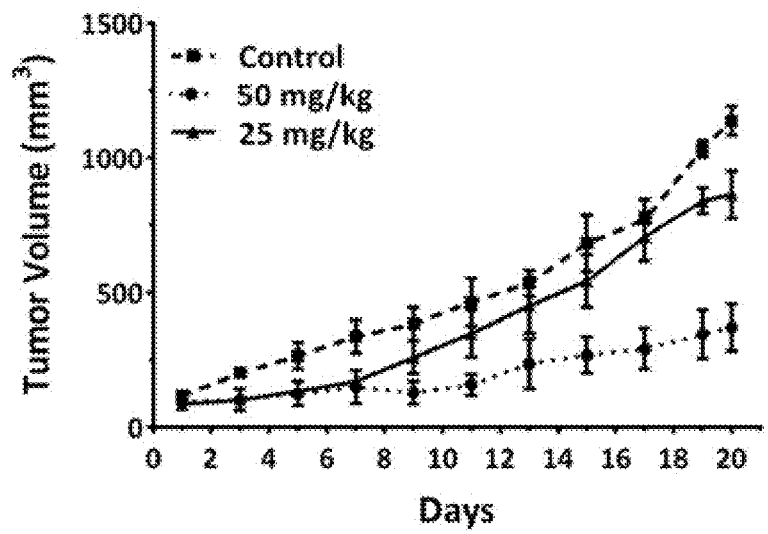
Figure 6-a
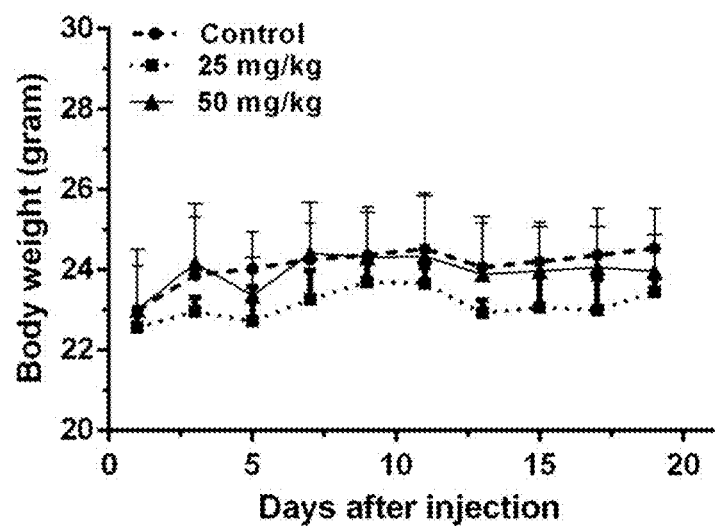
Figure 6-b

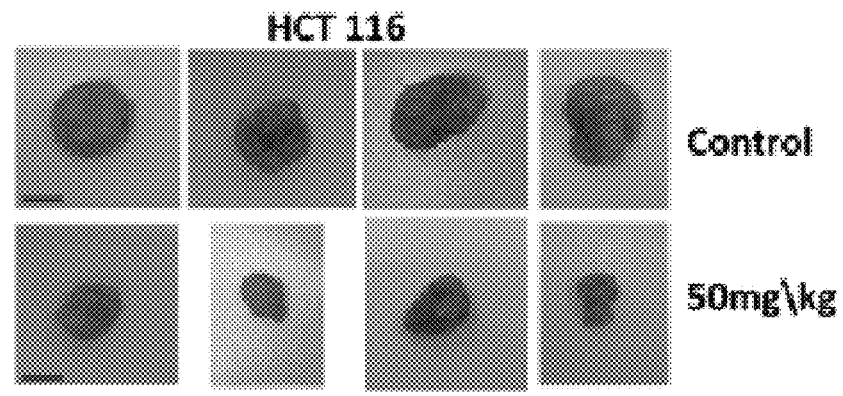
Figure 6-c
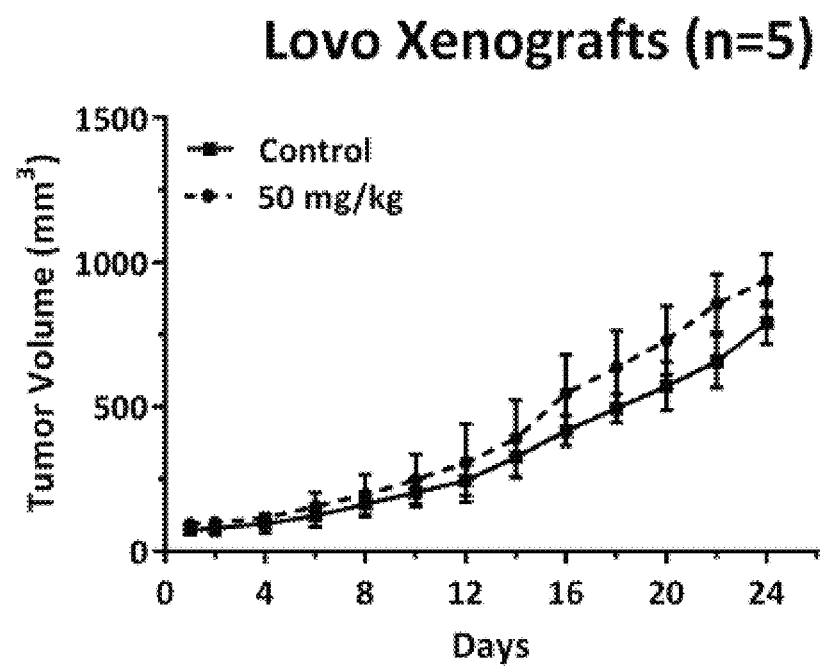
Figure 7-a

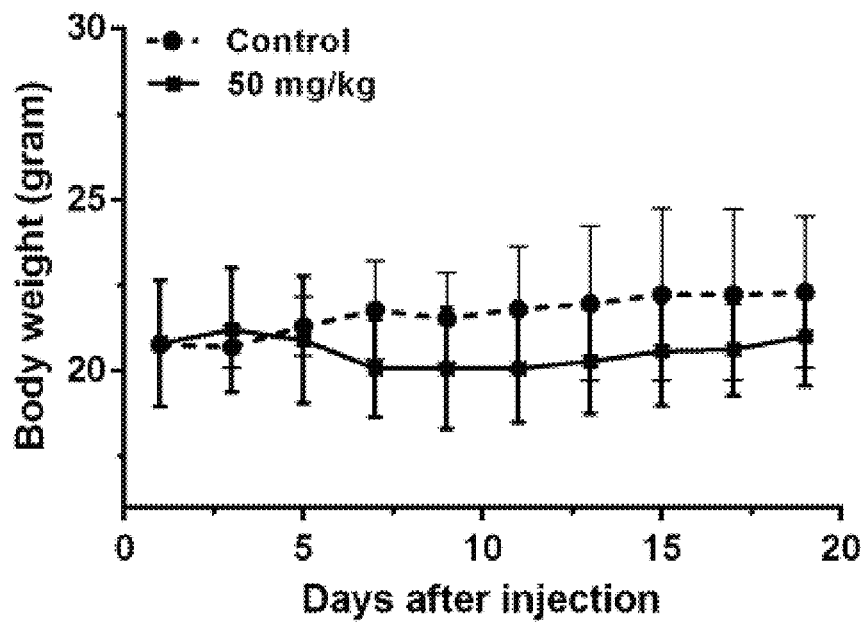
Figure 7-b
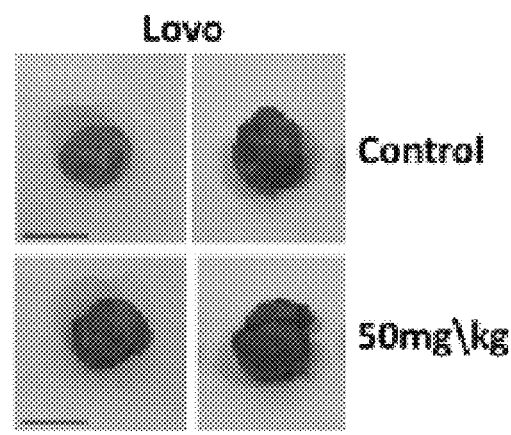
Figure 7-c

DNA POLYMERASE GAMMA INHIBITOR AND USES THEREOF

FIELD OF THE INVENTION

The invention encompasses novel compounds and pharmaceutical compositions comprising the compounds of the following formula (I): pharmaceutically acceptable salts or prodrugs thereof that are useful for inhibiting the function of the DNA polymerase gamma protein (Pol γ) or for inhibiting the growth of a cancer cell or tumor growth. They are particularly useful for the treatment of MLH1 deficient tumors.

The invention also encompasses administrating at least one novel Pol γ protein inhibitor compound of the invention which is useful for selectively inhibiting the growth of MLH1 deficient cancer cells (for example, HCT116) due to the synthetic lethal relationship between MLH1 and Pol γ.

BACKGROUND OF THE INVENTION

DNA Polymerase gamma (Pol γ) is a mitochondrial DNA (mtDNA) polymerase enzyme which plays a role in the mitochondrial base excision repair (BER) and mtDNA replication. Thus, inhibiting the activity of Pol γ will interfere with mtDNA stability and/or the function of the mitochondrial BER pathway. Because cancer cell mitochondria are different from the mitochondria in normal cells, and because of the synthetic lethal interaction between Pol γ and MLH1, Pol γ inhibition is a powerful target for selective cancer treatment. Inhibition of Pol γ in MLH1 deficient cancer cells is expected to selectively affect these cells without affecting MLH1 proficient somatic cells of the rest of the organism.

The crystal structure of the Pol γ protein revealed that it is a heterotrimeric protein, consisting of a homodimer of accessory subunits (Pol γB; MW. 53 kDa) and a catalytic subunit (Pol γA; MW. 139 kDa). The catalytic subunit Pol γ has polymerase, dRP lyase and 3'-5'-exonuclease activities. Accessory subunits Pol γB have no intrinsic enzymatic activity but instead increases the processivity of the Pol γA subunit.

The cytotoxic (tumor killing) effects of most chemotherapeutic agents and radiation therapy are related to their ability to induce DNA damage. Conversely, DNA repair pathways act to maintain genomic stability, mediate resistance to DNA damage and protect the cells from the cytotoxicity of chemotherapeutics. The DNA-repairing system of cancer cells therefore counteracts cancer treatment. Therefore, successful cancer therapy must be composed of a combination of drugs or a single drug that generates DNA damage while inhibiting DNA repair pathways. This kind of therapy could ideally selectively kill tumor cells while sparing normal cells. This selectivity can be achieved through DNA repair based synthetic lethal interactions. The definition of synthetic lethality is that two different genes or pathways together cause cell death, but independently are not sufficient to kill the cell. In other words, synthetic lethality arises when a combination of deficiencies in the expression of two genes leads to cell death, whereas a deficiency in only one of these genes does not show a severe phenotype. For example, the PARP gene/protein (involved in the BER pathway) displays synthetic lethality with the BRCA1 or BRCA2 genes/proteins (required for homologous recombination repair). Subtypes of breast cancer have defective BRCA1/2 genes and several PARP inhibitors are now being used in clinical trials for the treatment of these breast cancers, with the hope of specifically killing the BRCA1/2 mutant/deficient tumors more effectively than BRCA1/2 sufficient normal breast tissue (2-4).

Another example of synthetic lethality is the interaction between MLH1 and Pol γ. Because of this interaction, the inhibition of Pol γ may be an effective approach to specifically kill MLH1 deficient cancers. MLH1 is a tumor suppressor protein involved in the mismatch repair (MMR) pathway that participates in the repair of base mispairs arising during DNA replication. It plays a role in the repair of both the nuclear and mitochondrial genomes. Pol γ is a mitochondrial DNA polymerase enzyme which plays a role in the mitochondrial BER pathway and mtDNA replication. DNA repair pathways are specific to DNA lesions but there is also an overlap between substrate specificity. BER is the major pathway to repair oxidative DNA damage but MMR pathway also plays a role in the repair of oxidative DNA damage.

Germline mutations in the MLH1 gene result in a deficiency of the MMR pathway and increase the cumulative lifetime risk developing hereditary nonpolyposis colorectal cancer (HNPCC; Lynch syndrome) and approximately 15% of sporadic colorectal cancers are already deficient in the MMR pathway. MLH1 acts as a tumor suppressor protein where tumor cells can have a complete loss of MLH1 function but normal cells mostly retain at least one functional MLH1 copy (allele). Therefore, an inhibitor is required to specifically kill MLH1 mutant/deficient tumor or cancer cells without damaging normal cells through Pol γ inhibition.

In this study, we identified that the compounds described herein directly interact with Pol γ and inhibit its biological function in multiple assays. In addition, we identified that novel Pol γ inhibitor described here in selectively inhibits MLH1 deficient tumor growth.

BRIEF DESCRIPTION OF THE INVENTION

A pol γ protein inhibitor compound having the formula I:

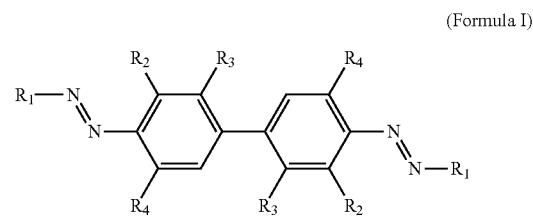

(Formula I)

and/or pharmaceutically acceptable salts, pharmaceutically acceptable solvates or prodrugs thereof.

$R_1$ is selected from compound A or compound B.

Compound A which is represented by:

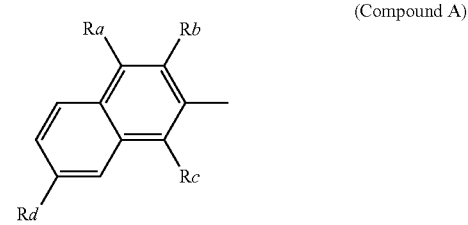

(Compound A)

wherein, $R_a$ is selected from the group comprising $SO_3H$, $SO_2NH_2$, COOH or H $R_b$ is selected from the group comprising $SO_3H$, $SO_2NH_2$, COOH, $NH_2$, OH, F or H $R_c$ is selected from the group comprising $NH_2$, $NHCOCH_3$, $NHCOCF_3$, F, OH or H $R_d$ is selected from the group comprising $NH_2$, OH, F or H or compound B which is represented by:

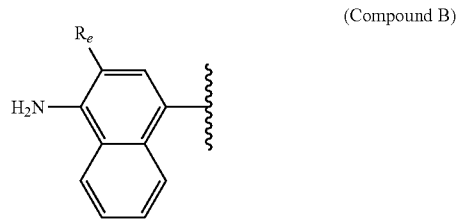

(Compound B)

wherein, $R_e$ is selected from the group comprising $SO_3H$, $SO_2NH_2$, COOH and $R_2$ is selected from the group comprising H, $CH_3$, $CF_3$, $OCH_3$, $SCH_3$, $OCF_3$, F, Cl, Br, C2H5 or n-C3H7;

$R_3$ is selected from the group comprising H, $CH_3$, $CF_3$, $OCH_3$, $SCH_3$, $OCF_3$, F or Cl;

$R_4$ is selected from the group comprising H, $CH_3$, $CF_3$, $OCH_3$, $SCH_3$, $OCF_3$, F, Cl, Br, or C2H5;

The Pol γ protein inhibitor compound having the formula II is disclosed with the present invention.

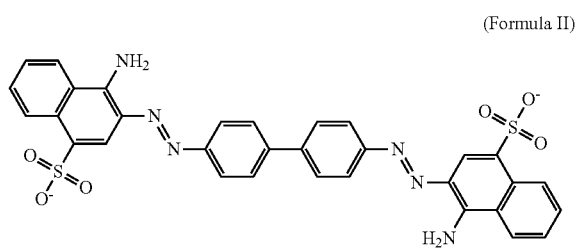 [SMILES: Nc1c(/N=N/c2ccc(-c3ccc(/N=N/c4cc(S(=O)(=O)[O-])c5ccccc5c4N)cc3)cc2)cc(S(=O)(=O)[O-])c2ccccc12]

(Formula II)

With the present invention, it is also disclosed the use of a therapeutically effective amount of Pol γ protein inhibitor compound in the treatment, prevention or delaying of MLH1-mutant/deficient tumor or cancer cells, mitochondrial cancer therapy MLH1 protein deficient cancers due to mutations in MLH1 gene (HNPCC tumor cells) or MLH1 gene promoter methylation and use of a therapeutically effective amount of Pol γ protein inhibitor compound for inhibiting mitochondrial BER pathway is disclosed.

Moreover, the use of a therapeutically effective amount of Pol γ protein inhibitor in the treatment, prevention or delaying of growing MLH1 mutant/deficient tumor or cancer cells is developed and a Pol γ protein inhibitor compound and cancer cell growth in multiple assays. The compound developed by this invention is also used in a method of treatment, prevention or delaying of growing MLH1 mutant/deficient tumor cells and tumor or cancer cell growth through mitochondrial targeted therapy.

BRIEF DESCRIPTION OF THE DRAWINGS

FIG. 1-a 3D coordinates of the crystal structure of Pol γ (PDB ID: 3IKM).

FIG. 1-b Visualization of Pol γ protein inhibitor compound in the binding pocket of the catalytic subunit of Pol γ.

FIG. 2 Response (RU)-time graph showing the direct binding kinetics of Pol γ protein inhibitor compound which is preferable Formula II to recombinant wild type human Pol γ protein.

FIG. 3-a A schematic of the 51-bp DNA substrate.

FIG. 3-b Hit molecules which were selected according to the binding kinetics to Pol γ protein.

FIG. 3-c Effect of Pol γ protein inhibitor compound on Pol γ strand displacement DNA synthesis activity on a concentration dependent manner.

FIG. 3-d Percent of control strand displacement activity determined with ImageQuant software for Pol γ protein inhibitor compound.

FIG. 3-e Effect of Pol γ protein inhibitor compound on Pol γ 1-nt incorporation activity.

FIG. 3-f Percent of control 1-nucleotide incorporation activity determined with ImageQuant software for Pol γ protein inhibitor compound.

FIG. 4-a Real time dynamic monitoring of HCT116 (MLH1 deficient; vector alone; gifts from Dr. Anatoly Zhitkovich, Brown University, USA) cell proliferation and Pol γ protein inhibitor compound induced cytotoxicity with xCELLigence system.

FIG. 4-b Real time dynamic monitoring of HCT116V (MLH1 proficient; gifts from Dr. Anatoly Zhitkovich, Brown University, USA) cell proliferation and Pol γ protein inhibitor compound induced cytotoxicity with xCELLigence system.

FIG. 4-c Effect of Pol γ protein inhibitor compound on proliferation of HCT116V, HCT116, SW48 and Lovo cell lines.

FIG. 5-a The effect of Pol γ protein inhibitor compound on apoptosis of HCT116 cell line and HCT116V cell line.

FIG. 5-b The effect of Pol γ protein inhibitor compound on mtDNA copy number of HCT116 cell line and HCT116V cell line.

FIG. 6-a HCT116 Xenograft studies, tumor volume ($mm^3$) vs days the graph.

FIG. 6-b HCT116 Xenograft studies, body weight vs days after injection graph.

FIG. 6-c HCT116 Xenograft studies, Control vs 50 g/kg image.

FIG. 7-a Lovo Xenograft studies, tumor volume (mm3) vs days the graph.

FIG. 7-b Lovo Xenograft studies, body weight vs days after injection graph.

FIG. 7-c Lovo Xenograft studies, Control vs 50 g/kg image.

OBJECT OF THE INVENTION

An object of the present invention is to provide Pol γ protein inhibitor compound that inhibits Pol γ BER DNA synthesis activity by selectively killing the above mentioned types of MLH1 mutant/deficient tumor or cancer cells without damaging normal cells.

The other object of the invention is to inhibit the growth of MLH1-deficient cancer cells due to a synthetic lethal relationship between MLH1 and Pol γ.

Another objective of the present invention is to inhibit the growth of MLH1-deficient cancer cells due to mitochondrial apoptosis.

Another objective of the present invention described herein were shown to directly interact with Pol γ and inhibit its biological function and cause cancer cell death and an inhibition of cancer cell growth in multiple assays.

Another objective of the present invention is to provide compounds that complement chemotherapeutic agents and/or radiation therapy.

The present invention is also for treating, preventing or alleviating the symptoms associated with—such as but not limited to—colon cancer, rectum cancer, breast cancer, ovarian cancer, prostate cancer, malignant melanoma, gastric cancer, lung cancer, pancreas cancer, head and neck cancers.

DETAILED DESCRIPTION OF THE INVENTION

Present invention is related to Pol γ protein inhibitor compound having the formula I:

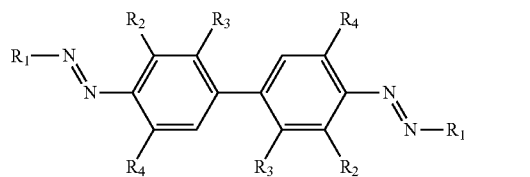

(Formula I)

and/or pharmaceutically acceptable salts, pharmaceutically acceptable solvates or prodrugs thereof.

$R_1$ is selected from Compound A or Compound B.

Compound A which is represented by:

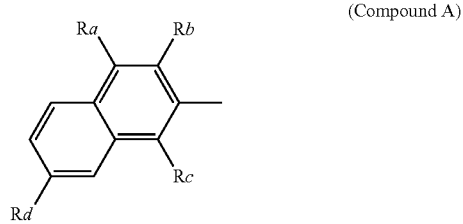

(Compound A)

wherein, $R_a$ is selected from the group comprising $SO_3H$, $SO_2NH_2$, COOH or H $R_b$ is selected from the group comprising $SO_3H$, $SO_2NH_2$, COOH, $NH_2$, OH, F or H $R_c$ is selected from the group comprising $NH_2$, $NHCOCH_3$, $NHCOCF_3$, F, OH or H $R_d$ is selected from the group comprising $NH_2$, OH, F or H or compound B which is represented by:

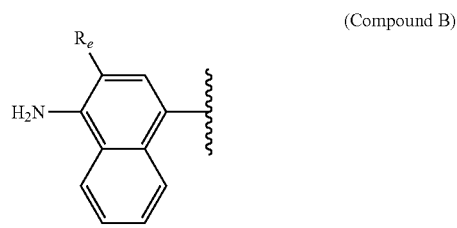

(Compound B)

wherein, $R_e$ is selected from the group comprising $SO_3H$, $SO_2NH_2$, COOH and $R_2$ is selected from the group comprising H, $CH_3$, $CF_3$, $OCH_3$, $SCH_3$, $OCF_3$, F, Cl, Br, C2H5 or n-C3H7;

$R_3$ is selected from the group comprising H, $CH_3$, $CF_3$, $OCH_3$, $SCH_3$, $OCF_3$, F or Cl;

$R_4$ is selected from the group comprising H, $CH_3$, $CF_3$, $OCH_3$, $SCH_3$, $OCF_3$, F, Cl, Br, or C2H5.

In one embodiment, the compounds of the present invention may be the following for example:

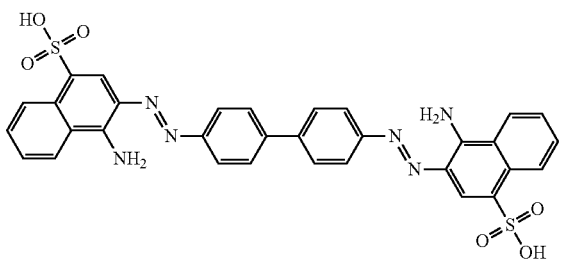 [SMILES: Nc1c(/N=N/c2ccc(-c3ccc(/N=N/c4cc(S(=O)(=O)O)c5ccccc5c4N)cc3)cc2)cc(S(=O)(=O)O)c2ccccc12]

1,1'-([1,1'-biphenyl]-4,4'-diyl)bis{4-amino-3-[(E)-diazenyl]naphthalene-1-sulfonic acid}

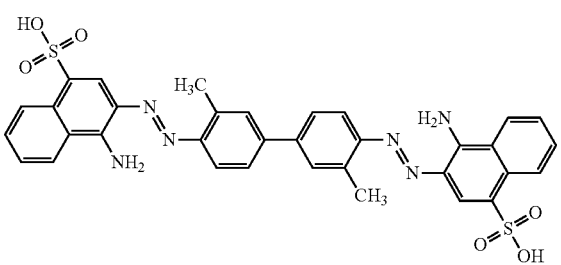

1,1'-(3,3'-dimethyl[1,1'-biphenyl]-4,4'-diyl)bis{4-amino-3-[(E)-diazenyl]naphthalene-1-sulfonic acid}

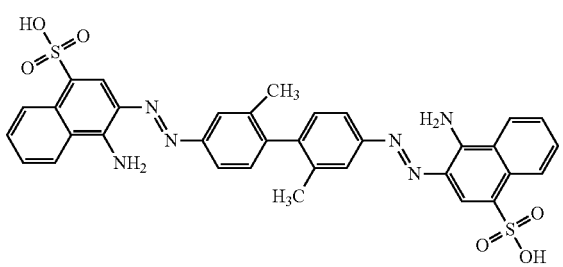 [SMILES: Cc1cc(/N=N/c2cc(S(=O)(=O)O)c3ccccc3c2N)ccc1-c1ccc(/N=N/c2cc(S(=O)(=O)O)c3ccccc3c2N)cc1C]

7

1,1'-(2,2'-dimethyl[1,1'-biphenyl]-4,4'-diyl)bis{4-amino-3-[(E)-diazenyl]naphthalene-1-sulfonic acid}

8

1,1'-(3,3',5,5'-tetraethyl[1,1'-biphenyl]-4,4'-diyl)bis{4-amino-3-[(E)-diazenyl] naphthalene-1-sulfonic acid}

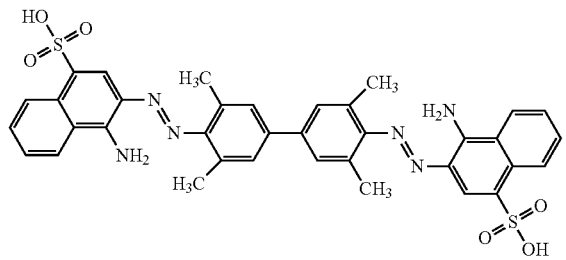 [SMILES: Cc1cc(-c2cc(C)c(/N=N/c3cc(S(=O)(=O)O)c4ccccc4c3N)c(C)c2)cc(C)c1/N=N/c1cc(S(=O)(=O)O)c2ccccc2c1N]

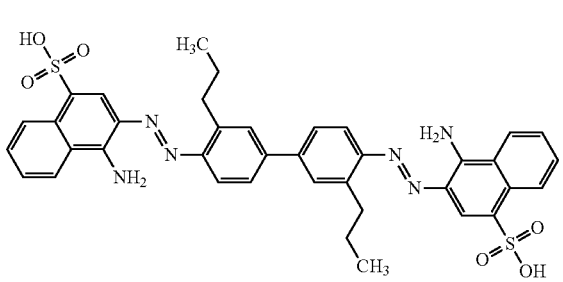

1,1'-(3,3',5,5'-tetramethyl[1,1'-biphenyl]-4,4'-diyl)bis{4-amino-3-[(E)-diazenyl] naphthalene-1-sulfonic acid}

1,1'-(3,3'-dipropyl[1,1'-biphenyl]-4,4'-diyl)bis{4-amino-3-[(E)-diazenyl]naphthalene-1-sulfonic acid}

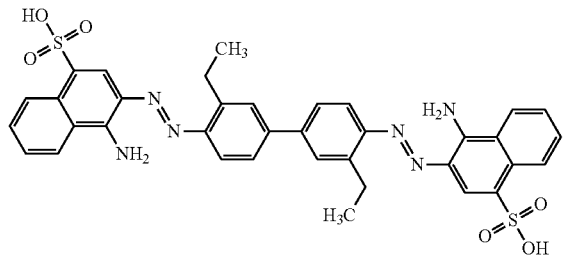 [SMILES: CCc1cc(-c2ccc(/N=N/c3cc(S(=O)(=O)O)c4ccccc4c3N)c(CC)c2)ccc1/N=N/c1cc(S(=O)(=O)O)c2ccccc2c1N]

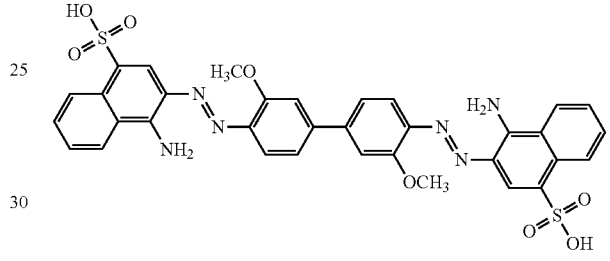

1,1'-(3,3'-diethy[1,1'-biphenyl]-4,4'-diyl)bis{4-amino-3-[(E)-diazenyl]naphthalene-1-sulfonic acid}

1,1'-(3,3'-dimethoxy[1,1'-biphenyl]-4,4'-diyl)bis{4-amino-3-[(E)-diazenyl] naphthalene-1-sulfonic acid}

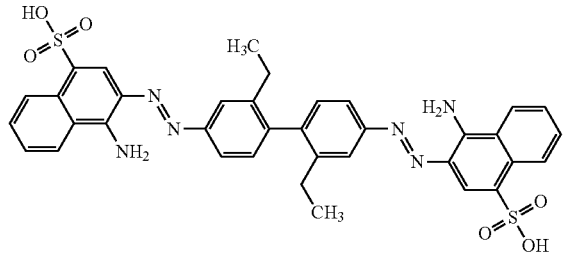 [SMILES: CCc1cc(/N=N/c2cc(S(=O)(=O)O)c3ccccc3c2N)ccc1-c1ccc(/N=N/c2cc(S(=O)(=O)O)c3ccccc3c2N)cc1CC]

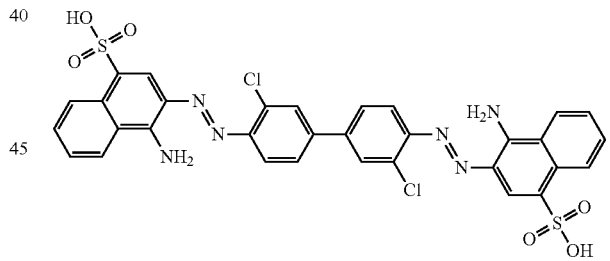

1,1'-(2,2'-diethy[1,1'-biphenyl]-4,4'-diyl)bis{4-amino-3-[(E)-diazenyl]naphthalene-1-sulfonic acid}

1,1'-(3,3'-dichloro[1,1'-biphenyl]-4,4'-diyl)bis{4-amino-3-[(E)-diazenyl]naphthalene-1-sulfonic acid}

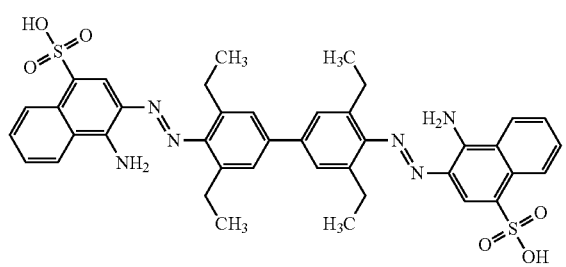 [SMILES: CCc1cc(-c2cc(CC)c(/N=N/c3cc(S(=O)(=O)O)c4ccccc4c3N)c(CC)c2)cc(CC)c1/N=N/c1cc(S(=O)(=O)O)c2ccccc2c1N]

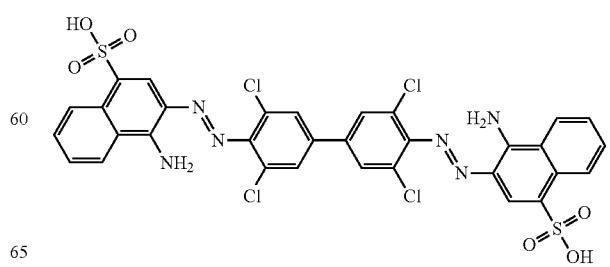

9

1,1'-(3,3',5,5'-tetrachloro[1,1'-biphenyl]-4,4'-diyl) bis{4-amino-3-[(E)-diazenyl] naphthalene-1-sulfonic acid}

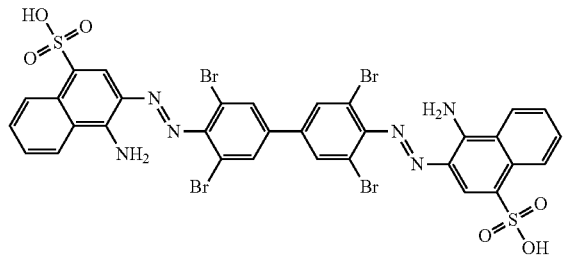 [SMILES: Nc1c(/N=N/c2c(Br)cc(-c3cc(Br)c(/N=N/c4cc(S(=O)(=O)O)c5ccccc5c4N)c(Br)c3)cc2Br)cc(S(=O)(=O)O)c2ccccc12]

1,1'-(3,3',5,5'-tetrabromo[1,1'-biphenyl]-4,4'-diyl) bis{4-amino-3-[(E)-diazenyl] naphthalene-1-sulfonic acid}

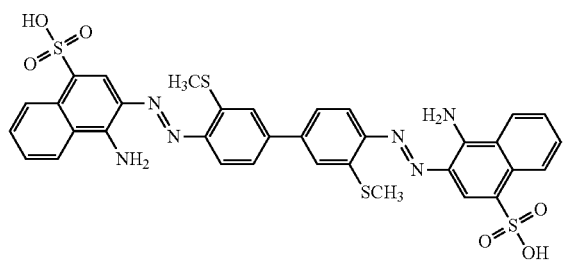

1,1'-(3,3'-dimethylthio[1,1'-biphenyl]-4,4'-diyl) bis{4-amino-3-[(E)-diazenyl] naphthalene-1-sulfonic acid}

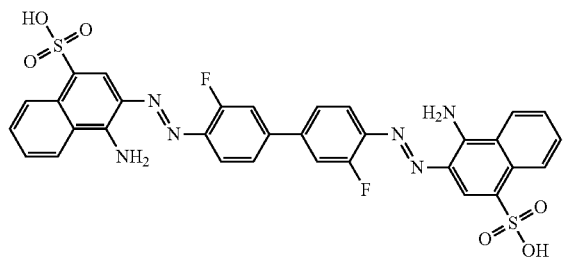 [SMILES: Nc1c(/N=N/c2ccc(-c3ccc(/N=N/c4cc(S(=O)(=O)O)c5ccccc5c4N)c(F)c3)cc2F)cc(S(=O)(=O)O)c2ccccc12]

1,1'-(3,3'-difluoro[1,1'-biphenyl]-4,4'-diyl)bis{4-amino-3-[(E)-diazenyl]naphthalene-1-sulfonic acid}

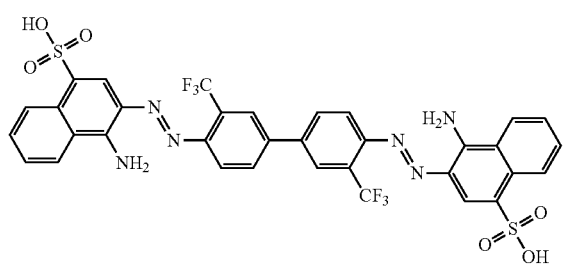 [SMILES: Nc1c(/N=N/c2ccc(-c3ccc(/N=N/c4cc(S(=O)(=O)O)c5ccccc5c4N)c(C(F)(F)F)c3)cc2C(F)(F)F)cc(S(=O)(=O)O)c2ccccc12]

10

1,1'-(3,3'-ditrifluoromethyl[1,1'-biphenyl]-4,4'-diyl) bis{4-amino-3-[(E)-diazenyl] naphthalene-1-sulfonic acid}

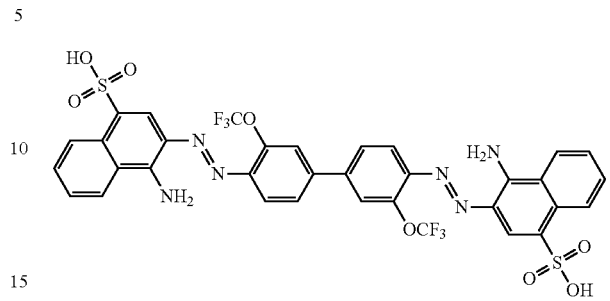

1,1'-(3,3'-ditrifluoromethoxy[1,1'-biphenyl]-4,4'-diyl)bis{4-amino-3-[(E)-diazenyl] naphthalene-1-sulfonic acid}

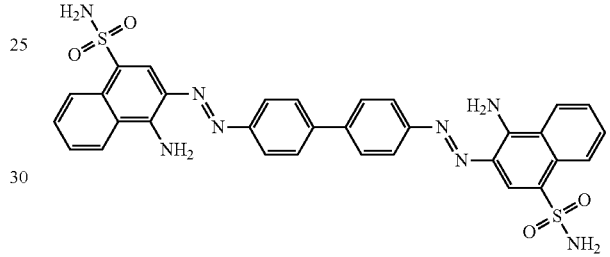

1,1'-([1,1'-biphenyl]-4,4'-diyl)bis{4-amino-3-[(E)-diazenyl]naphthalene-1-sulfonamide}

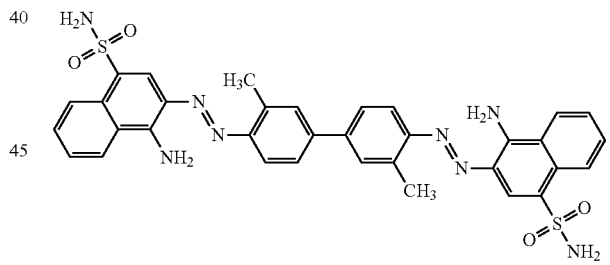

1,1'-(3,3'-dimethyl[1,1'-biphenyl]-4,4'-diyl)bis{4-amino-3-[(E)-diazenyl]naphthalene-1-sulfonamide}

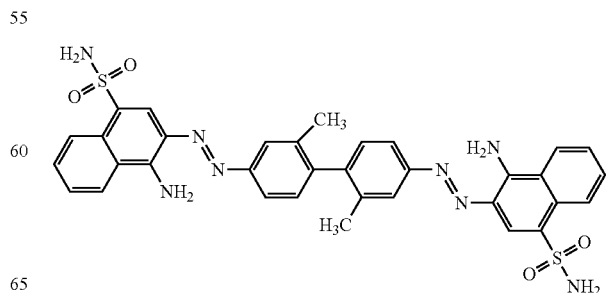

11

1,1'-(2,2'-dimethyl[1,1'-biphenyl]-4,4'-diyl)bis{4-amino-3-[(E)-diazenyl]naphthalene-1-sulfonamide}

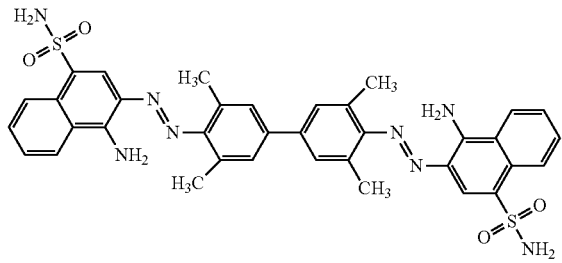 [SMILES: Cc1cc(-c2cc(C)c(/N=N/c3cc(S(N)(=O)=O)c4ccccc4c3N)c(C)c2)cc(C)c1/N=N/c1cc(S(N)(=O)=O)c2ccccc2c1N]

1,1'-(3,3',5,5'-tetramethyl[1,1'-biphenyl]-4,4'-diyl)bis{4-amino-3-[(E)-diazenyl] naphthalene-1-sulfonamide}

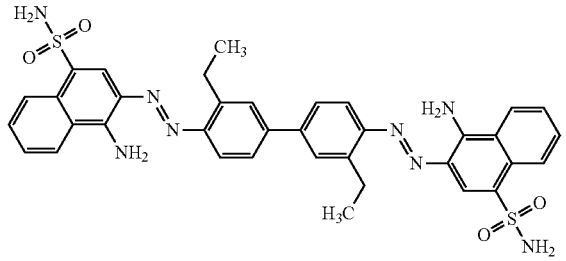 [SMILES: CCc1cc(-c2ccc(/N=N/c3cc(S(N)(=O)=O)c4ccccc4c3N)c(CC)c2)ccc1/N=N/c1cc(S(N)(=O)=O)c2ccccc2c1N]

1,1'-(3,3'-diethy[1,1'-biphenyl]-4,4'-diyl)bis{4-amino-3-[(E)-diazenyl]naphthalene-1-sulfonamide}

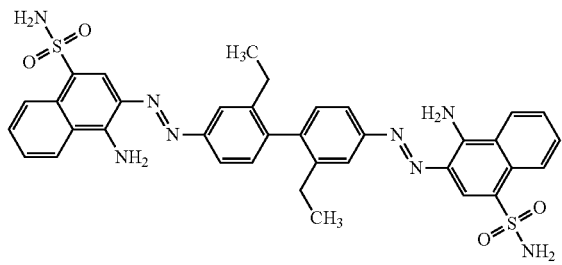 [SMILES: CCc1cc(/N=N/c2cc(S(N)(=O)=O)c3ccccc3c2N)ccc1-c1ccc(/N=N/c2cc(S(N)(=O)=O)c3ccccc3c2N)cc1CC]

1,1'-(2,2'-diethy[1,1'-biphenyl]-4,4'-diyl)bis{4-amino-3-[(E)-diazenyl]naphthalene-1-sulfonamide}

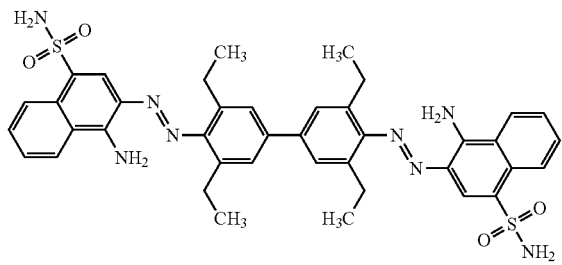 [SMILES: CCc1cc(-c2cc(CC)c(/N=N/c3cc(S(N)(=O)=O)c4ccccc4c3N)c(CC)c2)cc(CC)c1/N=N/c1cc(S(N)(=O)=O)c2ccccc2c1N]

12

1,1'-(3,3',5,5'-tetraethyl[1,1'-biphenyl]-4,4'-diyl)bis{4-amino-3-[(E)-diazenyl] naphthalene-1-sulfonamide}

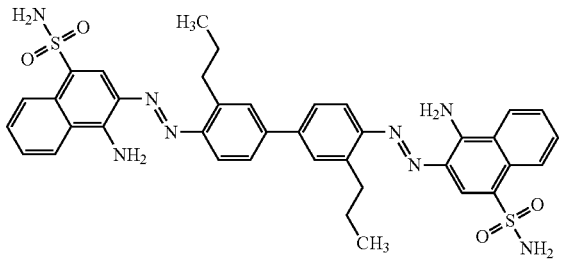 [SMILES: CCCc1cc(-c2ccc(/N=N/c3cc(S(N)(=O)=O)c4ccccc4c3N)c(CCC)c2)ccc1/N=N/c1cc(S(N)(=O)=O)c2ccccc2c1N]

1,1'-(3,3'-dipropyl[1,1'-biphenyl]-4,4'-diyl)bis{4-amino-3-[(E)-diazenyl]naphthalene-1-sulfonamide}

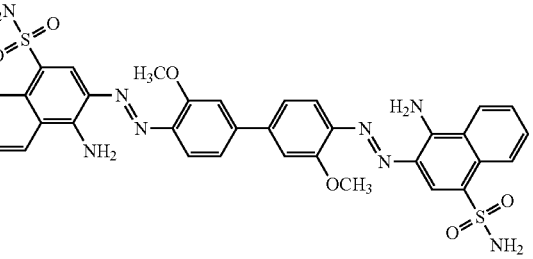

1,1'-(3,3'-dimethoxy[1,1'-biphenyl]-4,4'-diyl)bis{4-amino-3-[(E)-diazenyl] naphthalene-1-sulfonamide}

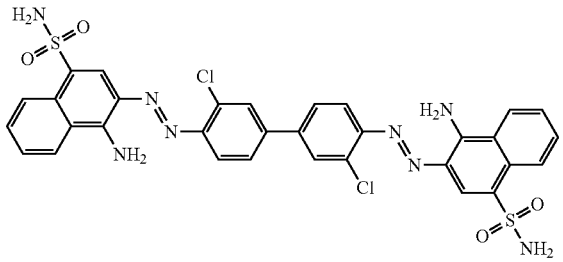 [SMILES: Nc1c(/N=N/c2ccc(-c3ccc(/N=N/c4cc(S(N)(=O)=O)c5ccccc5c4N)c(Cl)c3)cc2Cl)cc(S(N)(=O)=O)c2ccccc12]

1,1'-(3,3'-dichloro[1,1'-biphenyl]-4,4'-diyl)bis{4-amino-3-[(E)-diazenyl]naphthalene-1-sulfonamide}

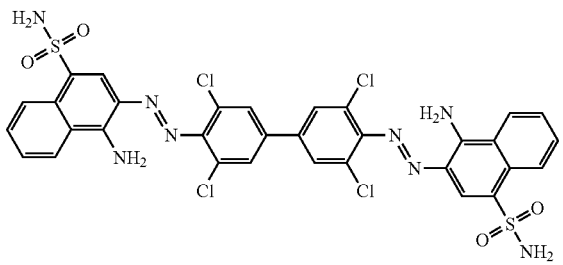

13

1,1'-(3,3',5,5'-tetrachloro[1,1'-biphenyl]-4,4'-diyl) bis{4-amino-3-[(E)-diazenyl] naphthalene-1-sulfonamide}

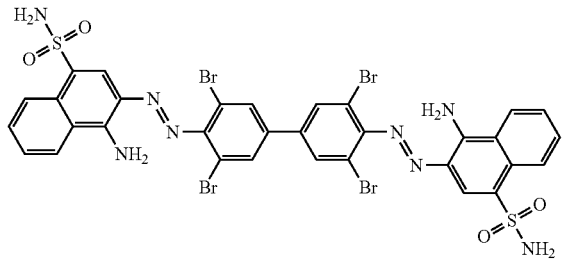 [SMILES: Nc1c(/N=N/c2c(Cl)cc(-c3cc(Cl)c(/N=N/c4cc(S(N)(=O)=O)c5ccccc5c4N)c(Cl)c3)cc2Cl)cc(S(N)(=O)=O)c2ccccc12]

1,1'-(3,3',5,5'-tetrabromo[1,1'-biphenyl]-4,4'-diyl) bis{4-amino-3-[(E)-diazenyl] naphthalene-1-sulfonamide}

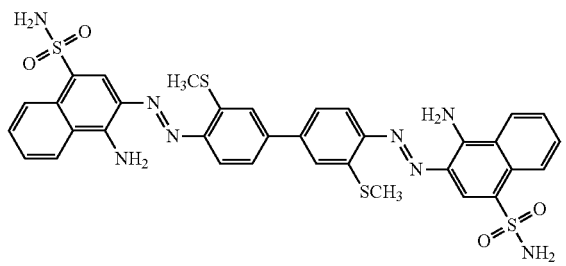

1,1'-(3,3'-dimethylthio[1,1'-biphenyl]-4,4'-diyl) bis{4-amino-3-[(E)-diazenyl] naphthalene-1-sulfonamide}

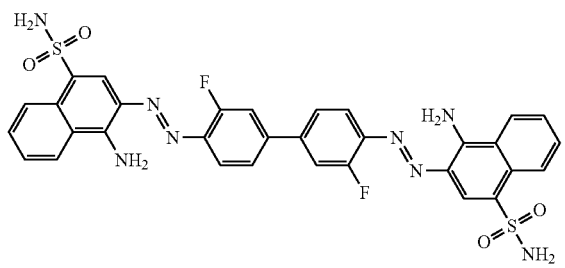 [SMILES: Nc1c(/N=N/c2ccc(-c3ccc(/N=N/c4cc(S(N)(=O)=O)c5ccccc5c4N)c(F)c3)cc2F)cc(S(N)(=O)=O)c2ccccc12]

1,1'-(3,3'-difluoro[1,1'-biphenyl]-4,4'-diyl)bis{4-amino-3-[(E)-diazenyl]naphthalene-1-sulfonamide}

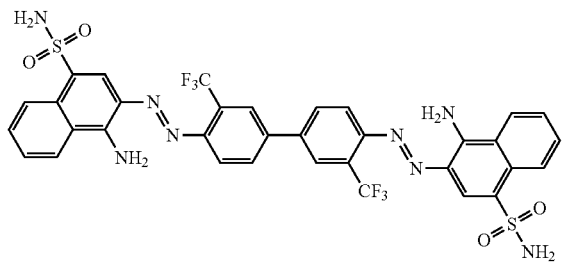 [SMILES: Nc1c(/N=N/c2ccc(-c3ccc(/N=N/c4cc(S(N)(=O)=O)c5ccccc5c4N)c(C(F)(F)F)c3)cc2C(F)(F)F)cc(S(N)(=O)=O)c2ccccc12]

14

1,1'-(3,3'-ditrifluoromethyl[1,1'-biphenyl]-4,4'-diyl) bis{4-amino-3-[(E)-diazenyl] naphthalene-1-sulfonamide}

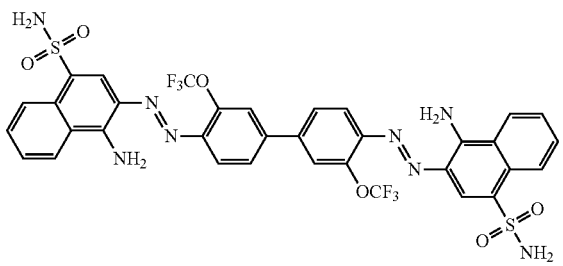 [SMILES: Nc1c(/N=N/c2ccc(-c3ccc(/N=N/c4cc(S(N)(=O)=O)c5ccccc5c4N)c(OC(F)(F)F)c3)cc2OC(F)(F)F)cc(S(N)(=O)=O)c2ccccc12]

1,1'-(3,3'-ditrifluoromethoxy[1,1'-biphenyl]-4,4'-diyl)bis{4-amino-3-[(E)-diazenyl] naphthalene-1-sulfonamide}

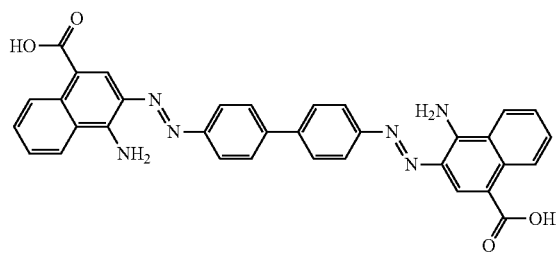 [SMILES: Nc1c(/N=N/c2ccc(-c3ccc(/N=N/c4cc(C(=O)O)c5ccccc5c4N)cc3)cc2)cc(C(=O)O)c2ccccc12]

1,1'-([1,1'-biphenyl]-4,4'-diyl)bis{4-amino-3-[(E)-diazenyl]naphthalene-1-carboxylic acid}

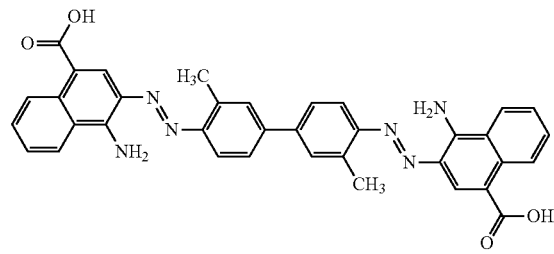 [SMILES: Cc1cc(-c2ccc(/N=N/c3cc(C(=O)O)c4ccccc4c3N)c(C)c2)ccc1/N=N/c1cc(C(=O)O)c2ccccc2c1N]

1,1'-(3,3'-dimethyl[1,1'-biphenyl]-4,4'-diyl)bis{4-amino-3-[(E)-diazenyl]naphthalene-1-carboxylic acid}

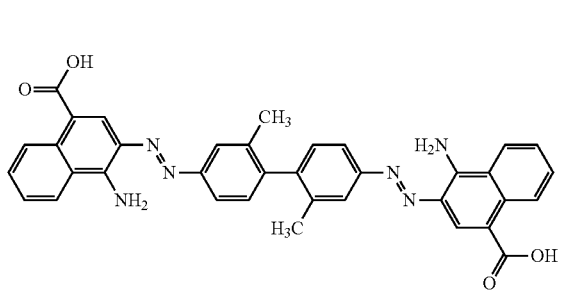 [SMILES: Cc1cc(/N=N/c2cc(C(=O)O)c3ccccc3c2N)ccc1-c1ccc(/N=N/c2cc(C(=O)O)c3ccccc3c2N)cc1C]

15

1,1'-(2,2'-dimethyl[1,1'-biphenyl]-4,4'-diyl)bis{4-amino-3-[(E)-diazenyl]naphthalene-1-carboxylic acid}

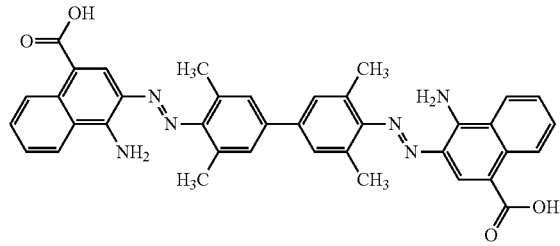 [SMILES: Cc1cc(-c2cc(C)c(/N=N/c3cc(C(=O)O)c4ccccc4c3N)c(C)c2)cc(C)c1/N=N/c1cc(C(=O)O)c2ccccc2c1N]

1,1'-(3,3',5,5'-tetramethyl[1,1'-biphenyl]-4,4'-diyl)bis{4-amino-3-[(E)-diazenyl] naphthalene-1-carboxylic acid}

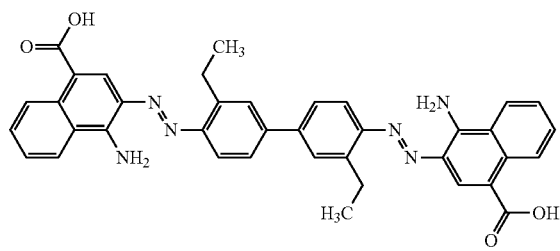 [SMILES: CCc1cc(-c2ccc(/N=N/c3cc(C(=O)O)c4ccccc4c3N)c(CC)c2)ccc1/N=N/c1cc(C(=O)O)c2ccccc2c1N]

1,1'-(3,3'-diethy[1,1'-biphenyl]-4,4'-diyl)bis{4-amino-3-[(E)-diazenyl]naphthalene-1-carboxylic acid}

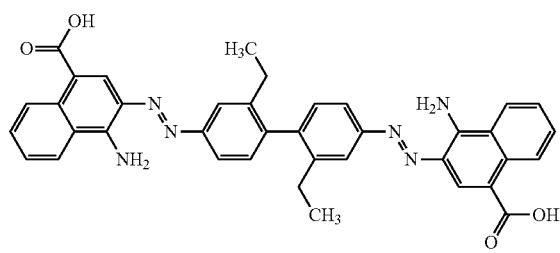 [SMILES: CCc1cc(/N=N/c2cc(C(=O)O)c3ccccc3c2N)ccc1-c1ccc(/N=N/c2cc(C(=O)O)c3ccccc3c2N)cc1CC]

1,1'-(2,2'-diethy[1,1'-biphenyl]-4,4'-diyl)bis{4-amino-3-[(E)-diazenyl]naphthalene-1-carboxylic acid}

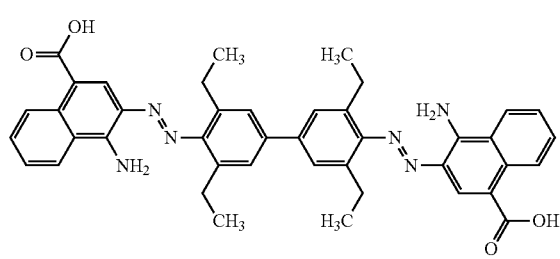 [SMILES: CCc1cc(-c2cc(CC)c(/N=N/c3cc(C(=O)O)c4ccccc4c3N)c(CC)c2)cc(CC)c1/N=N/c1cc(C(=O)O)c2ccccc2c1N]

16

1,1'-(3,3',5,5'-tetraethyl[1,1'-biphenyl]-4,4'-diyl)bis{4-amino-3-[(E)-diazenyl] naphthalene-1-carboxylic acid}

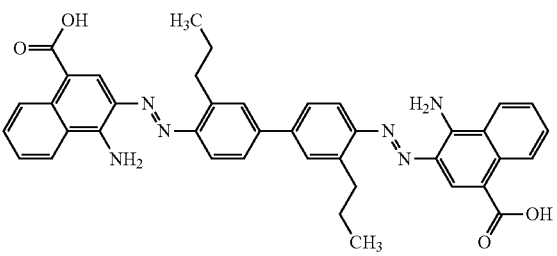 [SMILES: CCCc1cc(-c2ccc(/N=N/c3cc(C(=O)O)c4ccccc4c3N)c(CCC)c2)ccc1/N=N/c1cc(C(=O)O)c2ccccc2c1N]

1,1'-(3,3'-dipropyl[1,1'-biphenyl]-4,4'-diyl)bis{4-amino-3-[(E)-diazenyl]naphthalene-1-carboxylic acid}

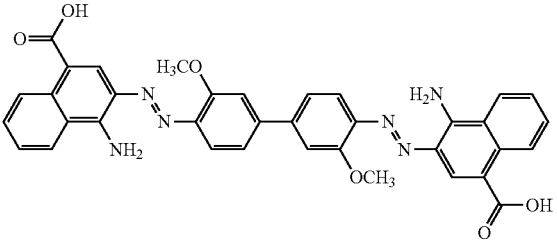

1,1'-(3,3'-dimethoxy[1,1'-biphenyl]-4,4'-diyl)bis{4-amino-3-[(E)-diazenyl] naphthalene-1-carboxylic acid}

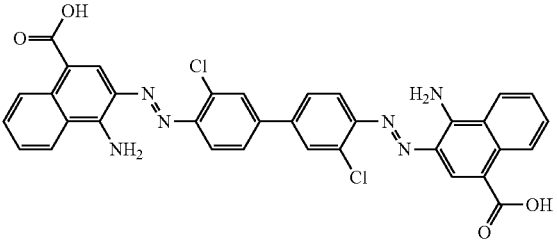 [SMILES: Nc1c(/N=N/c2ccc(-c3ccc(/N=N/c4cc(C(=O)O)c5ccccc5c4N)c(Cl)c3)cc2Cl)cc(C(=O)O)c2ccccc12]

1,1'-(3,3'-dichloro[1,1'-biphenyl]-4,4'-diyl)bis{4-amino-3-[(E)-diazenyl]naphthalene-1-carboxylic acid}

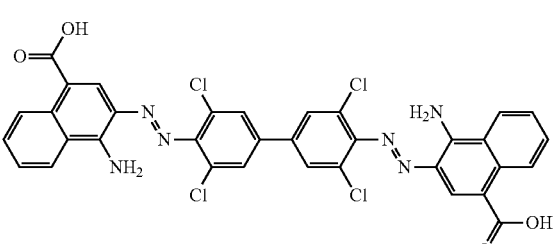

17

1,1'-(3,3',5,5'-tetrachloro[1,1'-biphenyl]-4,4'-diyl)
bis{4-amino-3-[(E)-diazenyl]naphthalene-1-carboxylic acid}

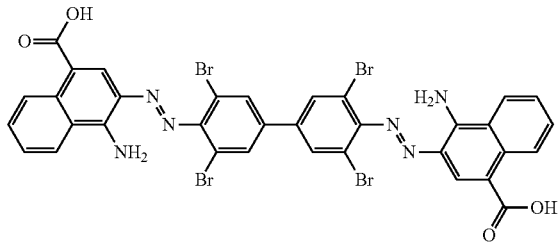 [SMILES: Nc1c(/N=N/c2c(Br)cc(-c3cc(Br)c(/N=N/c4cc(C(=O)O)c5ccccc5c4N)c(Br)c3)cc2Br)cc(C(=O)O)c2ccccc12]

1,1'-(3,3',5,5'-tetrabromo[1,1'-biphenyl]-4,4'-diyl)
bis{4-amino-3-[(E)-diazenyl] naphthalene-1-carboxylic acid}

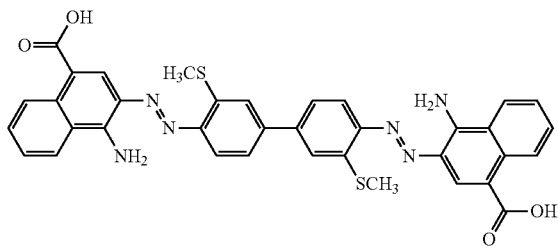

1,1'-(3,3'-dimethylthio[1,1'-biphenyl]-4,4'-diyl)
bis{4-amino-3-[(E)-diazenyl] naphthalene-1-carboxylic acid}

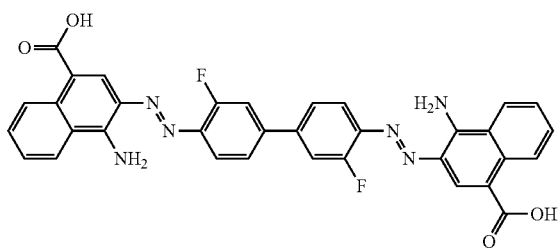 [SMILES: Nc1c(/N=N/c2ccc(-c3ccc(/N=N/c4cc(C(=O)O)c5ccccc5c4N)c(F)c3)cc2F)cc(C(=O)O)c2ccccc12]

1,1'-(3,3'-difluoro[1,1'-biphenyl]-4,4'-diyl)bis{4-amino-3-[(E)-diazenyl]naphthalene-1-carboxylic acid}

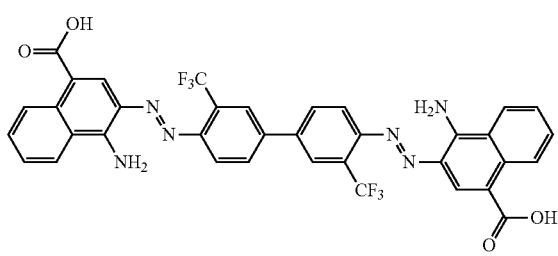 [SMILES: Nc1c(/N=N/c2ccc(-c3ccc(/N=N/c4cc(C(=O)O)c5ccccc5c4N)c(C(F)(F)F)c3)cc2C(F)(F)F)cc(C(=O)O)c2ccccc12]

18

1,1'-(3,3'-ditrifluoromethyl[1,1'-biphenyl]-4,4'-diyl)
bis{4-amino-3-[(E)-diazenyl] naphthalene-1-carboxylic acid}

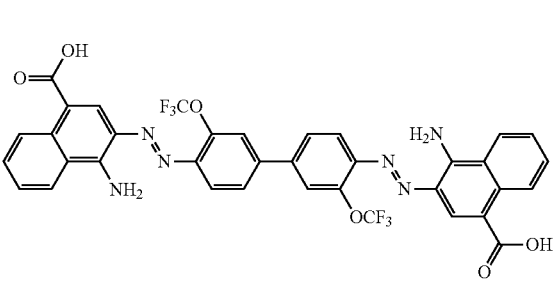 [SMILES: Nc1c(/N=N/c2ccc(-c3ccc(/N=N/c4cc(C(=O)O)c5ccccc5c4N)c(OC(F)(F)F)c3)cc2OC(F)(F)F)cc(C(=O)O)c2ccccc12]

1,1'-(3,3'-ditrifluoromethoxy[1,1'-biphenyl]-4,4'-diyl)bis{4-amino-3-[(E)-diazenyl]naphthalene-1-carboxylic acid}

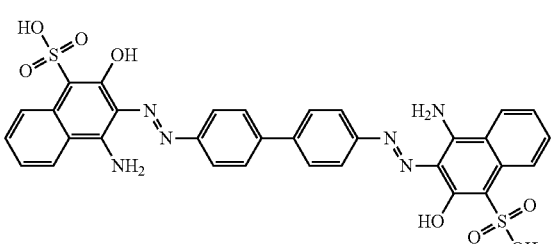

1,1'-([1,1'-biphenyl]-4,4'-diyl)bis{4-amino-2-hydroxy-3-[(E)-diazenyl]naphthalene-1-sulfonic acid}

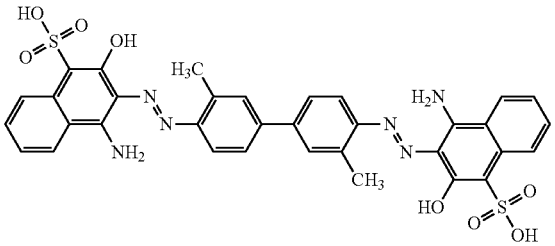

1,1'-(3,3'-dimethyl[1,1'-biphenyl]-4,4'-diyl)bis{4-amino-2-hydroxy-3-[(E)-diazenyl]naphthalene-1-sulfonic acid}

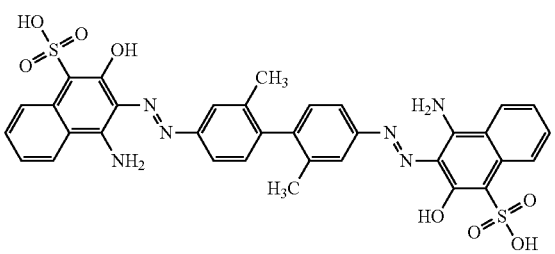 [SMILES: Cc1cc(/N=N/c2c(O)c(S(=O)(=O)O)c3ccccc3c2N)ccc1-c1ccc(/N=N/c2c(O)c(S(=O)(=O)O)c3ccccc3c2N)cc1C]

19

1,1'-(2,2'-dimethyl[1,1'-biphenyl]-4,4'-diyl)bis{4-amino-2-hydroxy-3-[(E)-diazenyl] naphthalene-1-sulfonic acid}

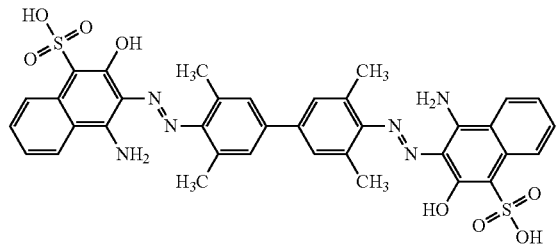

1,1'-(3,3',5,5'-tetramethyl[1,1'-biphenyl]-4,4'-diyl)bis{4-amino-2-hydroxy-3-[(E)-diazenyl]naphthalene-1-sulfonic acid}

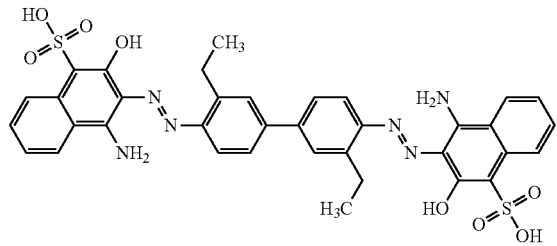 [SMILES: CCc1cc(-c2ccc(/N=N/c3c(O)c(S(=O)(=O)O)c4ccccc4c3N)c(CC)c2)ccc1/N=N/c1c(O)c(S(=O)(=O)O)c2ccccc2c1N]

1,1'-(3,3'-diethy[1,1'-biphenyl]-4,4'-diyl)bis{4-amino-2-hydroxy-3-[(E)-diazenyl] naphthalene-1-sulfonic acid}

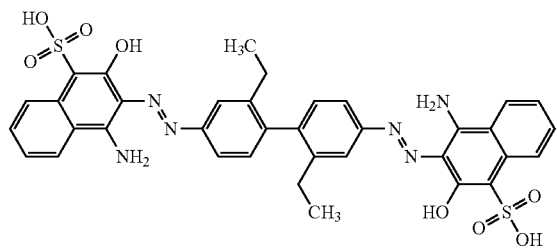 [SMILES: CCc1cc(/N=N/c2c(O)c(S(=O)(=O)O)c3ccccc3c2N)ccc1-c1ccc(/N=N/c2c(O)c(S(=O)(=O)O)c3ccccc3c2N)cc1CC]

1,1'-(2,2'-diethy[1,1'-biphenyl]-4,4'-diyl)bis{4-amino-2-hydroxy-3-[(E)-diazenyl] naphthalene-1-sulfonic acid}

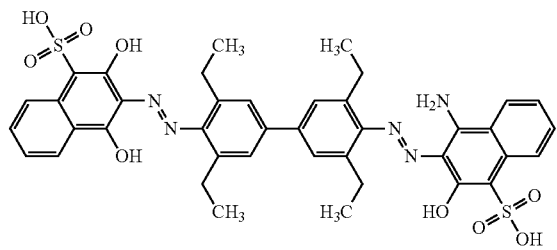 [SMILES: CCc1cc(-c2cc(CC)c(/N=N/c3c(O)c(S(=O)(=O)O)c4ccccc4c3O)c(CC)c2)cc(CC)c1/N=N/c1c(O)c(S(=O)(=O)O)c2ccccc2c1N]

20

1,1'-(3,3',5,5'-tetraethyl[1,1'-biphenyl]-4,4'-diyl)bis{4-amino-2-hydroxy-3-[(E)-diazenyl]naphthalene-1-sulfonic acid}

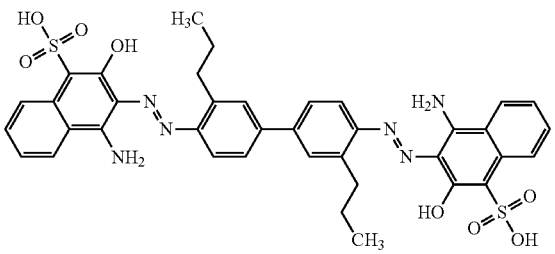 [SMILES: CCCc1cc(-c2ccc(/N=N/c3c(O)c(S(=O)(=O)O)c4ccccc4c3N)c(CCC)c2)ccc1/N=N/c1c(O)c(S(=O)(=O)O)c2ccccc2c1N]

1,1'-(3,3'-dipropyl[1,1'-biphenyl]-4,4'-diyl)bis{4-amino-2-hydroxy-3-[(E)-diazenyl]naphthalene-1-sulfonic acid}

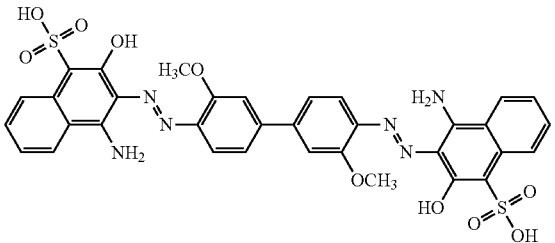

1,1'-(3,3'-dimethoxy[1,1'-biphenyl]-4,4'-diyl)bis{4-amino-2-hydroxy-3-[(E)-diazenyl]naphthalene-1-sulfonic acid}

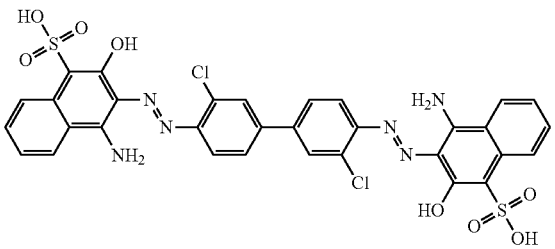

1,1'-(3,3'-dichloro[1,1'-biphenyl]-4,4'-diyl)bis{4-amino-2-hydroxy-3-[(E)-diazenyl] naphthalene-1-sulfonic acid}

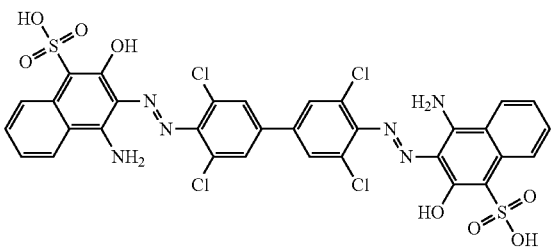 [SMILES: Nc1c(/N=N/c2c(Cl)cc(-c3cc(Cl)c(/N=N/c4c(O)c(S(=O)(=O)O)c5ccccc5c4N)c(Cl)c3)cc2Cl)c(O)c(S(=O)(=O)O)c2ccccc12]

21

1,1'-(3,3',5,5'-tetrachloro[1,1'-biphenyl]-4,4'-diyl)
bis{4-amino-2-hydroxy-3-[(E)-diazenyl]naphtha-
lene-1-sulfonic acid}

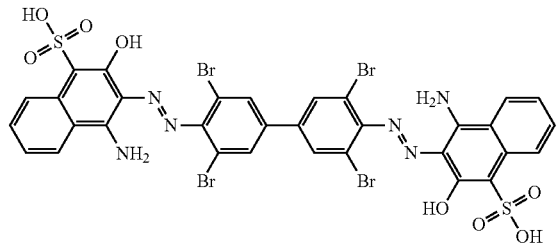 [SMILES: Nc1c(/N=N/c2c(Br)cc(-c3cc(Br)c(/N=N/c4c(O)c(S(=O)(=O)O)c5ccccc5c4N)c(Br)c3)cc2Br)c(O)c(S(=O)(=O)O)c2ccccc12]

1,1'-(3,3',5,5'-tetrabromo[1,1'-biphenyl]-4,4'-diyl)
bis{4-amino-2-hydroxy-3-[(E)-diazenyl]naphtha-
lene-1-sulfonic acid}

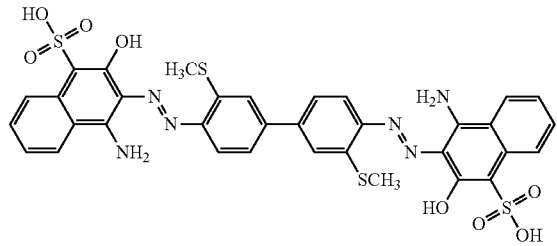

1,1'-(3,3'-dimethylthio[1,1'-biphenyl]-4,4'-diyl)
bis{4-amino-2-hydroxy-3-[(E)-diazenyl]naphtha-
lene-1-sulfonic acid}

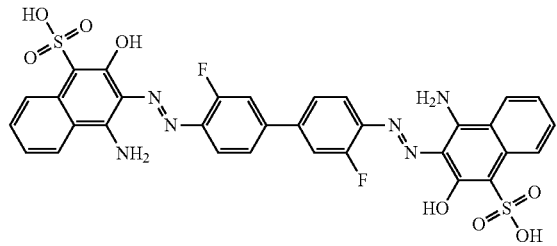

1,1'-(3,3'-difluoro[1,1'-biphenyl]-4,4'-diyl)bis{4-
amino-2-hydroxy-3-[(E)-diazenyl]naphthalene-1-
sulfonic acid}

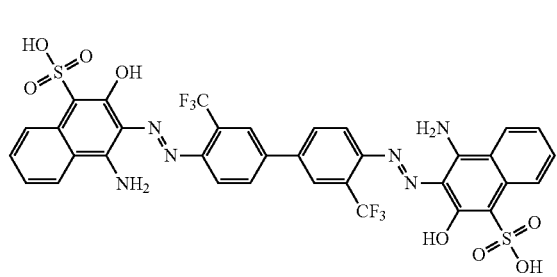 [SMILES: Nc1c(/N=N/c2ccc(-c3ccc(/N=N/c4c(O)c(S(=O)(=O)O)c5ccccc5c4N)c(C(F)(F)F)c3)cc2C(F)(F)F)c(O)c(S(=O)(=O)O)c2ccccc12]

22

1,1'-(3,3'-ditrifluoromethyl[1,1'-biphenyl]-4,4'-diyl)
bis{4-amino-2-hydroxy-3-[(E)-diazenyl]naphtha-
lene-1-sulfonic acid}

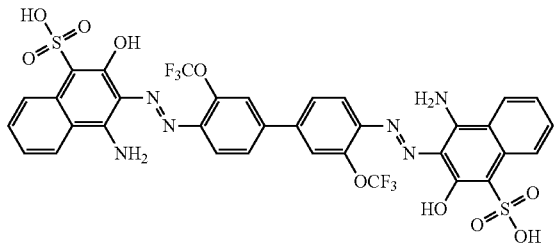 [SMILES: Nc1c(/N=N/c2ccc(-c3ccc(/N=N/c4c(O)c(S(=O)(=O)O)c5ccccc5c4N)c(OC(F)(F)F)c3)cc2OC(F)(F)F)c(O)c(S(=O)(=O)O)c2ccccc12]

1,1'-(3,3'-ditrifluoromethoxy[1,1'-biphenyl]-4,4'-
diyl)bis{4-amino-2-hydroxy-3-[(E)-diazenyl]naph-
thalene-1-sulfonic acid}

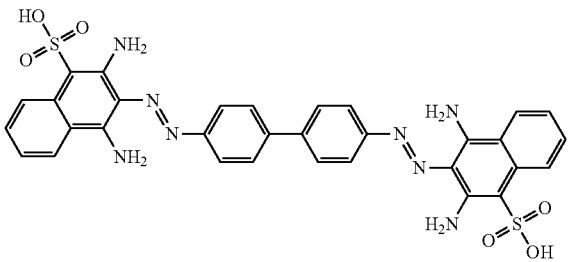 [SMILES: Nc1c(/N=N/c2ccc(-c3ccc(/N=N/c4c(N)c(S(=O)(=O)O)c5ccccc5c4N)cc3)cc2)c(N)c2ccccc2c1S(=O)(=O)O]

1,1'-([1,1'-biphenyl]-4,4'-diyl)bis{2,4-diamino-3-
[(E)-diazenyl]naphthalene-1-sulfonic acid}

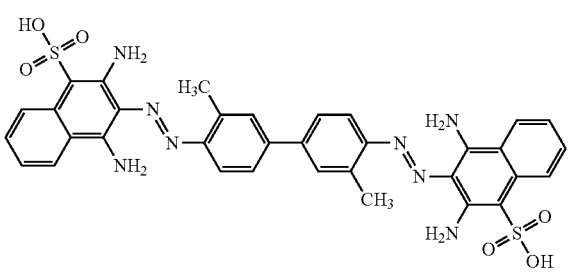

1,1'-(3,3'-dimethyl[1,1'-biphenyl]-4,4'-diyl)bis{2,4-
diamino-3-[(E)-diazenyl]naphthalene-1-sulfonic
acid}

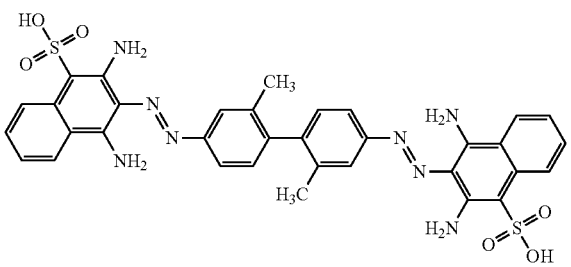 [SMILES: Cc1cc(/N=N/c2c(N)c(S(=O)(=O)O)c3ccccc3c2N)ccc1-c1ccc(/N=N/c2c(N)c(S(=O)(=O)O)c3ccccc3c2N)cc1C]

23

1,1'-(2,2'-dimethyl[1,1'-biphenyl]-4,4'-diyl)bis{2,4-diamino-3-[(E)-diazenyl] naphthalene-1-sulfonic acid}

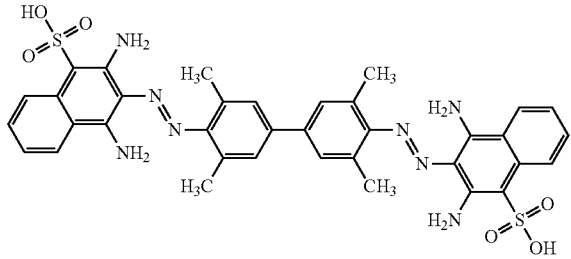 [SMILES: Cc1cc(-c2cc(C)c(/N=N/c3c(N)c(S(=O)(=O)O)c4ccccc4c3N)c(C)c2)cc(C)c1/N=N/c1c(N)c(S(=O)(=O)O)c2ccccc2c1N]

1,1'-(3,3',5,5'-tetramethyl[1,1'-biphenyl]-4,4'-diyl) bis{2,4-diamino-3-[(E)-diazenyl]naphthalene-1-sulfonic acid}

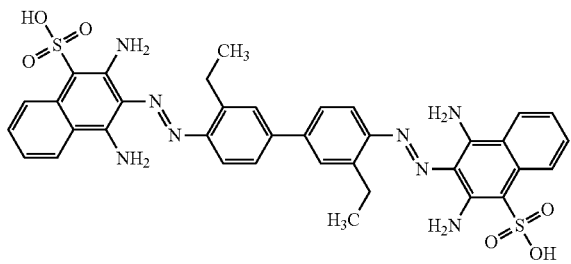 [SMILES: CCc1cc(-c2ccc(/N=N/c3c(N)c(S(=O)(=O)O)c4ccccc4c3N)c(CC)c2)ccc1/N=N/c1c(N)c(S(=O)(=O)O)c2ccccc2c1N]

1,1'-(3,3'-diethy[1,1'-biphenyl]-4,4'-diyl)bis{2,4-diamino-3-[(E)-diazenyl] naphthalene-1-sulfonic acid}

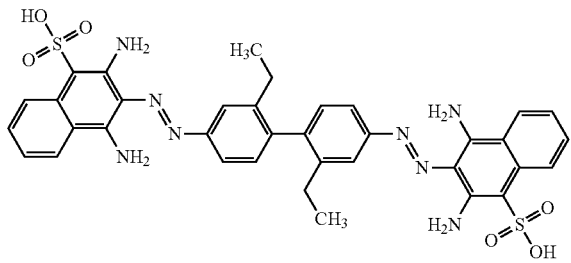 [SMILES: CCc1cc(/N=N/c2c(N)c(S(=O)(=O)O)c3ccccc3c2N)ccc1-c1ccc(/N=N/c2c(N)c(S(=O)(=O)O)c3ccccc3c2N)cc1CC]

1,1'-(2,2'-diethy[1,1'-biphenyl]-4,4'-diyl)bis{2,4-diamino-3-[(E)-diazenyl] naphthalene-1-sulfonic acid}

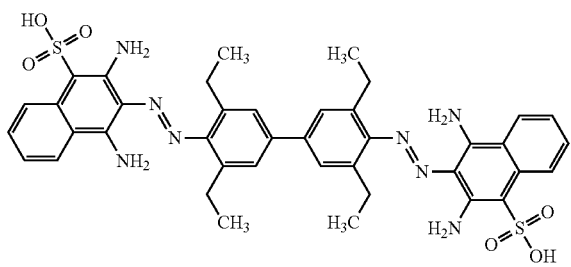 [SMILES: CCc1cc(-c2cc(CC)c(/N=N/c3c(N)c(S(=O)(=O)O)c4ccccc4c3N)c(CC)c2)cc(CC)c1/N=N/c1c(N)c(S(=O)(=O)O)c2ccccc2c1N]

24

1,1'-(3,3',5,5'-tetraethyl[1,1'-biphenyl]-4,4'-diyl) bis{2,4-diamino-3-[(E)-diazenyl]naphthalene-1-sulfonic acid}

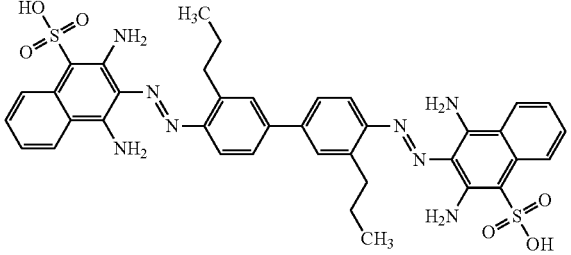 [SMILES: CCCc1cc(-c2ccc(/N=N/c3c(N)c(S(=O)(=O)O)c4ccccc4c3N)c(CCC)c2)ccc1/N=N/c1c(N)c(S(=O)(=O)O)c2ccccc2c1N]

1,1'-(3,3'-dipropyl[1,1'-biphenyl]-4,4'-diyl)bis{2,4-diamino-3-[(E)-diazenyl] naphthalene-1-sulfonic acid}

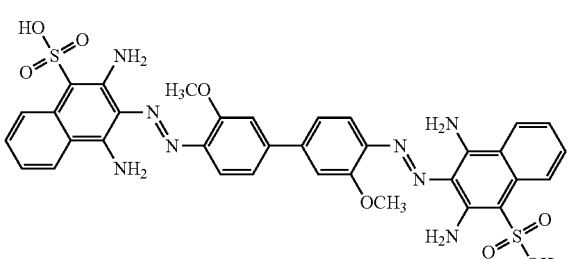

1,1'-(3,3'-dimethoxy[1,1'-biphenyl]-4,4'-diyl)bis{2,4-diamino-3-[(E)-diazenyl] naphthalene-1-sulfonic acid}

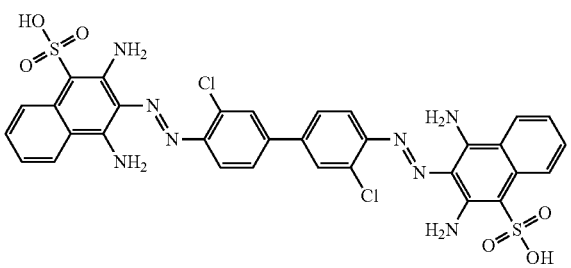 [SMILES: Nc1c(/N=N/c2ccc(-c3ccc(/N=N/c4c(N)c(S(=O)(=O)O)c5ccccc5c4N)c(Cl)c3)cc2Cl)c(N)c2ccccc2c1S(=O)(=O)O]

1,1'-(3,3'-dichloro[1,1'-biphenyl]-4,4'-diyl)bis{2,4-diamino-3-[(E)-diazenyl] naphthalene-1-sulfonic acid}

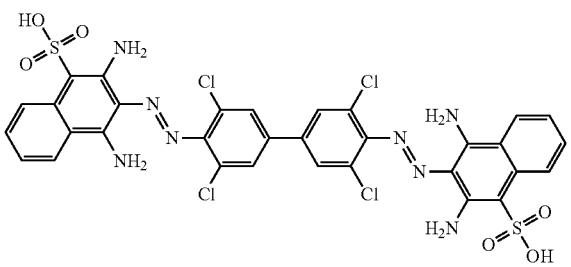 [SMILES: Nc1c(/N=N/c2c(Cl)cc(-c3cc(Cl)c(/N=N/c4c(N)c(S(=O)(=O)O)c5ccccc5c4N)c(Cl)c3)cc2Cl)c(N)c2ccccc2c1S(=O)(=O)O]

25

1,1'-(3,3',5,5'-tetrachloro[1,1'-biphenyl]-4,4'-diyl) bis{2,4-diamino-3-[(E)-diazenyl] naphthalene-1-sulfonic acid}

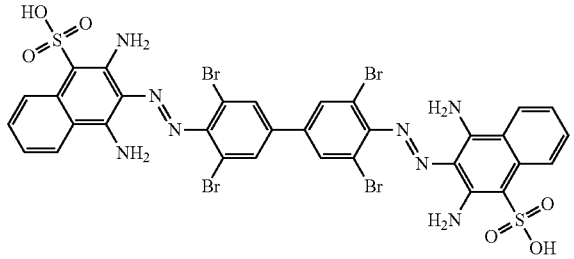 [SMILES: Nc1c(/N=N/c2c(Br)cc(-c3cc(Br)c(/N=N/c4c(N)c(S(=O)(=O)O)c5ccccc5c4N)c(Br)c3)cc2Br)c(N)c2ccccc2c1S(=O)(=O)O]

1,1'-(3,3',5,5'-tetrabromo[1,1'-biphenyl]-4,4'-diyl) bis{2,4-diamino-3-[(E)-diazenyl]naphthalene-1-sulfonic acid}

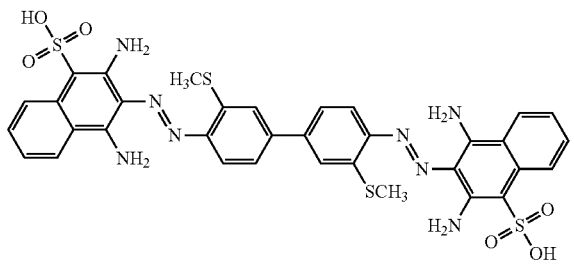

1,1'-(3,3'-dimethylthio[1,1'-biphenyl]-4,4'-diyl)bis{2,4-diamino-3-[(E)-diazenyl] naphthalene-1-sulfonic acid}

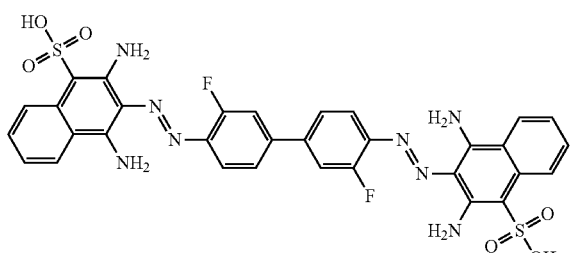

1,1'-(3,3'-difluoro[1,1'-biphenyl]-4,4'-diyl)bis{2,4-diamino-3-[(E)-diazenyl] naphthalene-1-sulfonic acid}

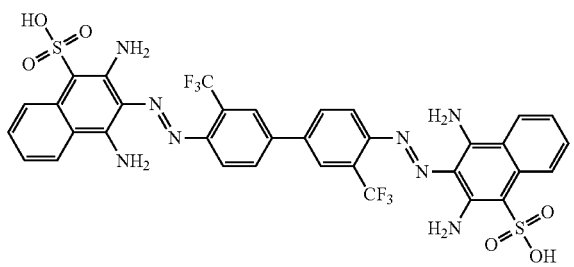 [SMILES: Nc1c(/N=N/c2ccc(-c3ccc(/N=N/c4c(N)c(S(=O)(=O)O)c5ccccc5c4N)c(C(F)(F)F)c3)cc2C(F)(F)F)c(N)c2ccccc2c1S(=O)(=O)O]

26

1,1'-(3,3'-ditrifluoromethyl[1,1'-biphenyl]-4,4'-diyl) bis{2,4-diamino-3-[(E)-diazenyl]naphthalene-1-sulfonic acid}

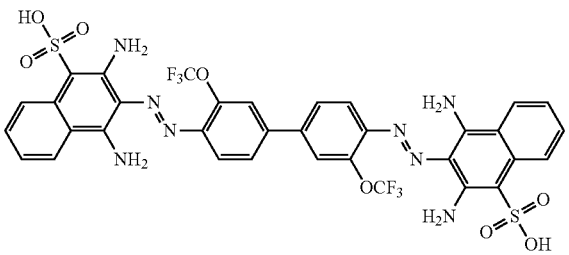 [SMILES: Nc1c(/N=N/c2ccc(-c3ccc(/N=N/c4c(N)c(S(=O)(=O)O)c5ccccc5c4N)c(OC(F)(F)F)c3)cc2OC(F)(F)F)c(N)c2ccccc2c1S(=O)(=O)O]

1,1'-(3,3'-ditrifluoromethoxy[1,1'-biphenyl]-4,4'-diyl)bis{2,4-diamino-3-[(E)-diazenyl] naphthalene-1-sulfonic acid}

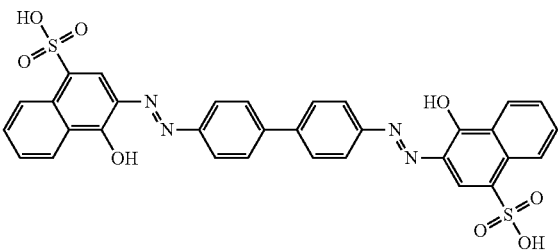 [SMILES: O=S(=O)(O)c1cc(/N=N/c2ccc(-c3ccc(/N=N/c4cc(S(=O)(=O)O)c5ccccc5c4O)cc3)cc2)c(O)c2ccccc12]

1,1'-([1,1'-biphenyl]-4,4'-diyl)bis{4-hydroxy-3-[(E)-diazenyl]naphthalene-1-sulfonic acid}

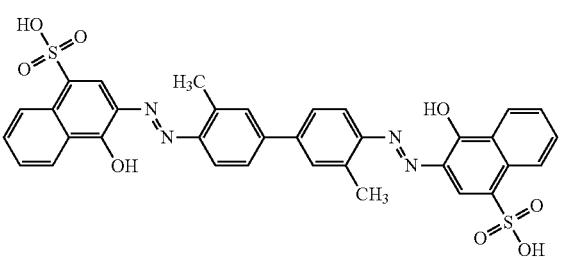 [SMILES: Cc1cc(-c2ccc(/N=N/c3cc(S(=O)(=O)O)c4ccccc4c3O)c(C)c2)ccc1/N=N/c1cc(S(=O)(=O)O)c2ccccc2c1O]

1,1'-(3,3'-dimethyl[1,1'-biphenyl]-4,4'-diyl)bis{4-hydroxy-3-[(E)-diazenyl] naphthalene-1-sulfonic acid}

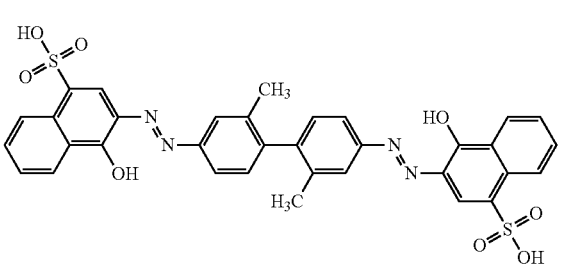 [SMILES: Cc1cc(/N=N/c2cc(S(=O)(=O)O)c3ccccc3c2O)ccc1-c1ccc(/N=N/c2cc(S(=O)(=O)O)c3ccccc3c2O)cc1C]

27

1,1'-(2,2'-dimethyl[1,1'-biphenyl]-4,4'-diyl)bis{4-hydroxy-3-[(E)-diazenyl] naphthalene-1-sulfonic acid}

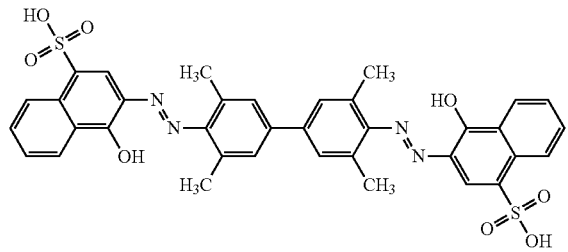 [SMILES: Cc1cc(-c2cc(C)c(/N=N/c3cc(S(=O)(=O)O)c4ccccc4c3O)c(C)c2)cc(C)c1/N=N/c1cc(S(=O)(=O)O)c2ccccc2c1O]

1,1'-(3,3',5,5'-tetramethyl[1,1'-biphenyl]-4,4'-diyl)bis{4-hydroxy-3-[(E)-diazenyl] naphthalene-1-sulfonic acid}

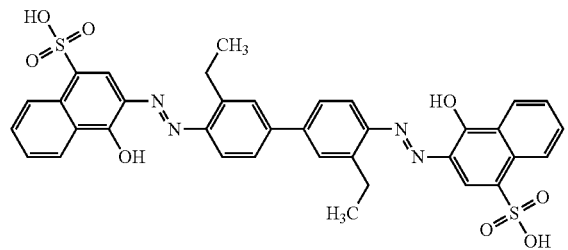 [SMILES: CCc1cc(-c2ccc(/N=N/c3cc(S(=O)(=O)O)c4ccccc4c3O)c(CC)c2)ccc1/N=N/c1cc(S(=O)(=O)O)c2ccccc2c1O]

1,1'-(3,3'-diethy[1,1'-biphenyl]-4,4'-diyl)bis{4-hydroxy-3-[(E)-diazenyl]naphthalene-1-sulfonic acid}

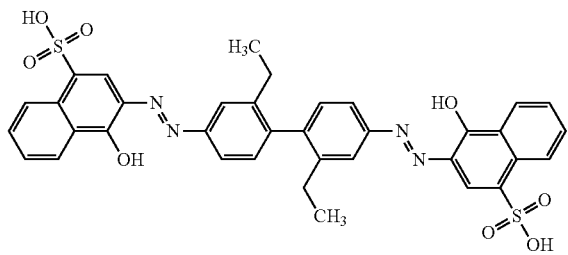 [SMILES: CCc1cc(/N=N/c2cc(S(=O)(=O)O)c3ccccc3c2O)ccc1-c1ccc(/N=N/c2cc(S(=O)(=O)O)c3ccccc3c2O)cc1CC]

1,1'-(2,2'-diethy[1,1'-biphenyl]-4,4'-diyl)bis{4-hydroxy-3-[(E)-diazenyl]naphthalene-1-sulfonic acid}

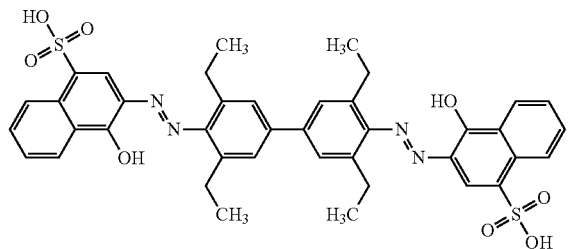 [SMILES: CCc1cc(-c2cc(CC)c(/N=N/c3cc(S(=O)(=O)O)c4ccccc4c3O)c(CC)c2)cc(CC)c1/N=N/c1cc(S(=O)(=O)O)c2ccccc2c1O]

28

1,1'-(3,3',5,5'-tetraethyl[1,1'-biphenyl]-4,4'-diyl)bis{4-hydroxy-3-[(E)-diazenyl] naphthalene-1-sulfonic acid}

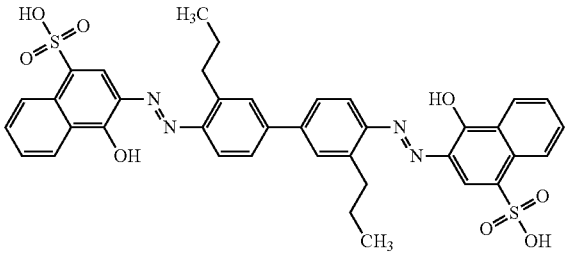 [SMILES: CCCc1cc(-c2ccc(/N=N/c3cc(S(=O)(=O)O)c4ccccc4c3O)c(CCC)c2)ccc1/N=N/c1cc(S(=O)(=O)O)c2ccccc2c1O]

1,1'-(3,3'-dipropyl[1,1'-biphenyl]-4,4'-diyl)bis{4-hydroxy-3-[(E)-diazenyl] naphthalene-1-sulfonic acid}

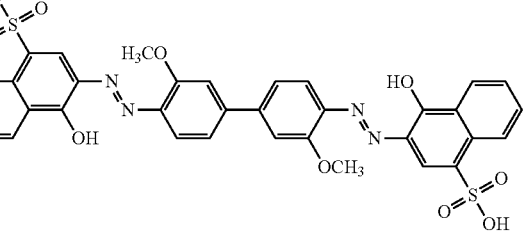

1,1'-(3,3'-dimethoxy[1,1'-biphenyl]-4,4'-diyl)bis{4-hydroxy-3-[(E)-diazenyl] naphthalene-1-sulfonic acid}

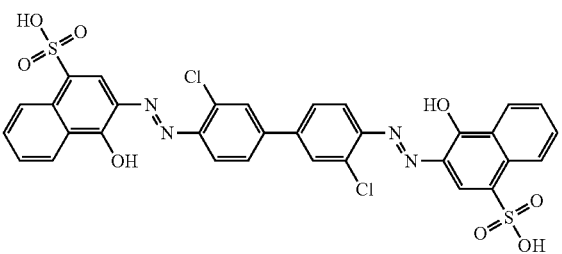 [SMILES: O=S(=O)(O)c1cc(/N=N/c2ccc(-c3ccc(/N=N/c4cc(S(=O)(=O)O)c5ccccc5c4O)c(Cl)c3)cc2Cl)c(O)c2ccccc12]

1,1'-(3,3'-dichloro[1,1'-biphenyl]-4,4'-diyl)bis{4-hydroxy-3-[(E)-diazenyl] naphthalene-1-sulfonic acid}

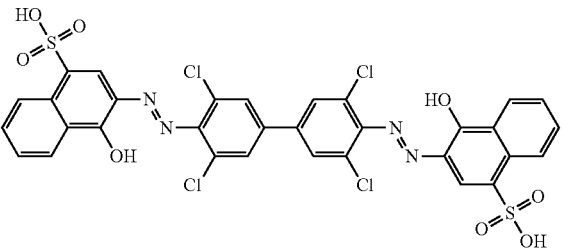

29

1,1'-(3,3',5,5'-tetrachloro[1,1'-biphenyl]-4,4'-diyl) bis{4-hydroxy-3-[(E)-diazenyl] naphthalene-1-sulfonic acid}

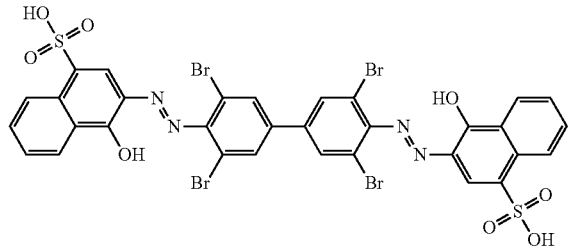 [SMILES: O=S(=O)(O)c1cc(/N=N/c2c(Br)cc(-c3cc(Br)c(/N=N/c4cc(S(=O)(=O)O)c5ccccc5c4O)c(Br)c3)cc2Br)c(O)c2ccccc12]

1,1'-(3,3',5,5'-tetrabromo[1,1'-biphenyl]-4,4'-diyl) bis{4-hydroxy-3-[(E)-diazenyl] naphthalene-1-sulfonic acid}

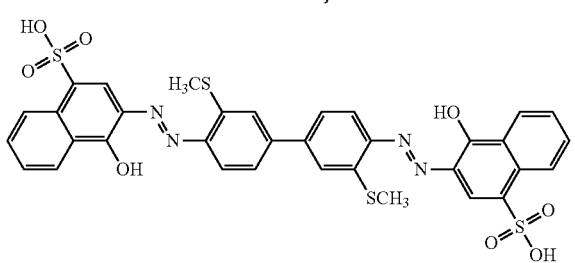

1,1'-(3,3'-dimethylthio[1,1'-biphenyl]-4,4'-diyl) bis{4-hydroxy-3-[(E)-diazenyl] naphthalene-1-sulfonic acid}

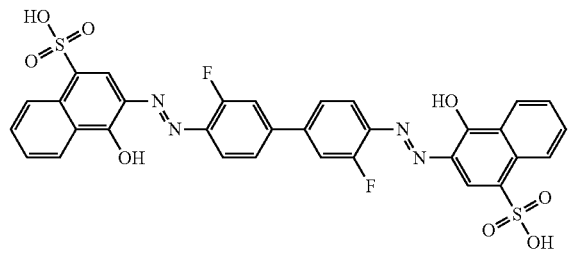 [SMILES: O=S(=O)(O)c1cc(/N=N/c2ccc(-c3ccc(/N=N/c4cc(S(=O)(=O)O)c5ccccc5c4O)c(F)c3)cc2F)c(O)c2ccccc12]

1,1'-(3,3'-difluoro[1,1'-biphenyl]-4,4'-diyl)bis{4-hydroxy-3-[(E)-diazenyl] naphthalene-1-sulfonic acid}

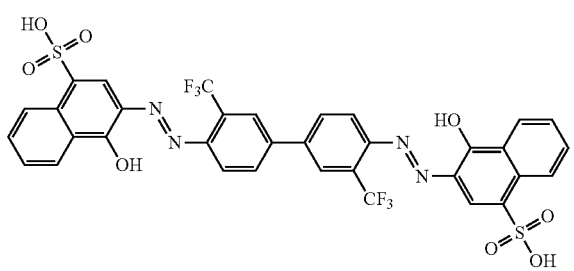 [SMILES: O=S(=O)(O)c1cc(/N=N/c2ccc(-c3ccc(/N=N/c4cc(S(=O)(=O)O)c5ccccc5c4O)c(C(F)(F)F)c3)cc2C(F)(F)F)c(O)c2ccccc12]

30

1,1'-(3,3'-ditrifluoromethyl[1,1'-biphenyl]-4,4'-diyl) bis{4-hydroxy-3-[(E)-diazenyl]naphthalene-1-sulfonic acid}

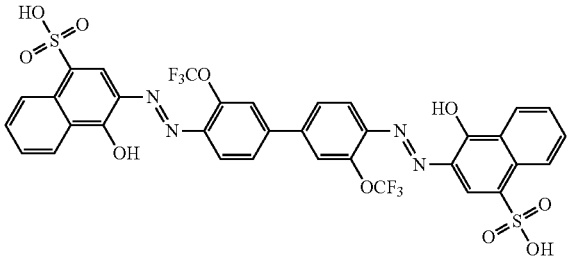

1,1'-(3,3'-ditrifluoromethoxy[1,1'-biphenyl]-4,4'-diyl)bis{4-hydroxy-3-[(E)-diazenyl]naphthalene-1-sulfonic acid}

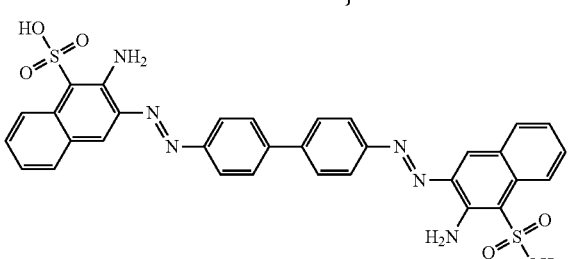

1,1'-([1,1'-biphenyl]-4,4'-diyl)bis{2-amino-3-[(E)-diazenyl]naphthalene-1-sulfonic acid}

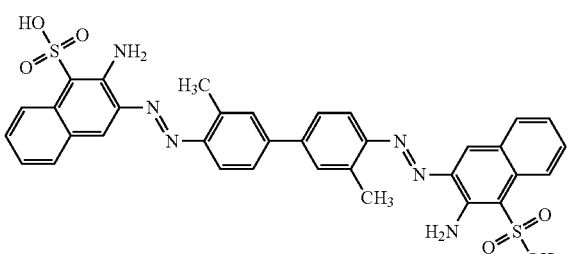

1,1'-(3,3'-dimethyl[1,1'-biphenyl]-4,4'-diyl)bis{2-amino-3-[(E)-diazenyl]naphthalene-1-sulfonic acid}

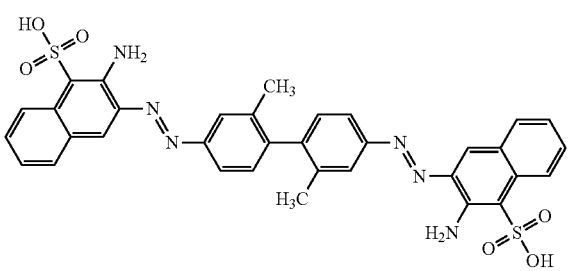 [SMILES: Cc1cc(/N=N/c2cc3ccccc3c(S(=O)(=O)O)c2N)ccc1-c1ccc(/N=N/c2cc3ccccc3c(S(=O)(=O)O)c2N)cc1C]

31

1,1'-(2,2'-dimethyl[1,1'-biphenyl]-4,4'-diyl)bis{2-amino-3-[(E)-diazenyl]naphthalene-1-sulfonic acid}

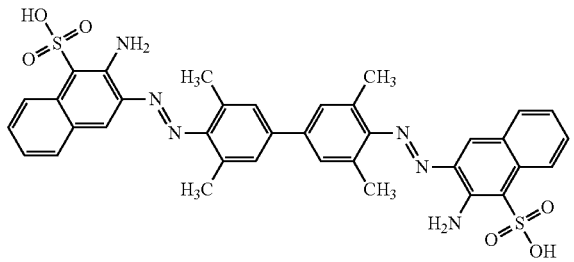 [SMILES: Cc1cc(-c2cc(C)c(/N=N/c3cc4ccccc4c(S(=O)(=O)O)c3N)c(C)c2)cc(C)c1/N=N/c1cc2ccccc2c(S(=O)(=O)O)c1N]

1,1'-(3,3',5,5'-tetramethyl[1,1'-biphenyl]-4,4'-diyl)bis{2-amino-3-[(E)-diazenyl] naphthalene-1-sulfonic acid}

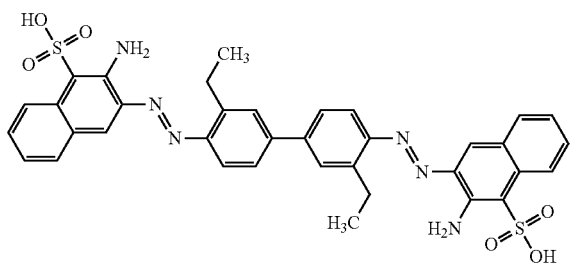 [SMILES: CCc1cc(-c2ccc(/N=N/c3cc4ccccc4c(S(=O)(=O)O)c3N)c(CC)c2)ccc1/N=N/c1cc2ccccc2c(S(=O)(=O)O)c1N]

1,1'-(3,3'-diethy[1,1'-biphenyl]-4,4'-diyl)bis{2-amino-3-[(E)-diazenyl]naphthalene-1-sulfonic acid}

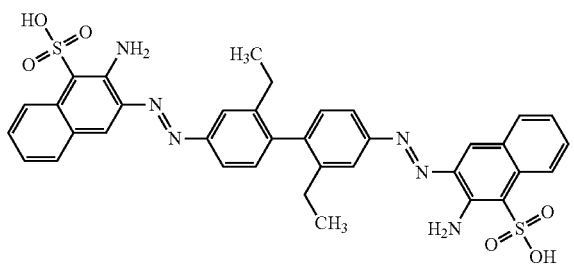 [SMILES: CCc1cc(/N=N/c2cc3ccccc3c(S(=O)(=O)O)c2N)ccc1-c1ccc(/N=N/c2cc3ccccc3c(S(=O)(=O)O)c2N)cc1CC]

1,1'-(2,2'-diethy[1,1'-biphenyl]-4,4'-diyl)bis{2-amino-3-[(E)-diazenyl]naphthalene-1-sulfonic acid}

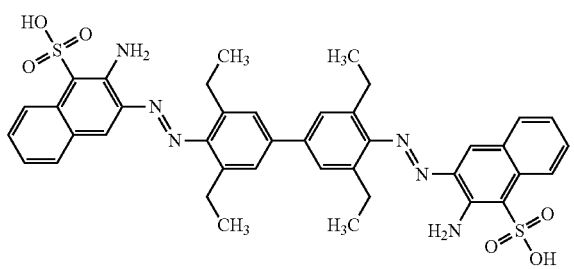 [SMILES: CCc1cc(-c2cc(CC)c(/N=N/c3cc4ccccc4c(S(=O)(=O)O)c3N)c(CC)c2)cc(CC)c1/N=N/c1cc2ccccc2c(S(=O)(=O)O)c1N]

32

1,1'-(3,3',5,5'-tetraethyl[1,1'-biphenyl]-4,4'-diyl)bis{2-amino-3-[(E)-diazenyl] naphthalene-1-sulfonic acid}

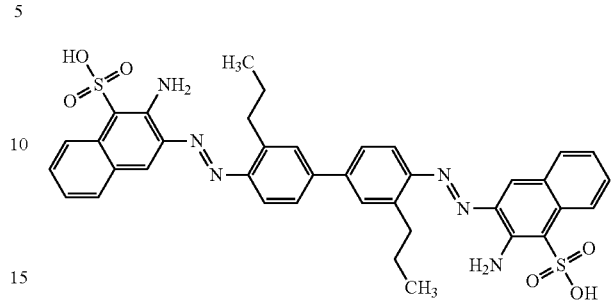

1,1'-(3,3'-dipropyl[1,1'-biphenyl]-4,4'-diyl)bis{2-amino-3-[(E)-diazenyl]naphthalene-1-sulfonic acid}

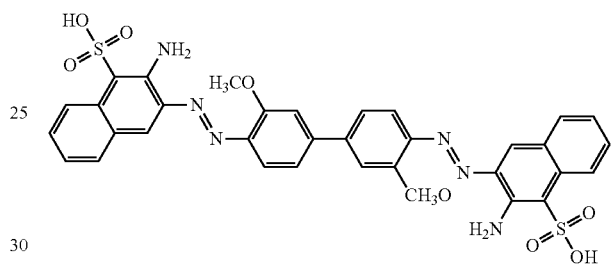

1,1'-(3,3'-dimethoxy[1,1'-biphenyl]-4,4'-diyl)bis{2-amino-3-[(E)-diazenyl] naphthalene-1-sulfonic acid}

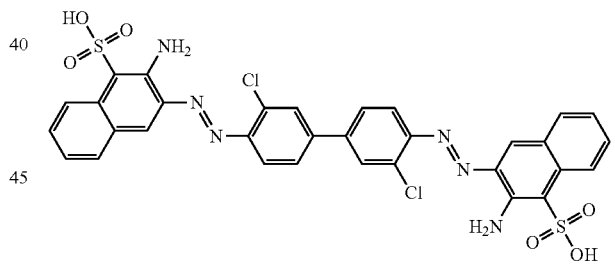

1,1'-(3,3'-dichloro[1,1'-biphenyl]-4,4'-diyl)bis{2-amino-3-[(E)-diazenyl]naphthalene-1-sulfonic acid}

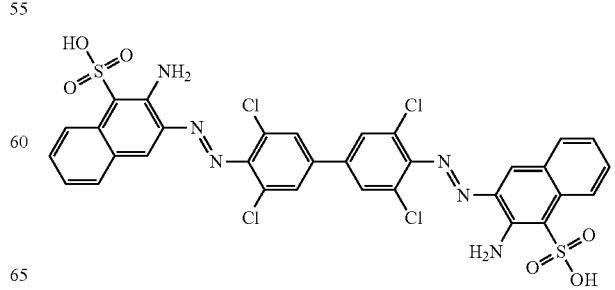

33

1,1'-(3,3',5,5'-tetrachloro[1,1'-biphenyl]-4,4'-diyl) bis{2-amino-3-[(E)-diazenyl] naphthalene-1-sulfonic acid}

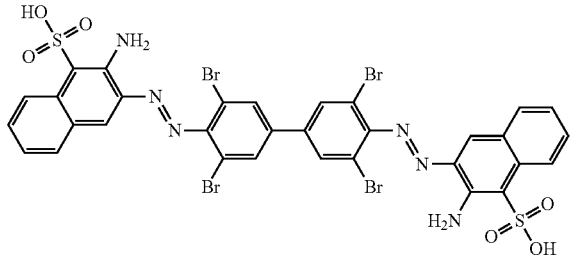 [SMILES: Nc1c(/N=N/c2c(Br)cc(-c3cc(Br)c(/N=N/c4cc5ccccc5c(S(=O)(=O)O)c4N)c(Br)c3)cc2Br)cc2ccccc2c1S(=O)(=O)O]

1,1'-(3,3',5,5'-tetrabromo[1,1'-biphenyl]-4,4'-diyl) bis{2-amino-3-[(E)-diazenyl] naphthalene-1-sulfonic acid}

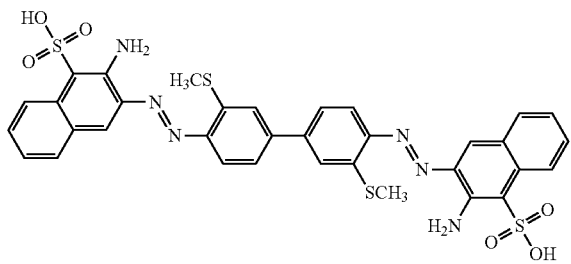

1,1'-(3,3'-dimethylthio[1,1'-biphenyl]-4,4'-diyl) bis{2-amino-3-[(E)-diazenyl] naphthalene-1-sulfonic acid}

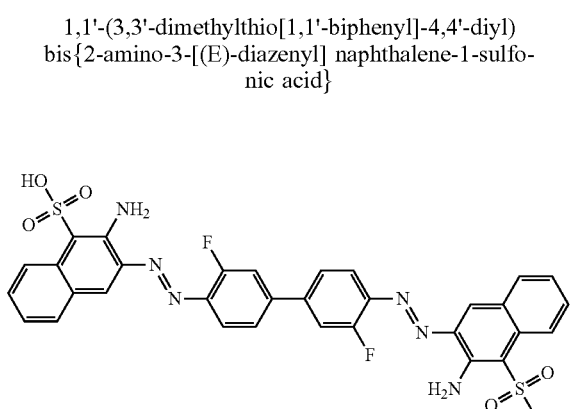

1,1'-(3,3'-difluoro[1,1'-biphenyl]-4,4'-diyl)bis{2-amino-3-[(E)-diazenyl]naphthalene-1-sulfonic acid}

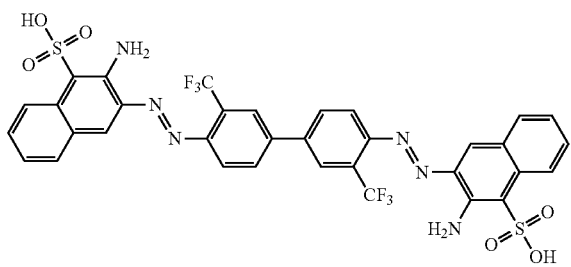

34

1,1'-(3,3'-ditrifluoromethyl[1,1'-biphenyl]-4,4'-diyl) bis{2-amino-3-[(E)-diazenyl] naphthalene-1-sulfonic acid}

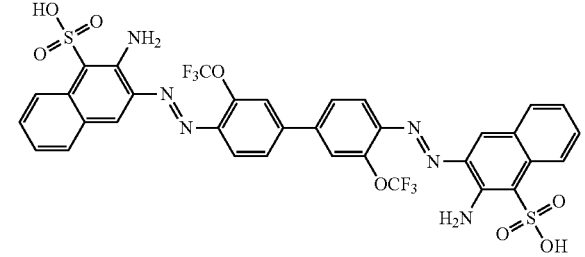 [SMILES: Nc1c(/N=N/c2ccc(-c3ccc(/N=N/c4cc5ccccc5c(S(=O)(=O)O)c4N)c(OC(F)(F)F)c3)cc2OC(F)(F)F)cc2ccccc2c1S(=O)(=O)O]

1,1'-(3,3'-ditrifluoromethoxy[1,1'-biphenyl]-4,4'-diyl)bis{2-amino-3-[(E)-diazenyl] naphthalene-1-sulfonic acid}

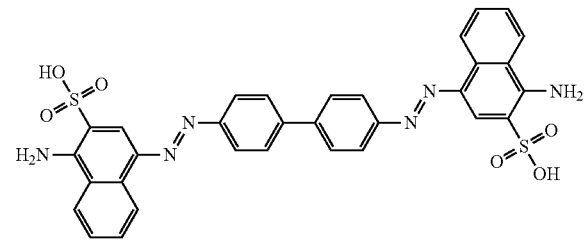 [SMILES: Nc1c(S(=O)(=O)O)cc(/N=N/c2ccc(-c3ccc(/N=N/c4cc(S(=O)(=O)O)c(N)c5ccccc45)cc3)cc2)c2ccccc12]

1,1'-([1,1'-biphenyl]-4,4'-diyl)bis{1-amino-4-[(E)-diazenyl]naphthalene-2-sulfonic acid}

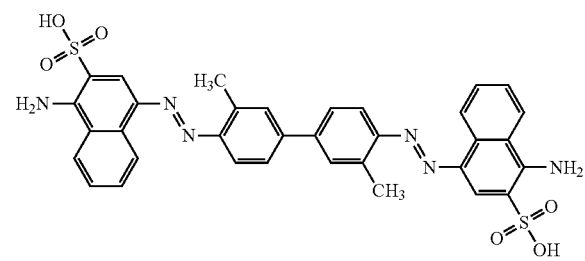 [SMILES: Cc1cc(-c2ccc(/N=N/c3cc(S(=O)(=O)O)c(N)c4ccccc34)c(C)c2)ccc1/N=N/c1cc(S(=O)(=O)O)c(N)c2ccccc12]

1,1'-(3,3'-dimethyl[1,1'-biphenyl]-4,4'-diyl)bis{1-amino-4-[(E)-diazenyl]naphthalene-2-sulfonic acid}

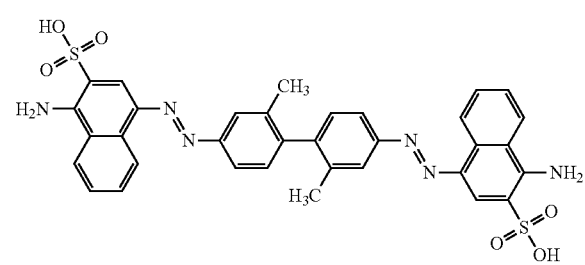 [SMILES: Cc1cc(/N=N/c2cc(S(=O)(=O)O)c(N)c3ccccc23)ccc1-c1ccc(/N=N/c2cc(S(=O)(=O)O)c(N)c3ccccc23)cc1C]

35

1,1'-(2,2'-dimethyl[1,1'-biphenyl]-4,4'-diyl)bis{1-amino-4-[(E)-diazenyl]naphthalene-2-sulfonic acid}

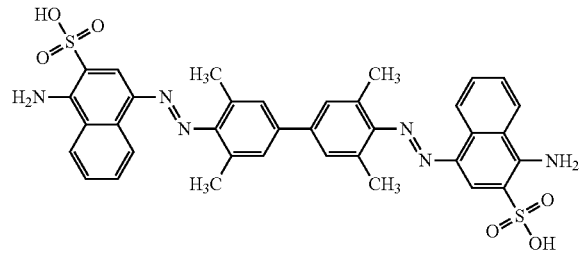 [SMILES: Cc1cc(-c2cc(C)c(/N=N/c3cc(S(=O)(=O)O)c(N)c4ccccc34)c(C)c2)cc(C)c1/N=N/c1cc(S(=O)(=O)O)c(N)c2ccccc12]

1,1'-(3,5,3',5'-dimethyl[1,1'-biphenyl]-4,4'-diyl)bis{1-amino-4-[(E)-diazenyl] naphthalene-2-sulfonic acid}

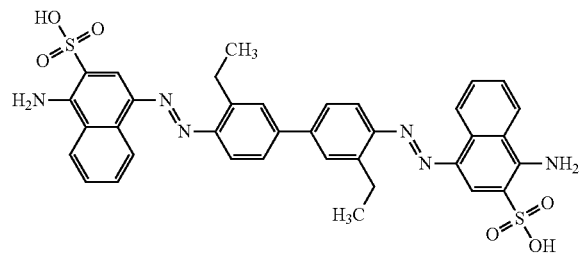 [SMILES: CCc1cc(-c2ccc(/N=N/c3cc(S(=O)(=O)O)c(N)c4ccccc34)c(CC)c2)ccc1/N=N/c1cc(S(=O)(=O)O)c(N)c2ccccc12]

1,1'-(3,3'-diethyl[1,1'-biphenyl]-4,4'-diyl)bis{1-amino-4-[(E)-diazenyl]naphthalene-2-sulfonic acid}

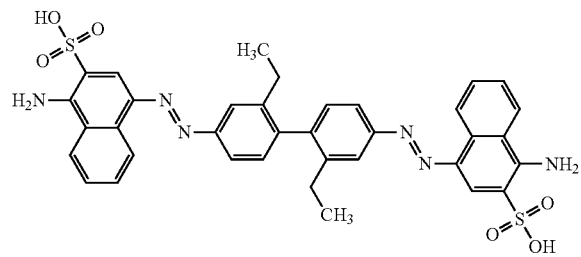 [SMILES: CCc1cc(/N=N/c2cc(S(=O)(=O)O)c(N)c3ccccc23)ccc1-c1ccc(/N=N/c2cc(S(=O)(=O)O)c(N)c3ccccc23)cc1CC]

1,1'-(2,2'-diethyl[1,1'-biphenyl]-4,4'-diyl)bis{1-amino-4-[(E)-diazenyl]naphthalene-2-sulfonic acid}

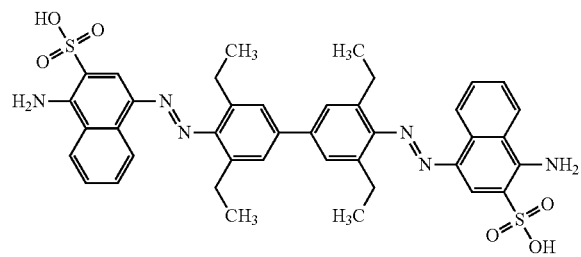 [SMILES: CCc1cc(-c2cc(CC)c(/N=N/c3cc(S(=O)(=O)O)c(N)c4ccccc34)c(CC)c2)cc(CC)c1/N=N/c1cc(S(=O)(=O)O)c(N)c2ccccc12]

36

1,1'-(3,5,3',5'-diethyl[1,1'-biphenyl]-4,4'-diyl)bis{1-amino-4-[(E)-diazenyl] naphthalene-2-sulfonic acid}

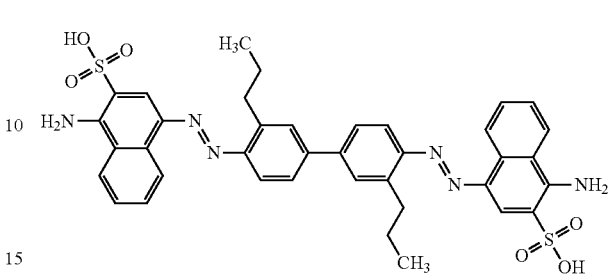

1,1'-(3,3'-dipropyl[1,1'-biphenyl]-4,4'-diyl)bis{1-amino-4-[(E)-diazenyl]naphthalene-2-sulfonic acid}

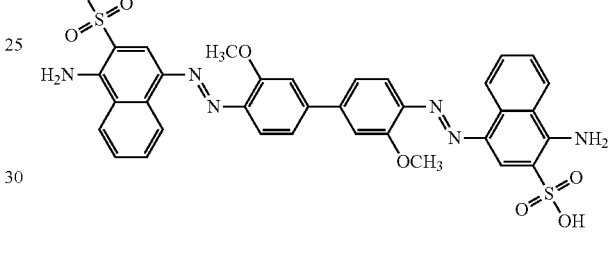

1,1'-(3,3'-dimethoxy[1,1'-biphenyl]-4,4'-diyl)bis{1-amino-4-[(E)-diazenyl] naphthalene-2-sulfonic acid}

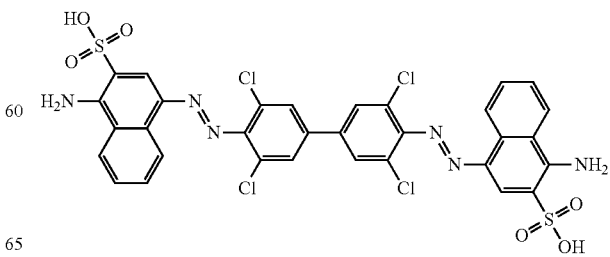

1,1'-(3,3'-dichloro[1,1'-biphenyl]-4,4'-diyl)bis{1-amino-4-[(E)-diazenyl]naphthalene-2-sulfonic acid}

37

1,1'-(3,5,3',5-dichloro[1,1'-biphenyl]-4,4'-diyl)bis{1-amino-4-[(E)-diazenyl] naphthalene-2-sulfonic acid}

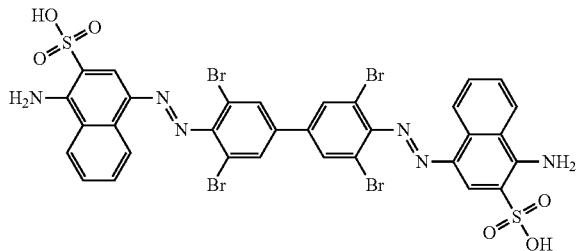

1,1'-(3,5,3',5-dibromo[1,1'-biphenyl]-4,4'-diyl)bis{1-amino-4-[(E)-diazenyl] naphthalene-2-sulfonic acid}

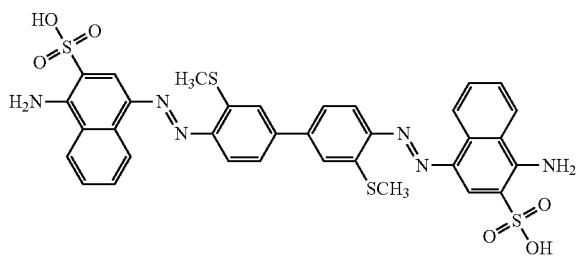 [SMILES: COc1cc(-c2ccc(/N=N/c3cc(S(=O)(=O)O)c(N)c4ccccc34)c(OC)c2)ccc1/N=N/c1cc(S(=O)(=O)O)c(N)c2ccccc12]

1,1'-(3,3'-dimethylthio[1,1'-biphenyl]-4,4'-diyl) bis{1-amino-4-[(E)-diazenyl] naphthalene-2-sulfonic acid}

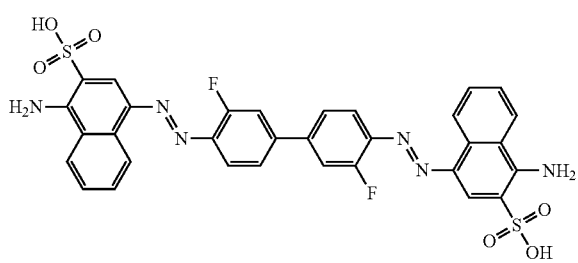 [SMILES: Nc1c(S(=O)(=O)O)cc(/N=N/c2ccc(-c3ccc(/N=N/c4cc(S(=O)(=O)O)c(N)c5ccccc45)c(Cl)c3)cc2Cl)c2ccccc12]

1,1'-(3,3'-difluoro[1,1'-biphenyl]-4,4'-diyl)bis{1-amino-4-[(E)-diazenyl]naphthalene-2-sulfonic acid}

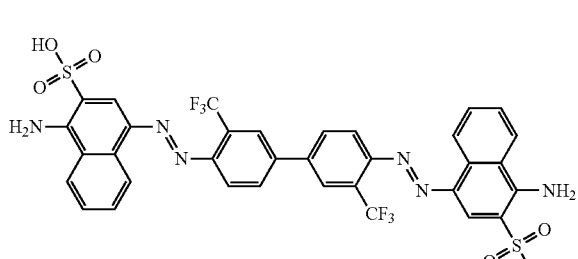

38

1,1'-(3,3'-ditrifluoromethyl[1,1'-biphenyl]-4,4'-diyl) bis{1-amino-4-[(E)-diazenyl]naphthalene-2-sulfonic acid}

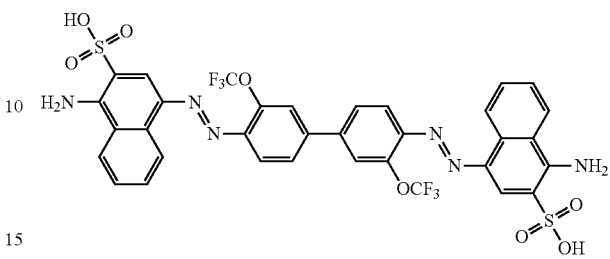

1,1'-(3,3'-ditrifluoromethoxy[1,1'-biphenyl]-4,4'-diyl)bis{1-amino-4-[(E)-diazenyl] naphthalene-2-sulfonic acid}

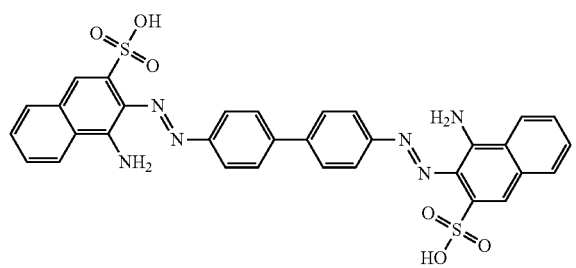

1,1'-([1,1'-biphenyl]-4,4'-diyl)bis{4-amino-3-[(E)-diazenyl]naphthalene-2-sulfonic acid}

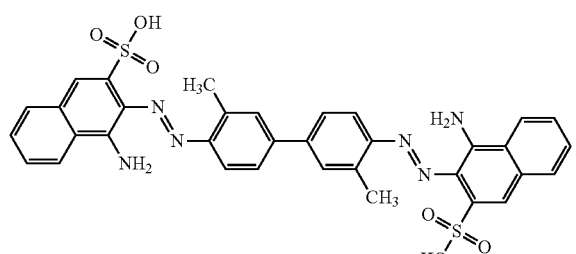

1,1'-(3,3'-dimethyl[1,1'-biphenyl]-4,4'-diyl)bis{4-amino-3-[(E)-diazenyl]naphthalene-2-sulfonic acid}

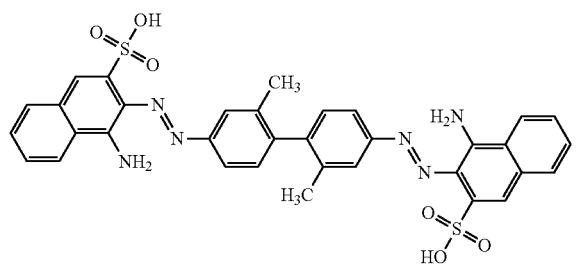

| 39 | 40 |
|---|---|
| 1,1'-(2,2'-dimethyl[1,1'-biphenyl]-4,4'-diyl)bis{4-amino-3-[(E)-diazenyl]naphthalene-2-sulfonic acid} | 1,1'-(3,5,3',5'-tetraethyl[1,1'-biphenyl]-4,4'-diyl)bis{4-amino-3-[(E)-diazenyl] naphthalene-2-sulfonic acid} |

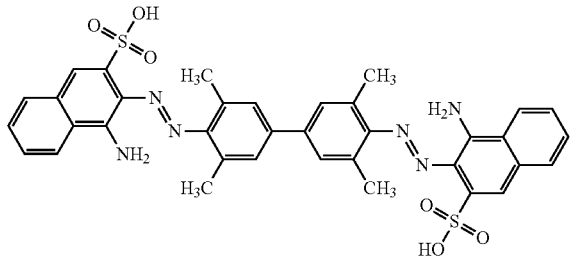 [SMILES: Cc1cc(-c2cc(C)c(/N=N/c3c(S(=O)(=O)O)cc4ccccc4c3N)c(C)c2)cc(C)c1/N=N/c1c(S(=O)(=O)O)cc2ccccc2c1N]

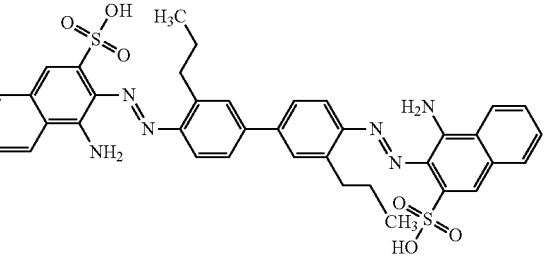

1,1'-(3,5,3',5'-tetramethyl [1,1'-biphenyl]-4,4'-diyl)bis{4-amino-3-[(E)-diazenyl] naphthalene-2-sulfonic acid}

1,1'-(3,3'-dipropyl[1,1'-biphenyl]-4,4'-diyl)bis{4-amino-3-[(E)-diazenyl]naphthalene-2-sulfonic acid}

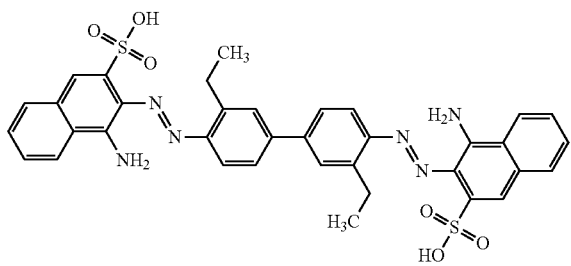

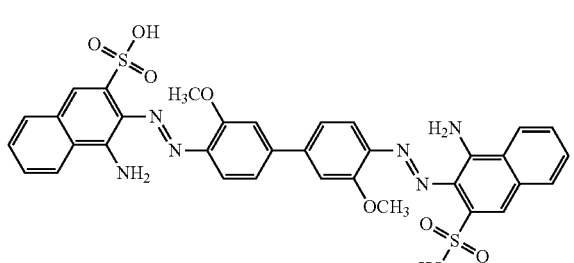

1,1'-(3,3'-diethyl[1,1'-biphenyl]-4,4'-diyl)bis{4-amino-3-[(E)-diazenyl]naphthalene-2-sulfonic acid}

1,1'-(3,3'-dimethoxy[1,1'-biphenyl]-4,4'-diyl)bis{4-amino-3-[(E)-diazenyl] naphthalene-2-sulfonic acid}

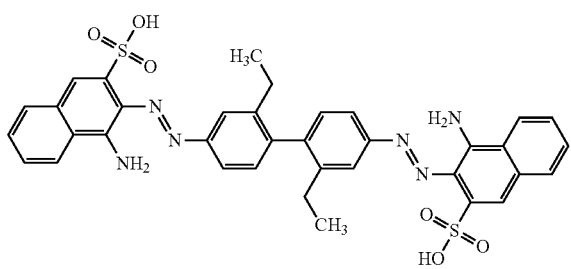 [SMILES: CCc1cc(/N=N/c2c(S(=O)(=O)O)cc3ccccc3c2N)ccc1-c1ccc(/N=N/c2c(S(=O)(=O)O)cc3ccccc3c2N)cc1CC]

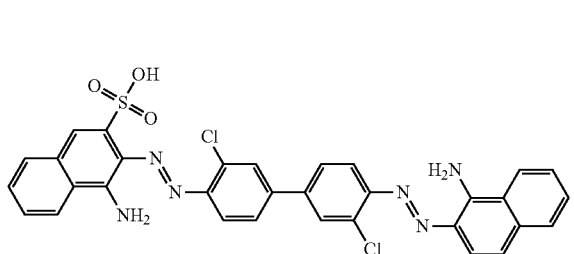

1,1'-(2,2'-diethyl[1,1'-biphenyl]-4,4'-diyl)bis{4-amino-3-[(E)-diazenyl]naphthalene-2-sulfonic acid}

1,1'-(3,3'-dichloro[1,1'-biphenyl]-4,4'-diyl)bis{4-amino-3-[(E)-diazenyl]naphthalene-2-sulfonic acid}

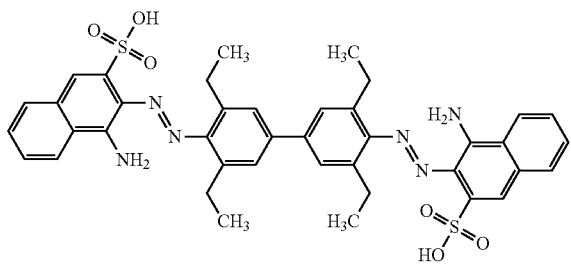

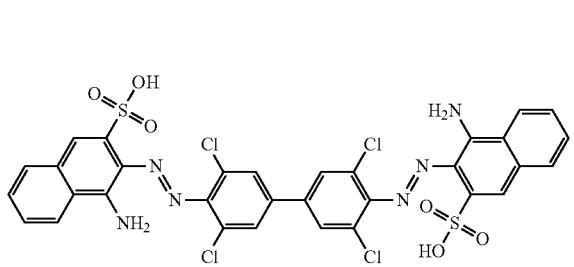 [SMILES: Nc1c(/N=N/c2c(Cl)cc(-c3cc(Cl)c(/N=N/c4c(S(=O)(=O)O)cc5ccccc5c4N)c(Cl)c3)cc2Cl)c(S(=O)(=O)O)cc2ccccc12]

41

1,1'-(3,5,3',5'-tetrachloro[1,1'-biphenyl]-4,4'-diyl)bis{4-amino-3-[(E)-diazenyl] naphthalene-2-sulfonic acid}

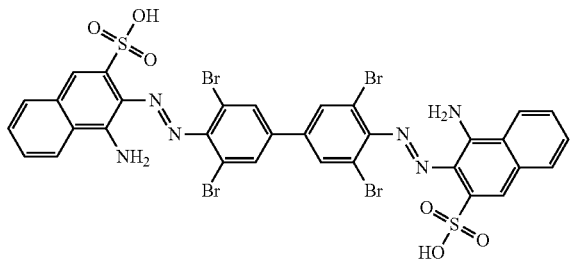 [SMILES: Nc1c(/N=N/c2c(Br)cc(-c3cc(Br)c(/N=N/c4c(S(=O)(=O)O)cc5ccccc5c4N)c(Br)c3)cc2Br)c(S(=O)(=O)O)cc2ccccc12]

1,1'-(3,5,3',5'-tetrabromo[1,1'-biphenyl]-4,4'-diyl)bis{4-amino-3-[(E)-diazenyl] naphthalene-2-sulfonic acid}

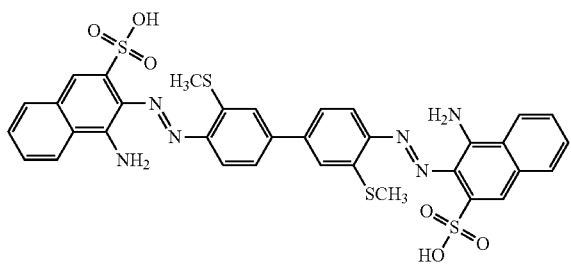

1,1'-(3,3'-dimethylthio[1,1'-biphenyl]-4,4'-diyl)bis{4-amino-3-[(E)-diazenyl] naphthalene-2-sulfonic acid}

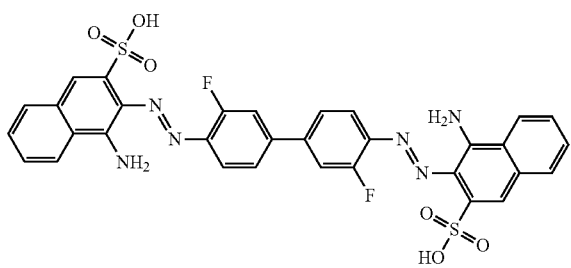

1,1'-(3,3'-difluoro[1,1'-biphenyl]-4,4'-diyl)bis{4-amino-3-[(E)-diazenyl]naphthalene-2-sulfonic acid}

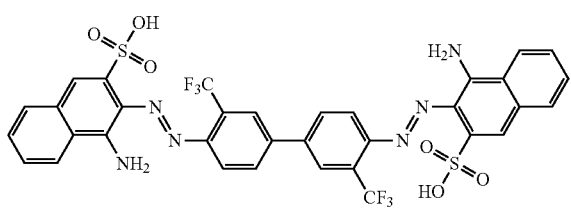

42

1,1'-(3,3'-ditrifluoromethyl[1,1'-biphenyl]-4,4'-diyl)bis{4-amino-3-[(E)-diazenyl] naphthalene-2-sulfonic acid}

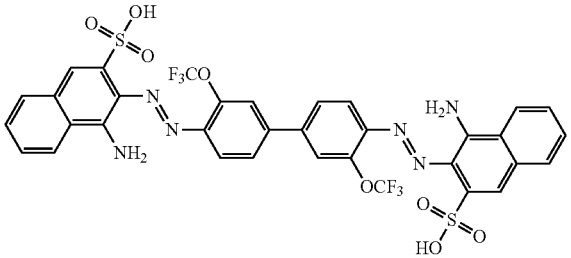

1,1'-(3,3'-ditrifluoromethoxy[1,1'-biphenyl]-4,4'-diyl)bis{4-amino-3-[(E)-diazenyl] naphthalene-2-sulfonic acid}

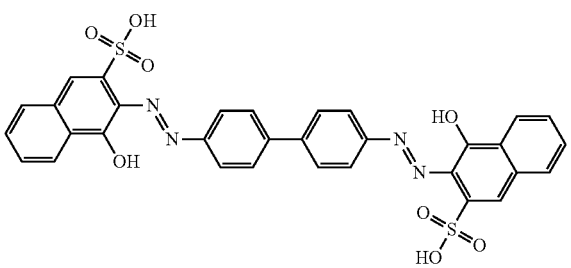 [SMILES: O=S(=O)(O)c1cc2ccccc2c(O)c1/N=N/c1ccc(-c2ccc(/N=N/c3c(S(=O)(=O)O)cc4ccccc4c3O)cc2)cc1]

1,1'-([1,1'-biphenyl]-4,4'-diyl)bis{4-hydroxy-3-[(E)-diazenyl]naphthalene-2-sulfonic acid}

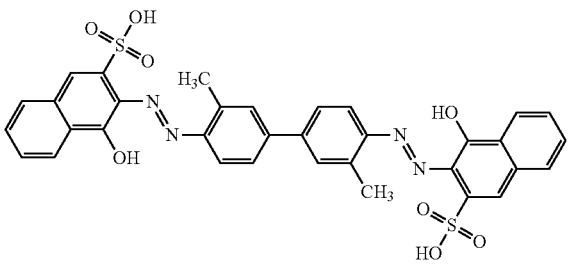 [SMILES: Cc1cc(-c2ccc(/N=N/c3c(S(=O)(=O)O)cc4ccccc4c3O)c(C)c2)ccc1/N=N/c1c(S(=O)(=O)O)cc2ccccc2c1O]

1,1'-(3,3'-dimethyl[1,1'-biphenyl]-4,4'-diyl)bis{4-hydroxy-3-[(E)-diazenyl] naphthalene-2-sulfonic acid}

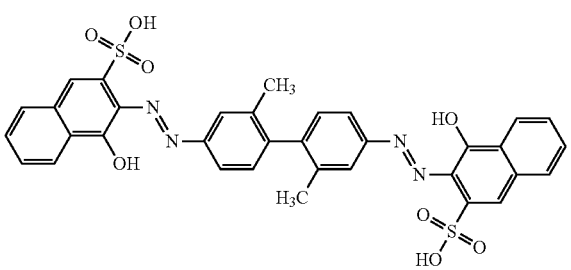 [SMILES: Cc1cc(/N=N/c2c(S(=O)(=O)O)cc3ccccc3c2O)ccc1-c1ccc(/N=N/c2c(S(=O)(=O)O)cc3ccccc3c2O)cc1C]

43

1,1'-(2,2'-dimethyl[1,1'-biphenyl]-4,4'-diyl)bis{4-hydroxy-3-[(E)-diazenyl] naphthalene-2-sulfonic acid}

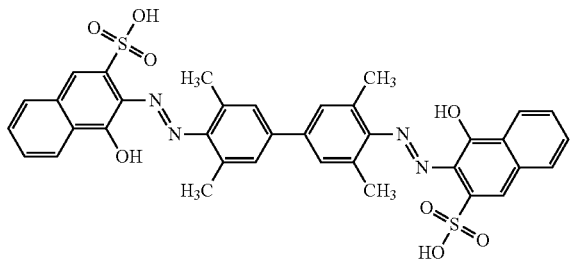 [SMILES: Cc1cc(-c2cc(C)c(/N=N/c3c(S(=O)(=O)O)cc4ccccc4c3O)c(C)c2)cc(C)c1/N=N/c1c(S(=O)(=O)O)cc2ccccc2c1O]

1,1'-(3,5,3',5'-tetramethyl [1,1'-biphenyl]-4,4'-diyl)bis{4-hydroxy-3-[(E)-diazenyl] naphthalene-2-sulfonic acid}

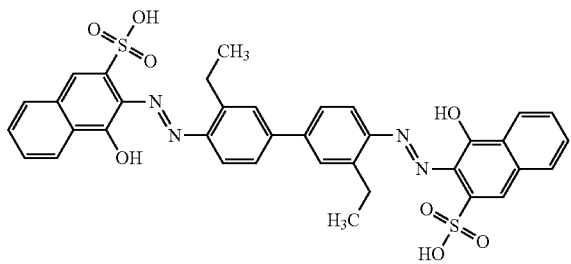 [SMILES: CCc1cc(-c2ccc(/N=N/c3c(S(=O)(=O)O)cc4ccccc4c3O)c(CC)c2)ccc1/N=N/c1c(S(=O)(=O)O)cc2ccccc2c1O]

1,1'-(3,3'-diethyl[1,1'-biphenyl]-4,4'-diyl)bis{4-hydroxy-3-[(E)-diazenyl]naphthalene-2-sulfonic acid}

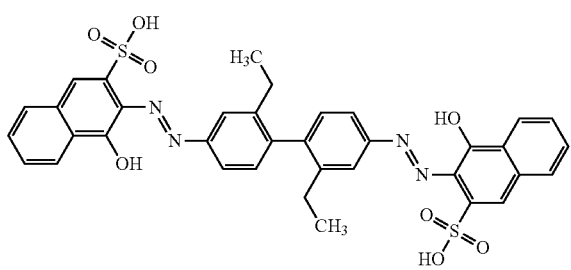 [SMILES: CCc1cc(/N=N/c2c(S(=O)(=O)O)cc3ccccc3c2O)ccc1-c1ccc(/N=N/c2c(S(=O)(=O)O)cc3ccccc3c2O)cc1CC]

1,1'-(2,2'-diethyl[1,1'-biphenyl]-4,4'-diyl)bis{4-hydroxy-3-[(E)-diazenyl]naphthalene-2-sulfonic acid}

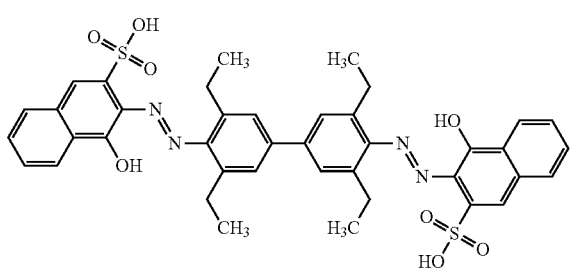 [SMILES: CCc1cc(-c2cc(CC)c(/N=N/c3c(S(=O)(=O)O)cc4ccccc4c3O)c(CC)c2)cc(CC)c1/N=N/c1c(S(=O)(=O)O)cc2ccccc2c1O]

44

1,1'-(3,5,3',5'-tetraethyl[1,1'-biphenyl]-4,4'-diyl)bis{4-hydroxy-3-[(E)-diazenyl] naphthalene-2-sulfonic acid}

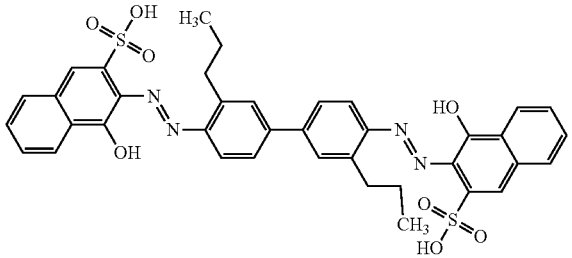 [SMILES: CCCc1cc(-c2ccc(/N=N/c3c(S(=O)(=O)O)cc4ccccc4c3O)c(CCC)c2)ccc1/N=N/c1c(S(=O)(=O)O)cc2ccccc2c1O]

1,1'-(3,3'-dipropyl[1,1'-biphenyl]-4,4'-diyl)bis{4-hydroxy-3-[(E)-diazenyl] naphthalene-2-sulfonic acid}

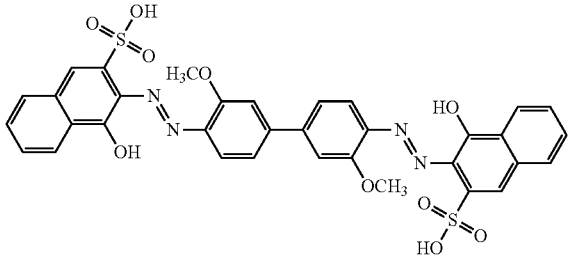 [SMILES: COc1cc(-c2ccc(/N=N/c3c(S(=O)(=O)O)cc4ccccc4c3O)c(OC)c2)ccc1/N=N/c1c(S(=O)(=O)O)cc2ccccc2c1O]

1,1'-(3,3'-dimethoxy[1,1'-biphenyl]-4,4'-diyl)bis{4-hydroxy-3-[(E)-diazenyl] naphthalene-2-sulfonic acid}

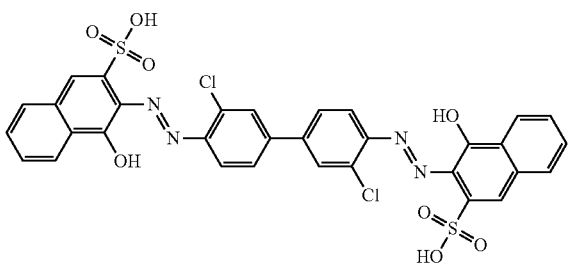

1,1'-(3,3'-dichloro[1,1'-biphenyl]-4,4'-diyl)bis{4-hydroxy-3-[(E)-diazenyl] naphthalene-2-sulfonic acid}

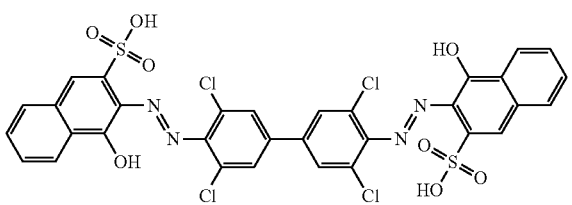 [SMILES: O=S(=O)(O)c1cc2ccccc2c(O)c1/N=N/c1c(Cl)cc(-c2cc(Cl)c(/N=N/c3c(S(=O)(=O)O)cc4ccccc4c3O)c(Cl)c2)cc1Cl]

45

1,1'-(3,5,3',5'-tetrachloro[1,1'-biphenyl]-4,4'-diyl)
bis{4-hydroxy-3-[(E)-diazenyl] naphthalene-2-sulfonic acid}

46

1,1'-(3,3'-difluoro[1,1'-biphenyl]-4,4'-diyl)bis{4-hydroxy-3-[(E)-diazenyl] naphthalene-2-sulfonic acid}

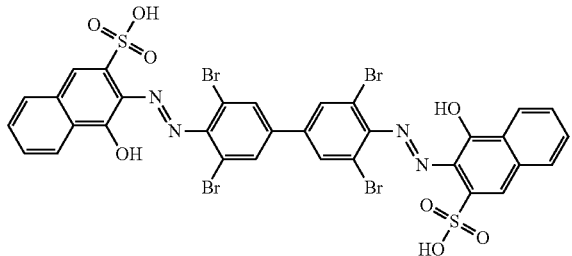 [SMILES: O=S(=O)(O)c1cc2ccccc2c(O)c1/N=N/c1c(Br)cc(-c2cc(Br)c(/N=N/c3c(S(=O)(=O)O)cc4ccccc4c3O)c(Br)c2)cc1Br]

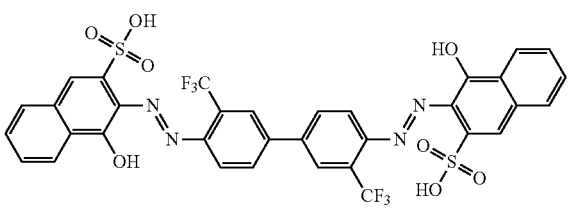

1,1'-(3,5,3',5'-tetrabromo[1,1'-biphenyl]-4,4'-diyl)
bis{4-hydroxy-3-[(E)-diazenyl] naphthalene-2-sulfonic acid}

1,1'-(3,3'-ditrifluoromethyl[1,1'-biphenyl]-4,4'-diyl)
bis{4-hydroxy-3-[(E)-diazenyl] naphthalene-2-sulfonic acid}

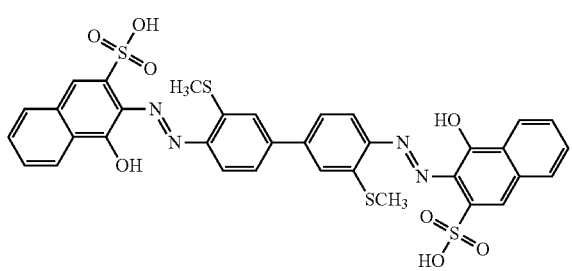

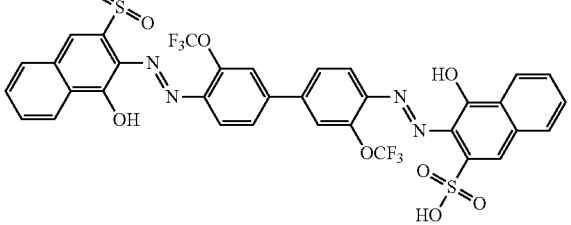

1,1'-(3,3'-dimethylthio[1,1'-biphenyl]-4,4'-diyl)
bis{4-hydroxy-3-[(E)-diazenyl] naphthalene-2-sulfonic acid}

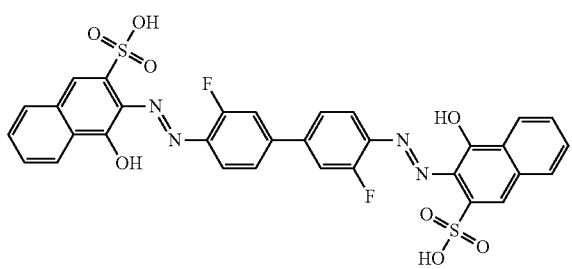

1,1'-(3,3'-ditrifluoromethoxy[1,1'-biphenyl]-4,4'-diyl)bis{4-hydroxy-3-[(E)-diazenyl]naphthalene-2-sulfonic acid}

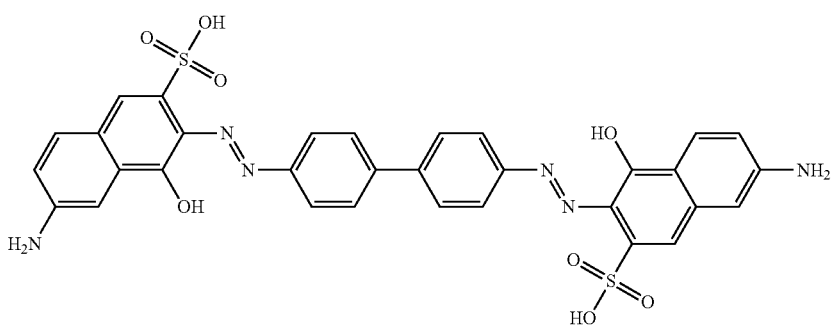

1,1'-([1,1'-biphenyl]-4,4'-diyl)bis{7-amino-4-hydroxy-3-[(E)-diazenyl]naphthalene-2-sulfonic acid}
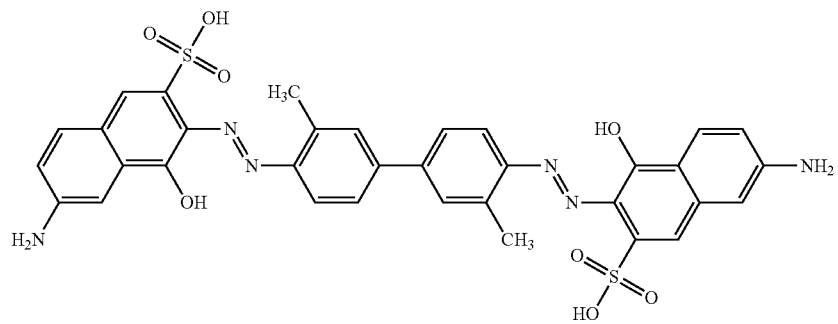
1,1'-(3,3'-dimethyl[1,1'-biphenyl]-4,4'-diyl)bis{7-amino-4-hydroxy-3-[(E)-diazenyl] naphthalene-2-sulfonic acid}
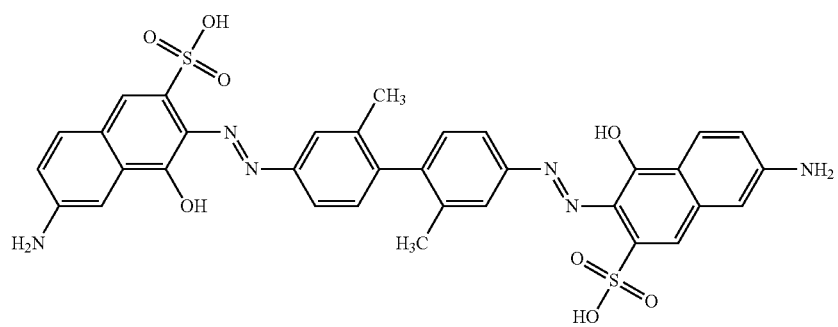 [SMILES: Cc1cc(/N=N/c2c(S(=O)(=O)O)cc3cc(N)ccc3c2O)ccc1-c1ccc(/N=N/c2c(S(=O)(=O)O)cc3ccc(N)cc3c2O)cc1C]
1,1'-(2,2'-dimethyl[1,1'-biphenyl]-4,4'-diyl)bis{7-amino-4-hydroxy-3-[(E)-diazenyl] naphthalene-2-sulfonic acid}
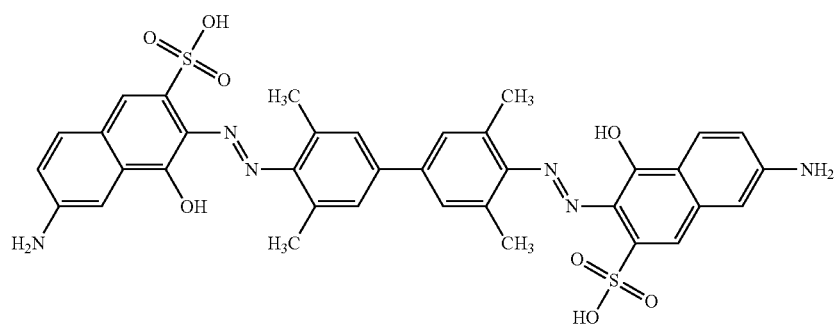 [SMILES: Cc1cc(-c2cc(C)c(/N=N/c3c(S(=O)(=O)O)cc4ccc(N)cc4c3O)c(C)c2)cc(C)c1/N=N/c1c(S(=O)(=O)O)cc2cc(N)ccc2c1O]

1,1'-(3,5,3',5'-tetramethyl [1,1'-biphenyl]-4,4'-diyl)
bis{7-amino-4-hydroxy-3-[(E)-diazenyl] naphthalene-2-sulfonic acid}
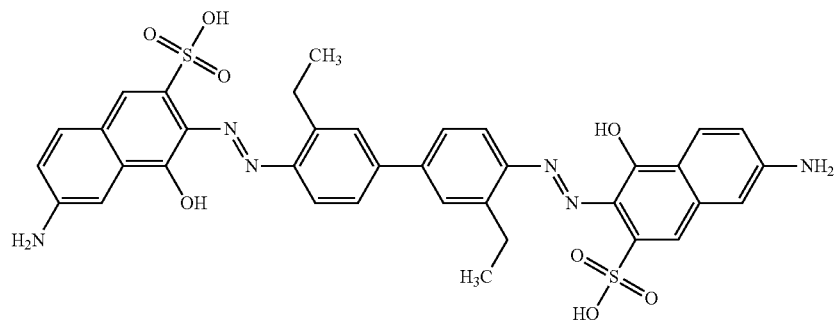
1,1'-(3,3'-diethyl[1,1'-biphenyl]-4,4'-diyl)bis{7-amino-4-hydroxy-3-[(E)-diazenyl]naphthalene-2-sulfonic acid}
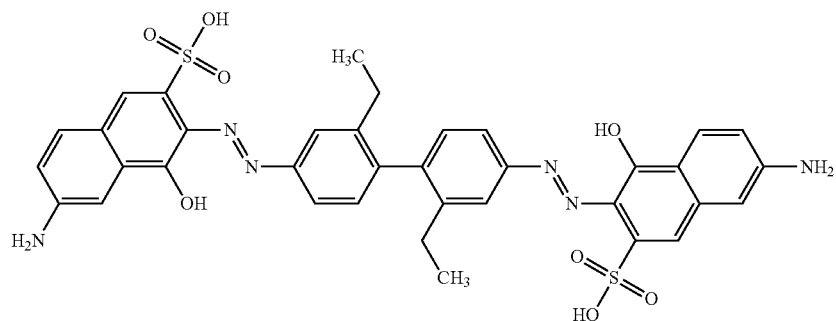 [SMILES: CCc1cc(/N=N/c2c(S(=O)(=O)O)cc3cc(N)ccc3c2O)ccc1-c1ccc(/N=N/c2c(S(=O)(=O)O)cc3ccc(N)cc3c2O)cc1CC]
1,1'-(2,2'-diethyl[1,1'-biphenyl]-4,4'-diyl)bis{7-amino-4-hydroxy-3-[(E)-diazenyl]naphthalene-2-sulfonic acid}
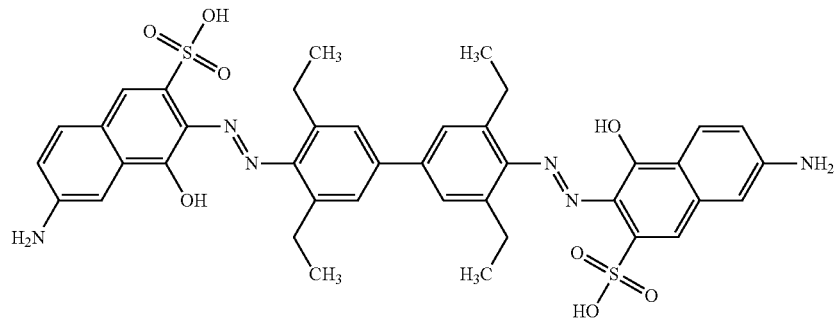 [SMILES: CCc1cc(-c2cc(CC)c(/N=N/c3c(S(=O)(=O)O)cc4ccc(N)cc4c3O)c(CC)c2)cc(CC)c1/N=N/c1c(S(=O)(=O)O)cc2cc(N)ccc2c1O]

1,1'-(3,5,3',5'-tetraethyl[1,1'-biphenyl]-4,4'-diyl)
bis{7-amino-4-hydroxy-3-[(E)-diazenyl]naphtha-
lene-2-sulfonic acid}
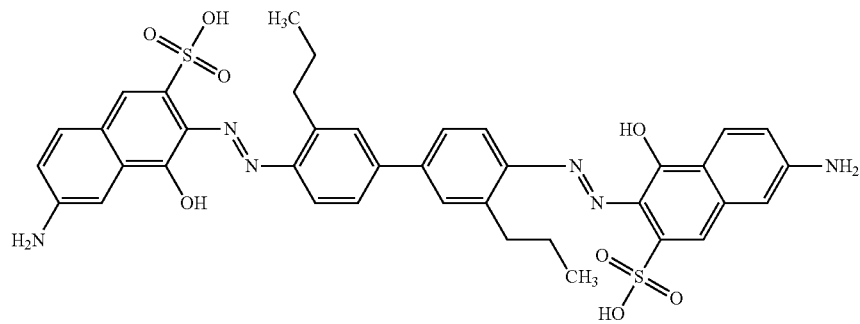 [SMILES: CCCc1cc(-c2ccc(/N=N/c3c(S(=O)(=O)O)cc4ccc(N)cc4c3O)c(CCC)c2)ccc1/N=N/c1c(S(=O)(=O)O)cc2cc(N)ccc2c1O]
1,1'-(3,3'-dipropyl[1,1'-biphenyl]-4,4'-diyl)bis{7-
amino-4-hydroxy-3-[(E)-diazenyl]naphthalene-2-
sulfonic acid}
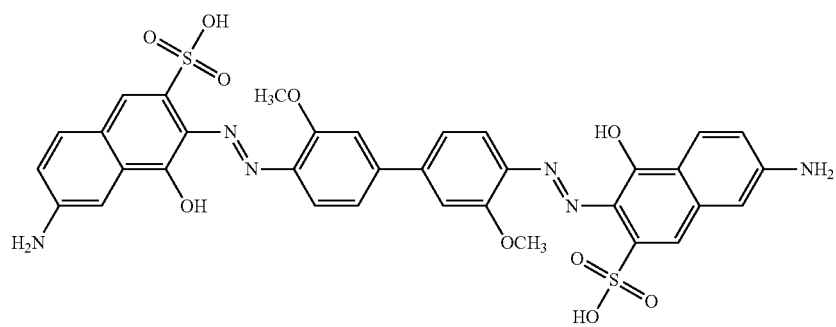
1,1'-(3,3'-dimethoxy[1,1'-biphenyl]-4,4'-diyl)bis{7-
amino-4-hydroxy-3-[(E)-diazenyl]naphthalene-2-
sulfonic acid}
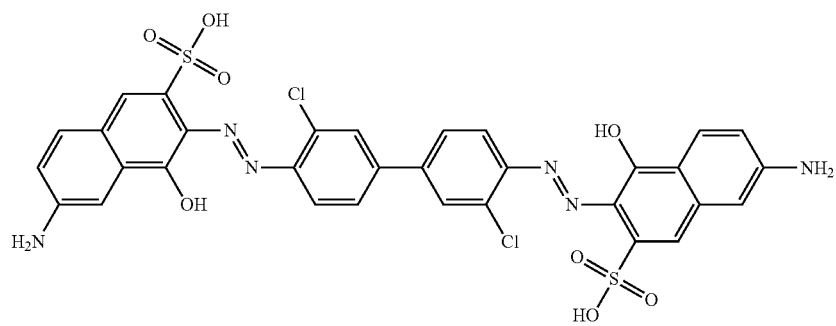

1,1'-(3,3'-dichloro[1,1'-biphenyl]-4,4'-diyl)bis{7-amino-4-hydroxy-3-[(E)-diazenyl] naphthalene-2-sulfonic acid}
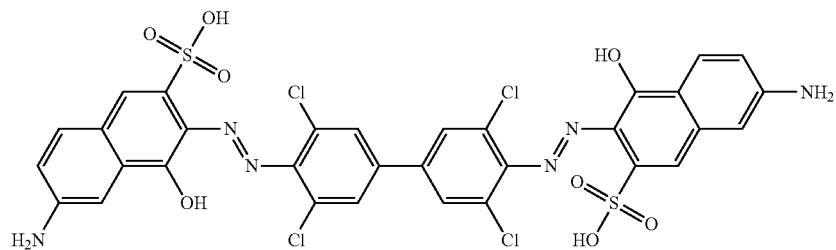 [SMILES: Nc1ccc2c(O)c(/N=N/c3c(Cl)cc(-c4cc(Cl)c(/N=N/c5c(S(=O)(=O)O)cc6ccc(N)cc6c5O)c(Cl)c4)cc3Cl)c(S(=O)(=O)O)cc2c1]
1,1'-(3,5,3',5'-tetrachloro[1,1'-biphenyl]-4,4'-diyl)bis{7-amino-4-hydroxy-3-[(E)-diazenyl]naphthalene-2-sulfonic acid}
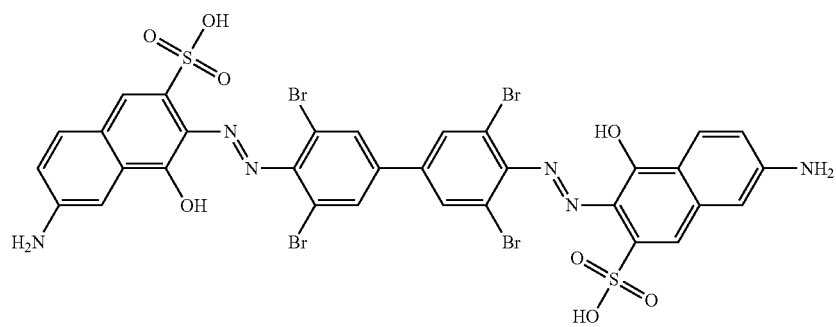 [SMILES: Nc1ccc2c(O)c(/N=N/c3c(Br)cc(-c4cc(Br)c(/N=N/c5c(S(=O)(=O)O)cc6ccc(N)cc6c5O)c(Br)c4)cc3Br)c(S(=O)(=O)O)cc2c1]
1,1'-(3,5,3',5'-tetrabromo[1,1'-biphenyl]-4,4'-diyl)bis{7-amino-4-hydroxy-3-[(E)-diazenyl]naphthalene-2-sulfonic acid}
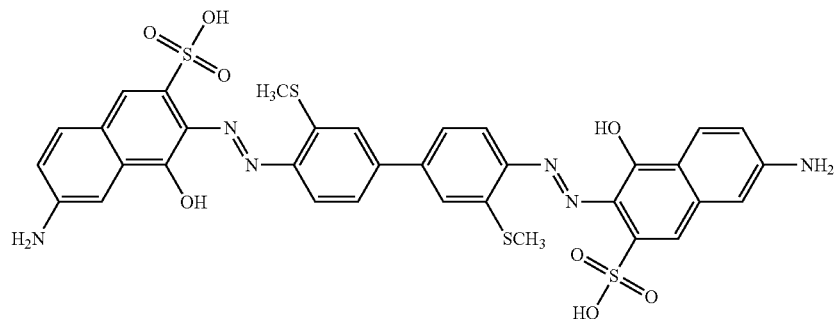

1,1'-(3,3'-dimethylthio[1,1'-biphenyl]-4,4'-diyl)bis{7-amino-4-hydroxy-3-[(E)-diazenyl]naphthalene-2-sulfonic acid}
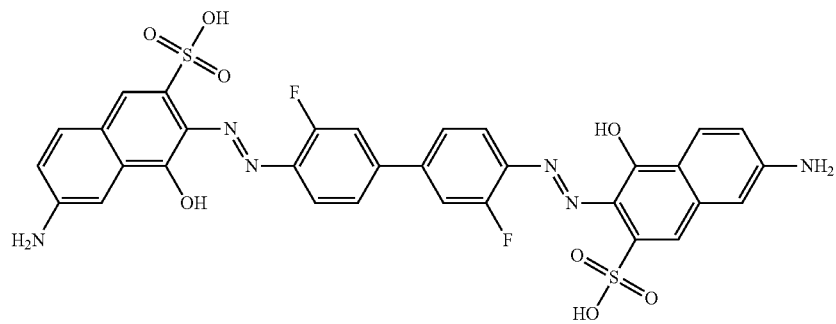 [SMILES: Nc1ccc2c(O)c(/N=N/c3ccc(-c4ccc(/N=N/c5c(S(=O)(=O)O)cc6ccc(N)cc6c5O)c(F)c4)cc3F)c(S(=O)(=O)O)cc2c1]
1,1'-(3,3'-difluoro[1,1'-biphenyl]-4,4'-diyl)bis{7-amino-4-hydroxy-3-[(E)-diazenyl]naphthalene-2-sulfonic acid}
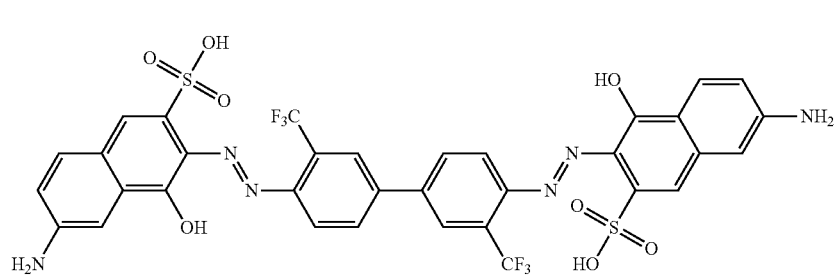 [SMILES: Nc1ccc2c(O)c(/N=N/c3ccc(-c4ccc(/N=N/c5c(S(=O)(=O)O)cc6ccc(N)cc6c5O)c(C(F)(F)F)c4)cc3C(F)(F)F)c(S(=O)(=O)O)cc2c1]
1,1'-(3,3'-ditrifluoromethyl[1,1'-biphenyl]-4,4'-diyl)bis{7-amino-4-hydroxy-3-[(E)-diazenyl]naphthalene-2-sulfonic acid}
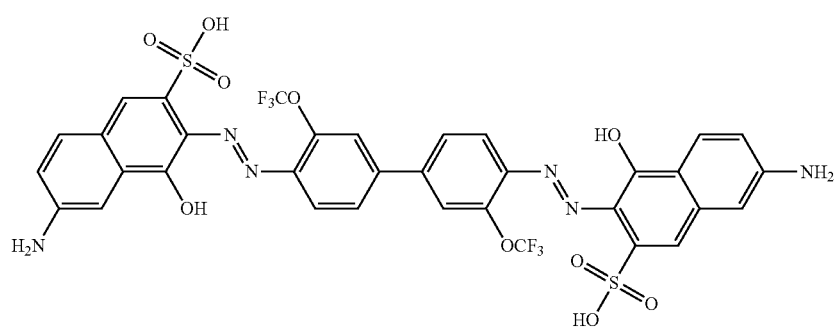 [SMILES: Nc1ccc2c(O)c(/N=N/c3ccc(-c4ccc(/N=N/c5c(S(=O)(=O)O)cc6ccc(N)cc6c5O)c(OC(F)(F)F)c4)cc3OC(F)(F)F)c(S(=O)(=O)O)cc2c1]

57

1,1'-(3,3'-ditrifluoromethoxy[1,1'-biphenyl]-4,4'-diyl)bis{7-amino-4-hydroxy-3-[(E)-diazenyl]naphthalene-2-sulfonic acid}

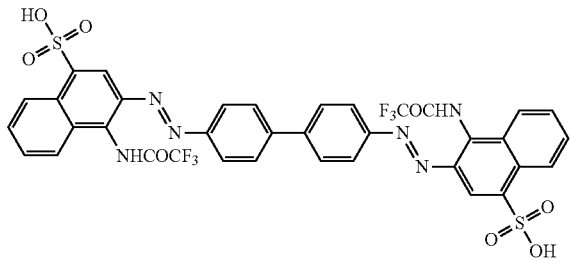

1,1'-([1,1'-biphenyl]-4,4'-diyl)bis{4-trifluoroacetylamino-3-[(E)-diazenyl] naphthalene-1-sulfonic acid}

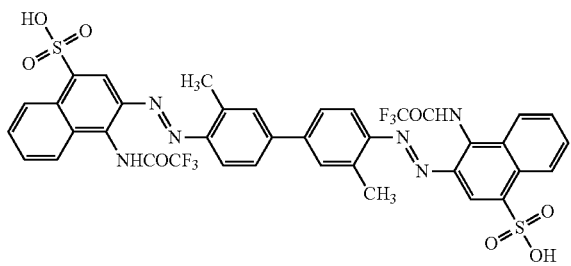

1,1'-(3,3'-dimethyl[1,1'-biphenyl]-4,4'-diyl)bis{4-trifluoroacetylamino-3-[(E)-diazenyl]naphthalene-1-sulfonic acid}

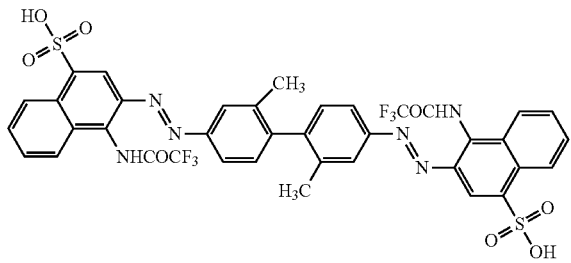

1,1'-(2,2'-dimethyl[1,1'-biphenyl]-4,4'-diyl)bis{4-trifluoroacetylamino-3-[(E)-diazenyl]naphthalene-1-sulfonic acid}

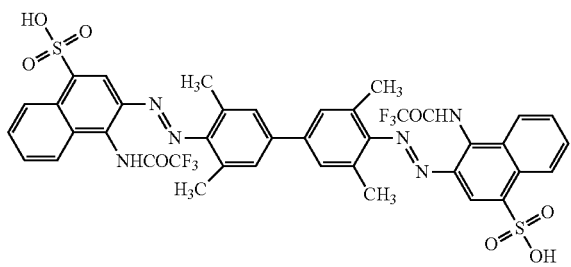

58

1,1'-(3,3',5,5'-tetramethyl[1,1'-biphenyl]-4,4'-diyl)bis{4-trifluoroacetylamino-3-[(E)-diazenyl]naphthalene-1-sulfonic acid}

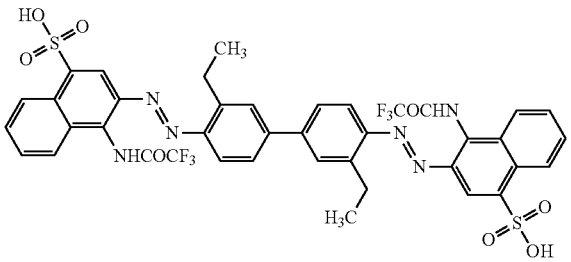

1,1'-(3,3'-diethy[1,1'-biphenyl]-4,4'-diyl)bis{4-trifluoroacetylamino-3-[(E)-diazenyl]naphthalene-1-sulfonic acid}

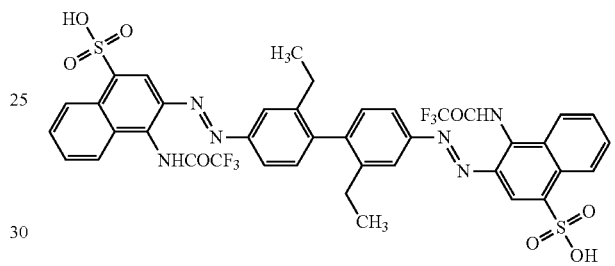

1,1'-(2,2'-diethy[1,1'-biphenyl]-4,4'-diyl)bis{4-trifluoroacetylamino-3-[(E)-diazenyl]naphthalene-1-sulfonic acid}

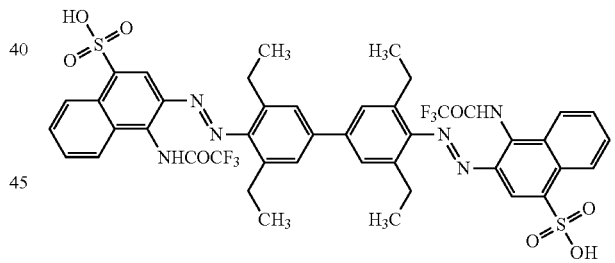

1,1'-(3,3',5,5'-tetraethyl[1,1'-biphenyl]-4,4'-diyl)bis{4-trifluoroacetylamino-3-[(E)-diazenyl]naphthalene-1-sulfonic acid}

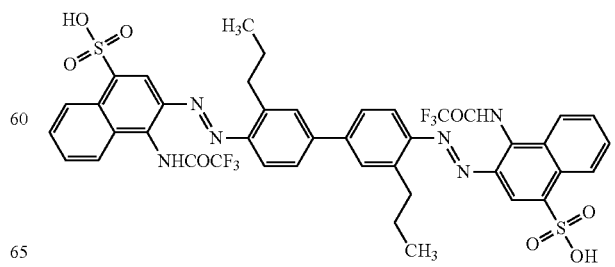

| 59 | 60 |
|---|---|
| 1,1'-(3,3'-dipropyl[1,1'-biphenyl]-4,4'-diyl)bis{4-trifluoroacetylamino-3-[(E)-diazenyl]naphthalene-1-sulfonic acid} | 1,1'-(3,3',5,5'-tetrabromo[1,1'-biphenyl]-4,4'-diyl)bis{4-trifluoroacetylamino-3-[(E)-diazenyl]naphthalene-1-sulfonic acid} |

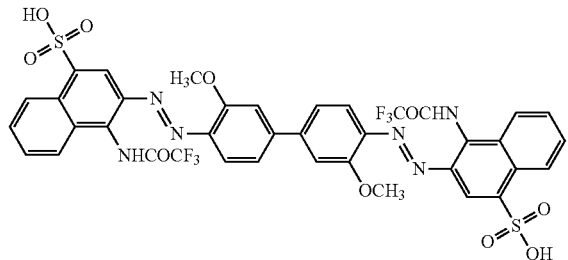 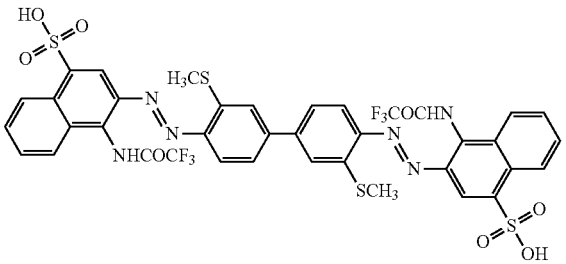

1,1'-(3,3'-dimethoxy[1,1'-biphenyl]-4,4'-diyl)bis{4-trifluoroacetylamino-3-[(E)-diazenyl]naphthalene-1-sulfonic acid}

1,1'-(3,3'-dimethylthio[1,1'-biphenyl]-4,4'-diyl)bis{4-trifluoroacetylamino-3-[(E)-diazenyl]naphthalene-1-sulfonic acid}

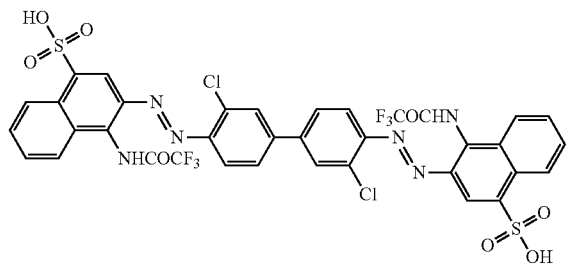 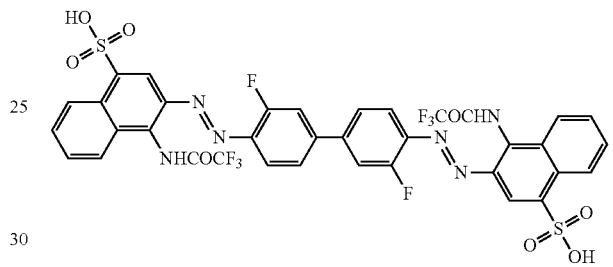

1,1'-(3,3'-dichloro[1,1'-biphenyl]-4,4'-diyl)bis{4-trifluoroacetylamino-3-[(E)-diazenyl]naphthalene-1-sulfonic acid}

1,1'-(3,3'-difluoro[1,1'-biphenyl]-4,4'-diyl)bis{4-trifluoroacetylamino-3-[(E)-diazenyl]naphthalene-1-sulfonic acid}

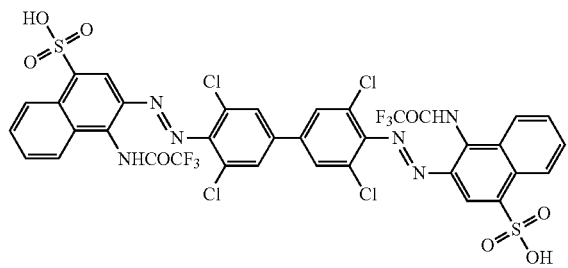 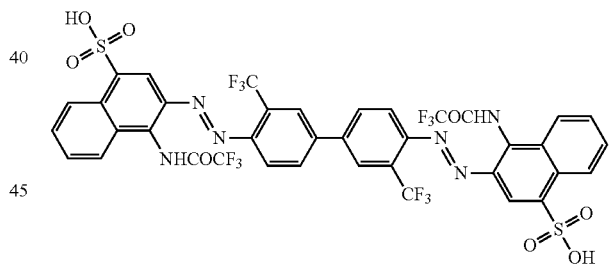

1,1'-(3,3',5,5'-tetrachloro[1,1'-biphenyl]-4,4'-diyl)bis{4-trifluoroacetylamino-3-[(E)-diazenyl]naphthalene-1-sulfonic acid}

1,1'-(3,3'-ditrifluoromethyl[1,1'-biphenyl]-4,4'-diyl)bis{4-trifluoroacetylamino-3-[(E)-diazenyl]naphthalene-1-sulfonic acid}

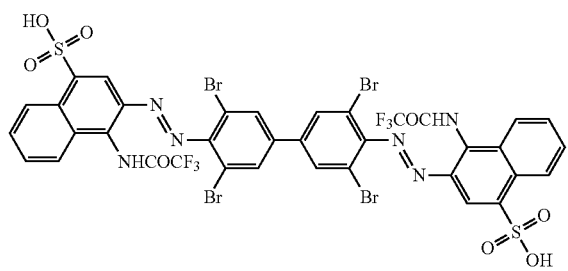 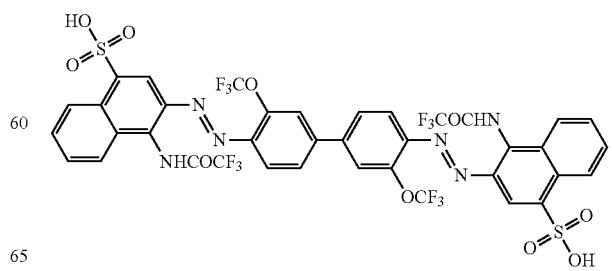

1,1'-(3,3'-ditrifluoromethoxy[1,1'-biphenyl]-4,4'-diyl)bis{4-trifluoroacetylamino-3-[(E)-diazenyl]naphthalene-1-sulfonic acid}

Another embodiment, the compound of this invention has the following structural formula:

Formula II

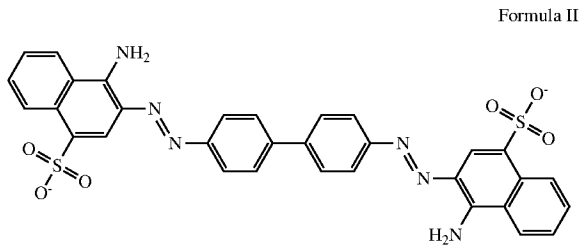 [SMILES: Nc1c(/N=N/c2ccc(-c3ccc(/N=N/c4cc(S(=O)(=O)[O-])c5ccccc5c4N)cc3)cc2)cc(S(=O)(=O)[O-])c2ccccc12]

To this end, Pol γ protein inhibitor compound is identified and characterized. The compound disclosed in the present application inhibits the activity of Pol γ enzyme. The compound is useful for selectively inhibiting the growth of MLH1 mutant/deficient tumor or cancer cells due to a synthetic lethal relationship between MLH1 and Pol γ. In this invention, the compounds described herein were shown to directly interact with Pol γ and inhibit its biological function and cause cancer cell death and an inhibition of cancer cell growth selectively in multiple assays.

Utility of the compounds in treating tumors as hereinabove specified, is demonstrated in animal test methods as well as in clinic by using preferably the compound described in formula II, for example in accordance with the methods hereinafter described.

FIG. 1 (a-b) shows the in silica interaction between the Pol γ protein and Pol γ protein inhibitor compound. FIG. 1 (a) indicates that 3D coordinates of the crystal structure of Pol γ (PDB ID: 3IKM) was selected as the receptor models in docking programs. The binding models for Pol γ inhibitors were predicted by using GOLD (GOLD Suite v5.2.2) on a Windows server equipped with an Intel Core i7 4600U processor (2.7 GHz) and 8 GB of RAM. Moreover, visualization of Formula II in the binding pocket of the catalytic subunit of Pol γ that was generated by the Accelrys Discovery Studio Visualizer software is shown in the FIG. 1(b). Chemical structure of the lead molecule described in Formula II; which has a molecular weight of 650.684 g.

Direct binding kinetics of Pol γ protein inhibitor compound was analysed and the response (RU) vs time graph was obtained. Direct binding kinetics was analysed by surface plasmon resonance (SPR) and corresponding response (RU)-time graph is indicated in FIG. 2. The novel compound developed by the present invention is found to bind to Pol 7 with an affinity of 0.5 micromolar by SPR experiments. SPR sensogram outputs illustrate the direct binding kinetics of the novel compound to recombinant wild type human Pol γ protein. SPR allows the measurement of direct molecular interactions in real-time and in a label-free setting. Recombinant wild type human Pol γ protein was immobilized onto a Biacore T100 CM5 sensor chips and molecules injected one-at-a time at 7 different concentrations. SPR sensogram and $K_D$ values were determined using Biacore software. An average affinity for Pol γ protein inhibitor compound binding to Pol γ from 3 independent experiments was calculated. The novel compound which binds to the catalytic subunit A of Pol γ showed the strongest direct binding affinity to the protein with a KD value 0.5 µM±0.05 µM.

The novel compound developed by the invention inhibits Pol γ DNA synthesis activities on a 1-nt gap containing base excision repair (BER) substrate and these activities are indicated in FIGS. 3 (a-e). A schematic of the 51-bp DNA substrate containing 1-nt gap at position 26 is shown before and after Pol γ addition (black star is 5'-$^{32}$P is labeled.) (FIG. 3a).

FIG. 3(b) screens hit molecules which were selected according to the binding kinetics to Pol γ protein for modulation of Pol γ strand displacement DNA synthesis activity. Reactions containing 40 nM Pol γ protein alone (lane 3) or together with a selected molecule at a final concentration of 20 µM (lanes 4-14) and 100 fmol 5' $^{35}$P-labeled 1-nt gap containing duplex substrate were incubated at 37° C. for 20 min. Lane 1, 51 mer oligodeoxynucleotide (used as a marker), Lane 2, substrate alone. Reaction products were run on a 20% denaturing polyacrylamide gel and visualized by a Typhoon Phosphorimager. Molecule number 1 (lane 4) that is the compound developed by the present invention strongly inhibits Pol γ strand displacement DNA synthesis activity.

FIG. 3-c shows that the novel compound developed by the invention inhibits Pol γ strand displacement DNA synthesis activity on a concentration dependent manner. Reactions contained Pol γ alone (40 nM; lane 3) or together with increasing concentrations of the novel compound (0.5, 1.25, 2.5, 5, and 10 µM; lanes 4-7). The reactions were initiated by adding 100 fmol 5' 32P-labeled 1-nt gap containing substrate and were incubated at 37° C. for 20 min. Reaction products were run on a 20% denaturing polyacrylamide gel and visualized by a Typhoon Phosphorimager. The triangle shape, ▲, refers to 40 nM heat-denatured Pol γ protein (lane 8). Lane 1 in FIG. 3-c refers to 51 mer oligodeoxynucleotide (used as a marker) and Lane 2 refers to substrate alone.

Graph represented in FIG. 3 (d) shows the percent control strand displacement values which were determined with ImageQuant software for the novel compound. Error bars represents SD from 3 independent experiments and a representative gel image is shown in FIG. 3 (a). The percent of each product with a given number of nucleotides incorporated is preferably calculated with the Equation 1. of total $$\% \text{ of total} = \frac{\text{amount of radioactivity associated with each } dNMP \text{ addition}}{\text{total radioactivity}} \times 100 \qquad \text{Equation 1}$$

$IC_{50}$ is calculated using GraphPad Prism software. The strand displacement DNA synthesis activity of Pol γ was inhibited by the novel compound with an $IC_{50}$ of 1.15 µM.

The novel compound described in Formula II inhibits Pol γ 1-nt incorporation activity and this can be observed in FIG. 3(e). The reaction conditions in FIG. 3(e) have same conditions described in FIG. 3(c) except dNTP was replaced with dCTP for 1-nt dCTP incorporation. The novel compound inhibits Pol γ 1-nt incorporation activity on concentration dependent manner (lanes 3-6 in FIG. 3 (c)). Lane 1 in FIG. 3(e) refers to substrate alone and Lane 2 is Pol γ alone.

FIG. 3 (f) represents percent of control 1-nucleotide incorporation activity determined with ImageQuant software for Pol γ protein inhibitor compound. Error bars represents SD from three independent experiments. A representative gel image is shown in FIG. 3(e). Reaction products were calculated as a function of radioactivity as described in FIG. 3(d). 1-nt incorporation activity of Pol γ was inhibited by the novel compound with an $IC_{50}$ of 1.18 µM.

Therefore, according to quantitation of nucleotide incorporation which shows the novel compound DNA synthesis activities indicated in FIG. 3 (a-f), it is seen that the novel compound described in Formula II inhibits Pol γ DNA synthesis activities on a 1-nt gap containing BER substrate.

The effect of novel compound on cell growth and proliferation is shown in FIG. 4 (a-c). The compound developed by the invention was also found to be selectively lethal to the MLH1 deficient HCT116 human colon carcinoma cell line compared to MLH1 proficient cell lines including HCT116V, HeLa (cervical cancer) and Lovo (MSH2 deficient colon cancer).

In FIG. 4 (a) and 4(b) shows that real time dynamic which is monitoring of HCT116 and HCT116V cell proliferation and the novel compound induced cytotoxicity with xCELLigence system. The xCELLigence system is precise and convenient to identify proliferation and cytotoxicity kinetics of cell lines in real-time. It is a very sensitive to determine optimal time points and cell numbers for cytotoxicity studies and in calculating $IC_{50}$ values. After seeding 15000 cells/well in 16 well E-plate, the proliferation of HCT116 and HCT116V cells was monitored every 30 min by the xCELLigence DP system. Approximately 22 h after seeding, when the cells in the log growth phase, HCT116 and HCT116V cells were treated with increasing concentrations of the novel compound (5 µM, 10 µM, and 20 µM), and monitored for every 30 min for 72 h. The cells were also treated with 0.02% DMSO served as a vehicle control. Cell index (CI) was normalized to the time point of the compound described in Formula II administration. Normalized CI was plotted as the mean value from duplicates; error bars represent the SD of mean. The RTCA software was used to calculate $IC_{50}$ values from the dose response curve. Grey arrow indicates the time of the novel compound (solid line on the graphs) at the addition of the novel compound administration. The compound in formula II exerted cytotoxic effect on HCT116 cell lines in a concentration dependent manner. The $IC_{50}$ value for HCT116 was 5.19 µM but $IC_{50}$ for HCT116V was 1324 µM.

Effect of the novel compound on proliferation of HCT116V, HCT116, SW48 and Lovo cell lines are indicate in FIG. 4-c. Cell proliferation was measured using the WST-1 assay (end point assay). Cell lines were plated onto a 96-well plate at 5000 cells per well in duplicate. Cell lines were treated with DMSO (as a control; 0.02%) or different concentration of the novel compound (20 µM and 50 µM) and were incubated at 37° C. for 48 h. For background subtraction, plates lacking cells but containing medium and molecule were used. After 48 h incubation, WST1 reagent was added for 2 h and OD440 was measured using a microplate reader. Percent cell proliferation was calculated as (molecule treated/untreated)×100. Cell proliferation data are the mean of two independent experiments with SD indicated by error bars. The novel compound inhibited HCT116 cell proliferation by 35% at 20 µM and by 50% at 50 µM. However, it was found that the molecule did not inhibit the cell proliferation of other cell lines.

The compound developed by this invention increased mitochondrial apoptosis in HCT116 cell line compared to HCT116V cell line and FIG. 5-a shows increased mitochondrial apoptosis. The compound decreased mtDNA copy number in HCT116 cell line compared to HCT116V cell line and FIG. 5-b shows decreased mtDNA copy number.

Results obtained from HCT116 Xenograft studies are indicated in FIG. 6 (a), (b) and (c). These figures shows HCT116 Xenograft studies in 6 independent nude mice demonstrated the decrease in the tumor volume after Pol γ protein inhibitor compound treatment. Tumor volume ($mm^3$) vs days the graph is indicated in FIG. 6 (a), body weight vs days after injection graph is in FIG. 6 (b), and FIG. 6 (c) is HCT116 Control vs 50 g/kg image.

On the other hand, results obtained from Lovo Xenograft studies are indicated in FIG. 7 (a), (b) and (c). Tumor volume ($mm^3$) vs days the graph is indicated in FIG. 7 (a), body weight vs days after injection graph is in FIG. 7 (b), and FIG. 7 (c) is HCT116 Control vs 50 g/kg image.

Xenograft studies in nude mice (Crl:NU(NCr)-Foxn1 purchased from Charles River Laboratories) using the HCT116 cell line demonstrated that consistently the novel compound decreased tumor volume in all doses (FIG. 6). The novel compound did not affect the tumor growth of Lovo xenograft (FIG. 7) These data demonstrate that the novel compound described in formula II is useful as a chemotherapeutic molecule for the selective treatment of MLH1-deficient colorectal cancers.

The studies shows that the present Pol γ protein inhibitor compound was identified and characterized in order to treat patients with Lynch syndrome (hereditary nonpolyposis colorectal cancer —HNPCC) have a MMR deficiency because of MLH1 mutations. When considering researches and test results, treating these cells with the novel Pol γ protein inhibitor that has specific cytotoxic activity against colon cancer cells specifically kills tumor cells without damaging normal cells.

In one embodiment, compound I disclosed in the present application which has the ability to inhibit Pol γ protein is used in the treatment, prevention or delaying of MLH1-deficient cancer or tumor cells. Patients with Lynch syndrome (hereditary nonpolyposis colorectal cancer —HNPCC) have a MMR deficiency because of MLH1 mutations; therefore treating these cells with (Pol γ) inhibiting compounds could possibly specifically kill tumor cells without damaging normal cells.

In another embodiment, compound I disclosed in the present application is used in the treatment, prevention or delaying of growing MLH1 deficient tumor or cancer cells.

In alternative embodiment, compound represented by the present invention is for use in the treatment, prevention or delaying of MLH1 protein deficient cancers due to mutations in MLH1 gene or MLH1 gene promoter methylation.

In another embodiment, the compound I developed by the present invention is used for inhibiting mitochondrial BER pathway.

In another embodiment, the compound I developed by the present invention is used for the treatment, prevention or delaying of mitochondrial cancer therapy.

In another embodiment, the compound may be administered with a therapeutic agent separately or in a combinatorial therapy. These additional therapeutic agents are selected from an anti-angiogenesis agent, selective estrogen-receptor modulator (SERM), aromatase inhibitor, biologic response modifiers, hormonal therapies agent, anthracycline, taxane, alkylating agent, taxol, cis-platin, arabinofuranosyl cytosine (ara-C), 5-fluorouracil (5-FU), altretamine, busulfan, chlorambucil, cyclophosphamide, ifosfamide, mechlorethamine, melphalan, thiotepa, cladribine, fluorouracil, floxuridine, gemcitabine, thioguanine, pentostatin, methotrexate, 6-mercaptopurine, cytarabine, carmustine, lomustine, streptozotocin, carboplatin, oxaliplatin, iproplatin, tetraplatin, lobaplatin, JM216, JM335, fludarabine, aminoglutethimide, flutamide, goserelin, leuprolide, megestrol acetate, cyproterone acetate, tamoxifen, anastrozole, bicalutamide, dexamethasone, diethylstilbestrol, prednisone, bleomycin, dactinomycin, daunorubicin, doxirubicin, idarubicin, mitoxantrone, losoxantrone, mitomycin-c, plicamycin, paclitaxel, docetaxel, CPI-II, cpothilones, topotecan, irinotecan, 9-amino camptothecan, 9-nitro camptothecan, GS-211, etoposide, teniposide, vinbiastine, vincristine, vinorelbine, procarbazine, asparaginase, pegaspargase, methoxtrexate, octreotide, estramustine, hydroxyurea, tamoxifen, raloxifene, toremifene, exemestane, letrozole, anastrozole, megestrol, trastuzumab, bevacizumab, goserelin acetate, fulvestrant, doxorubicin, epirubicin, or cyclophosphonamide.

In other embodiment, the compound disclosed by the present invention is used in a method of treatment, prevention or delaying of growing MLH1 mutant/deficient HNPCC tumors or cancer cells or cancer cell growth through mitochondrial targeted therapy.

In one other embodiment, the Pol γ protein inhibitor compound developed by the present invention for use in the treatment/prevention or delaying of cancer cell growth in multiple assays.

In alternative embodiment, the compound developed by the present invention is used in the pharmaceutical composition for use in inhibiting Pol γ enzyme. Pharmaceutical composition may optionally comprise pharmaceutically acceptable diluent, carrier or excipient. Moreover, this pharmaceurical composition further comprise a theraupetic agent selected from an anti-angionesis agent, selective estrogen-receptor modulator (SERM), aromatase inhibitor, biologic response modifiers, hormonal therapies agent, anthracycline, taxane, alkylating agent, taxol, cis-platin, arabinofuranosyl cytosine (ara-C), 5-fluorouracil (5-FU), altretamine, busulfan, chiorambucil, cyclophosphamide, ifosfamide, mechlorethamine, melphalan, thiotepa, cladribine, fluorouracil, floxuridine, gemcitabine, thioguanine, pentostatin, methotrexate, 6-mercaptopurine, cytarabine, carmustine, lomustine, streptozotocin, carboplatin, oxaliplatin, iproplatin, tetraplatin, lobaplatin, JM216, JM335, fludarabine, aminoglutethimide, flutamide, goserelin, leuprolide, megestrol acetate, cyproterone acetate, tamoxifen, anastrozole, bicalutamide, dexamethasone, diethylstilbestrol, prednisone, bleomycin, dactinomycin, daunorubicin, doxirubicin, idarubicin, mitoxantrone, losoxantrone, mitomycin-c, plicamycin, paclitaxel, docetaxel, CPI-II, cpothilones, topotecan, irinotecan, 9-amino camptothecan, 9-nitro camptothecan, GS-211, etoposide, teniposide, vinblastine, vincristine, vinorelbine, procarbazine, asparaginase, pegaspargase, methoxtrexate, octreotide, estramustine, hydroxyurea, tamoxifen, raloxifene, toremifene, exemestane, letrozole, anastrozole, megestrol, trastuzumab, bevacizumab, goserelin acetate, fulvestrant, doxorubicin, epirubicin, or cyclophosphonamide. Therapeutically effective amount of a pharmaceutical composition is used to inhibit mitochondrial BER pathway and also used to treat/prevent or delay of tumor or cancer cell growth through mitochondrial targeted therapy.

In another embodiment, abovementioned pharmaceutical composition is used in treatment, prevention or delaying of growing MLH1 mutant/deficient tumor cell and cancer cell growth in multiple assays comprising Thanks to the compounds disclosed in the invention; Pol γ protein inhibitor compound that inhibit Pol γ BER DNA synthesis activity, and cause selective cytotoxicity to MLH1 deficient colon cancer cells are identified.

The invention claimed is:

1. A method of treatment/prevention of cancer cells which are MLH1 mutant/deficient, comprising the step of providing a pharmaceutical composition comprising therapeutically effective amount of a compound having the formula (II):

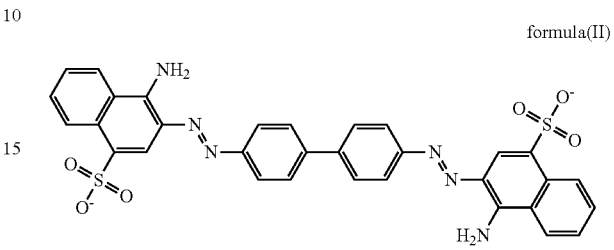

formula(II)

and/or pharmaceutically acceptable salts and/or pharmaceutically acceptable solvates in combination with pharmaceutically acceptable diluent, carrier or excipient thereof to a subject in need thereof.

2. A method of treatment/prevention or delay of MLH1 deficient cancers due to MLH1 promoter methylation, comprising the step of providing a pharmaceutical composition comprising therapeutically effective amount of a compound having the formula(II):

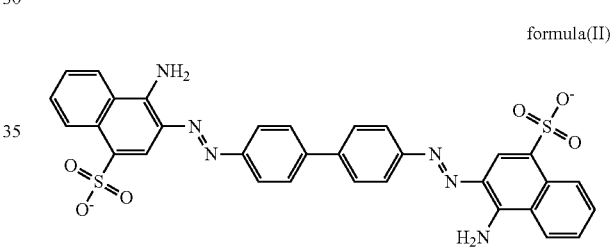

formula(II)

and/or pharmaceutically acceptable salts and/or pharmaceutically acceptable solvates in combination with pharmaceutically acceptable diluent, carrier or excipient thereof to a subject in need thereof.

3. A method of treatment/prevention or delay of tumor or cancer cell growth through mitochondrial targeted therapy, comprising the step of providing a pharmaceutical composition comprising therapeutically effective amount of a compound having the formula(II):

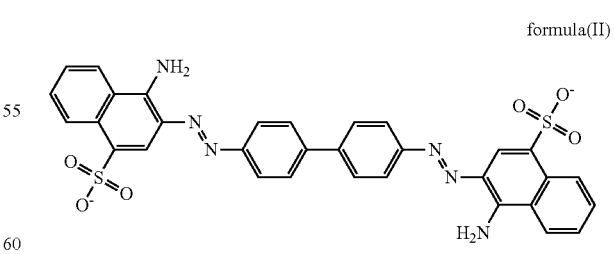

formula(II)

and/or pharmaceutically acceptable salts and/or pharmaceutically acceptable solvates in combination with pharmaceutically acceptable diluent, carrier or excipient thereof to a subject in need thereof.

* * * * *